US007179601B2

(12) United States Patent
Ausubel et al.

(10) Patent No.: US 7,179,601 B2
(45) Date of Patent: Feb. 20, 2007

(54) METHODS OF IDENTIFYING PLANT DISEASE-RESISTANCE GENES

(76) Inventors: Frederick M. Ausubel, 271 Lake Ave., Newton, MA (US) 02161; Brian J. Staskawicz, 18945 Marciel Ct., Castro Valley, CA (US) 94546; Andrew F. Bent, 6214 N. Highlands Ave., Madison, WI (US) 53705; Douglas Dahlbeck, 18851 Lenross Ct., Castro Valley, CA (US) 94546; Fumiaki Katagiri, 4503 Ocean Valley La., San Diego, CA (US) 92130; Barbara N. Kunkel, 34 Arundel Pl., St. Louis, MO (US) 63105; Michael Nicholas Mindrinos, 1670 El Camino Real #259, Menlo Park, CA (US) 94025; Guo-Liang Yu, 242 Gravatt Dr., Berkeley, CA (US) 94705; Barbara Baker, 7401 Claremont Ave., Berkeley, CA (US) 94705; Jeffrey Ellis, 10 Gibbes Pl., Weetangera Act 2614 (AU); John Salmeron, 1308 Blackberry La., Hillsborough, NC (US) 27278

( * ) Notice: Subject to any disclaimer, the term of this patent is extended or adjusted under 35 U.S.C. 154(b) by 78 days.

(21) Appl. No.: 10/613,472

(22) Filed: Jul. 2, 2003

(65) Prior Publication Data
US 2004/0088756 A1    May 6, 2004

Related U.S. Application Data

(60) Continuation of application No. 09/867,852, filed on May 29, 2001, now abandoned, which is a continuation of application No. 09/301,085, filed on Apr. 28, 1999, now Pat. No. 6,262,248, which is a division of application No. 08/310,912, filed on Sep. 22, 1994, now Pat. No. 5,981,730, which is a continuation-in-part of application No. 08/227,360, filed on Apr. 13, 1994, now abandoned.

(51) Int. Cl.
  *C12Q 1/68* (2006.01)
(52) U.S. Cl. ........................................................ 435/6
(58) Field of Classification Search ................ 800/279
  See application file for complete search history.

(56) References Cited

U.S. PATENT DOCUMENTS

| 5,237,056 A | 8/1993 | Fischbach ................. 536/23.5 |
| 5,571,706 A | 11/1996 | Baker et al. ............... 435/172.3 |
| 5,693,507 A * | 12/1997 | Daniell et al. ............. 435/470 |

FOREIGN PATENT DOCUMENTS

| EP | 0 544 250 A2 | 6/1993 |
| EP | 0 686 696 A1 | 12/1995 |
| WO | WO90/12097 | 10/1990 |
| WO | WO91/15585 | 10/1991 |
| WO | WO93/11241 | 6/1993 |
| WO | WO95/18230 | 7/1995 |
| WO | WO95/28423 | 10/1995 |
| WO | WO95/29238 | 11/1995 |
| WO | WO95/31560 | 11/1995 |
| WO | WO95/31564 | 11/1995 |
| WO | WO95/35024 | 12/1995 |

OTHER PUBLICATIONS

Keen et al, 1993, Biotechnology in Plant Disease Control (Chet, ed.), p. 65-88.*
Jaynes et al, 1993, Plant Science 89:43-53.*
Arlat et al., "PopA1, a Protein which Induces a Hypersensitivity-Like Response on Specific Petunia Genotypes, is Secreted via the Hrp Pathway of *Pseudomonas solanacearum*," *EMBO J.* 13:543-553 (1994).
Ausubel et al., "Use of *Arabidopsis thaliana* Defense-Related Mutants to Dissect the Plant Response to Pathogens," *Proc. Natl. Acad. Sci. USA* 92:4189-4196 (1995).
Baker et al., "Isolation of the Tabacco Mosaic Virus Resistance Gene N," *Advances in Molecular Genetics of Plant-Microbe Interactions* 3:297-302 (1994).
Bent et al., "RPS2 of *Arabidopsis thaliana*: A Leucine-Rich Repeat Class of Plant Disease Resistance Genes," *Science* 265:1856-1860 (1994).
Bunz et al., "cDNAs Encoding the Large Subunit of Human Replication Factor C," *Proc. Natl. Acad. Sci. USA* 90:11014-11018 (1993).
Burbelo et al., "Cloning of the Large Subunit of Activator 1 (Replication Factor C) Reveals Homology with Bacterial DNA Ligases," *Proc. Natl. Acad. Sci. USA* 90:11543-11547 (1993).
Carmona et al., "Expression of the Alpha-Thionin Gene from Barley in Tobacco Confers Enhance Resistance to Bacterial Pathogens," *The Plant Journal* 3:457-462 (1993).
Chasan, "Meeting Report: Plant-Pathogen Encounters in Edinburgh," *The Plant Cell* 10:1332-1341 (1994).
Cornelissen et al., "Strategies for Control of Fungal Diseases with Transgenic Plants," *Plant Physiology* 101:709-712 (1993).
Dalrymple et al., "Cloning and Characterisation of cDNA Clones Encoding Two *Babesia bovis* Proteins with Homologous Amino- and Carboxy-Terminal Domains," *Molecular and Biochemical Parasitology* 59:181-190 (1993).

(Continued)

*Primary Examiner*—Anne Kubelik
(74) *Attorney, Agent, or Firm*—Clark & Elbing LLP

(57) ABSTRACT

The invention relates to a method of identifying a plant disease-resistance gene that includes the steps of (a) providing a plant tissue sample; (b) introducing by biolistic transformation into the plant tissue sample a candidate plant disease-resistance gene; (c) expressing the candidate plant disease-resistance gene within the plant tissue sample; and (d) determining whether the plant tissue sample exhibits a disease-resistance response, whereby a response identifies a plant disease-resistance gene.

2 Claims, 30 Drawing Sheets

OTHER PUBLICATIONS

Dean, "Advantages of Arabidopsis for Cloning Plant Genes," *Phil. Trans. R. Soc. Lond.* 342:189-195 (1993).

Dinesh-Kumar et al., "Transposon Tagging of Tobacco Mosaic Virus Resistance Gene N: Its Possible Role in the TMV-N- Mediated Signal Transduction Pathway," *Proc. Natl. Acad. Sci. USA* 92:4175-4180 (1995).

Dong et al., "Induction of Arabidopsis Defense Genes by Virulent and Avirulent *Pseudomonas syringae* Strains and by a Cloned Avirulence Gene," *The Plant Cell* 3:61-72 (1991).

Ellingboe, "Changing Concepts in Host-Pathogen Genetics," *Ann. Rev. Phytophathol.* 19:125-143 (1981).

Ellis et al., "Contrasting Complexity of Two Rust Resistance Loci in Flax," *Proc. Natl. Acad. Sci. USA* 92:4185-4188 (1995).

Flor, "Current Status of the Gene-for-Gene Concept," *Ann. Rev. Phytopathol.* 9:275-296 (1971).

Gabriel et al., "Gene-for-Gene Interactions of Five Cloned Avirulence Genes from *Xanthomonas campestris* vs. *Malvacearum* with Specific Resistance Genes in Cotton," *Proc. Natl. Acad. Sci. USA* 83:6415-6419 (1986).

Gabriel, "Working Models of Specific Recognition in Plant-Microbe Interactions," *Annu. Rev. Phytopathol.* 28:365-391 (1990).

Gill et al., "A New Cell Division Operon in *Escherichia coli,*" *Mol. Gen. Genet.* 205:134-145 (1986).

Giri et al., "Genomic Structure of the Cottontail Rabbit (Shope) Papillomavirus," *Proc. Natl. Acad. Sci. USA* 82:1580-1584 (1985).

Gould et al., "Use of the DNA Polymerase Chain Reaction for Homology Probing: Isolation of Partial cDNA or Genomic Clones Encoding the Iron-Sulfur Protein of Succinate Dehydrogenase from Several Species," *Proc. Natl. Acad. Sci. USA* 86:1934-1938 (1989).

Hahn et al., "Cultivar-Specific Elicitation of Barley Defense Reactions by the Phytotoxic Peptide NIP1 from *Rhynchosporium secalis,*" *Molecular Plant Microbe Interactions* 6:745-754 (1993).

Innes et al., "Molecular Analysis of Avirulence Gene *avrRpt2* and Identification of a Putative Regulatory Sequence Common to all Known *Pseudomonas syringae* Avirulence Genes," *J. Bacteriol.* 175:4859-4869 (1993).

Johal et al., "Reductase Activity Encoded by the *HM1* Disease Resistance Gene in Maize," *Science* 258:985-987 (1992).

Joosten et al., "Host Resistance to a Fungal Tomato Pathogen Lost by a Single Base-Pair Change in an Avirulence Gene," *Nature* 367:384-386 (1994).

Keen, "Host Range Determinants in Plant Pathogens and Symbiots," *Ann. Rev. Microbiol.* 42:421-440 (1988).

Keen, "Plant Disease Resistance Genes: Interactions with Pathogens and their Improved Utilization to Control Plant Diseases," *Biotechnology in Plant Disease Control* 65-88 (1993).

Keen, "The Molecular Biology of Disease Resistance," *Plant Molecular Biology* 19:109-122 (1992).

Kobayashi et al., "A Gene from *Pseudomonas syringae* pv. Glycinea with Homology to Avirulence Gene D from P. s. pv. Tomato but Devoid of the Avirulence Phenotype," *Molecular Plant-Microbe Interac.* 3:103-111 (1990).

Kobayashi et al., "Molecular Characterization of Avirulence Gene D from *Pseudomonas syringae* pv. Tomato," *Molecular Plant-Microbe Interactions* 3:94-102 (1990).

Kunkel et al., "*RPS2*, an Arabidopsis Disease Resistance Locus Specifying Recognition of *Pseudomonas syringae* Strains Expressing the Avirulence Gene *avrRpt2,*" *The Plant Cell* 5:865-875 (1993).

Lamb et al., "Emerging Strategies for Enhancing Crop Resistance to Microbial Pathogens," *Bio Technology* 10:1436-1445 (1992).

Lister et al., "Recombinant Inbred Lines for Mapping RELP and Phenotypic Markers in *Arabidopsis thaliana,*" *The Plant Journal* 4:745-750 (1993).

Lu et al., "Cloning And Expression of a Novel Human DNA Binding Protein, PO-GA," *Biochemical and Biophysical Research Communications* 193(2):779-786 (1993).

Mahon et al., "The Small Cardioactive Peptides A and B of *Aplysia* are Derived from a Common Precursor Molecule," *Proc. Natl. Acad. Sci. USA* 82:3925-3929 (1985).

Martin et al., "Map-Based Cloning of a Protein Kinase Gene Conferring Disease Resistance in Tomato," *Science* 262:1432-1436 (1993).

Mevarech et al., "Nucleotide sequence of a cyanobacterial *nifH* Gene Coding for Nitrogenase Reductase," *Proc. Natl. Acad. Sci. USA* 77:6476-6480 (1980).

Midland et al., "The Structures of Syringolides 1 and 2, Novel C-Glycosidic Elicitors from *Pseudomonas syringae* pv. Tomato," *J. Org. Chem.* 58:2940-2945 (1993).

Mindrinos et al., "The *A. thaliana* Disease Resistance Gene *RPS2* Encodes a Protein Containing a Nucleotide-Binding Site and Leucine-Rich Repeats," *Cell* 78:1089-1099 (1994).

Myers et al., "The Human Mid-Size Neurofilamel Subunit: a Repeat Protein Sequence and the Relationship of its Gene to the Intermediate Filament Gene Family," *EMBO J.* 6:1617-1626 (1987).

Newman et al., "Genes Galore: A Summary of Methods for Accessing Results from Large-Scale Partial Sequencing of Anonymous Arabidopsis cDNA Clones," *Plant Physiol.* 106:1241-1255 (1994).

Phillips et al., "*A. thaliana* Transcribed Sequence; Clone TASG104, 5'End," *EMBL Sequence Accession No. Z17993* (1992).

Polzar et al., "Nucleotide Sequence of a Full Length cDNA Clone Encoding the Deoxyribonuclease I From the Rat Parotid Gland," *Nucleic Acids Research* 18:7151 (1990).

Rust et al., "Mutagenically Separated PCR (MS-PCR): A Highly Specific One Step Procedure for Easy Mutation Detection," *Nucleic Acids Research* 21:3623-3629 (1993).

Sasaki et al., "Toward Cataloguing all Rice Genes: Large-Scale Sequencing of Randomly Chosen Rice cDNAs From a Callus cDNA Library," *The Plant Journal* 6:615-624 (1994) and GenBank listing D15211.

Staskawicz et al., "Molecular Characterization of Cloned Avirulence Genes from Race 0 and Race 1 of *Pseudomonas syringae* pv. Glycinea," *J. Bacteriol.* 169:5789-5794 (1987).

Staskawicz et al., "Genetic Analysis of Bacterial Disease Resistance in Arabidopsis and Closing of the *RPS2* Resistance Gene," *Curr. Plant Sci. Biotechnol. Agric.* 21:283-288 (1994).

Staskawicz et al., "Genetic Dissection of Bacterial Disease Resistance," *J. Cellular Biochemistry Supplement* 18a:75 (1994) Abstract.

Stotz et al., "Molecular Characterization of a Polygalacturonase Inhibitor from *Pyrus communis* L. cv Bartlett," *Plant Physiol.* 102:133-138 (1993).

Van den Ackerveken et al., "Molecular Analysis of the Avirulence Gene *avr9* of the Fungal Tomato Pathogen *Cladosporium fulvum* Fully Supports the Gene-for-Gene Hypothesis," *The Plant Journal* 2:359-366 (1992).

Wanner et al., "Recognition of the Avirulence Gene *avrB* from *Pseudomonas syringae* pv. Glycinea by *Arabidopsis thaliana,*" *Molecular Plant-Microbe Interactions* 6:582-591 (1993).

Whalen et al., "Identification of *Pseudomonas syringae* Pathogens of Arabidopsis and a Bacterial Locus Determining Avirulence on both Arabidopsis and Soybean," *The Plant Cell* 3:49-59 (1991).

Whitham et al., "The Product of the Tobacco Mosaic Virus Resistance Gene N: Similarity to Toll and the Interleukin-1 Receptor," *Cell* 78:1101-1115 (1994).

Whitham et al., "*Nicotiana glutinosa* Virus Resistance (N) Gene, Complete cds" *EMBL Sequence Accession No.* U15605 (1994).

Wilson et al., "2.2 Mb of Contiguous Nucleotide Sequence form Chromosome III of *C. elegans,*" *Nature* 368:32-38 (1994) and GenBank listing U56963.

Yu et al., "Arabidopsis Mutations at the *RPS2* Locus Result in Loss of Resistance to *Pseudomonas syringae* Strains Expressing the Avirulence Gene *avrRpt2,*" *Molecular Plant-Microbe Interactions* 6:434-443 (1993).

\* cited by examiner

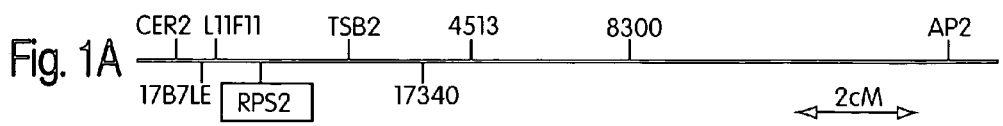
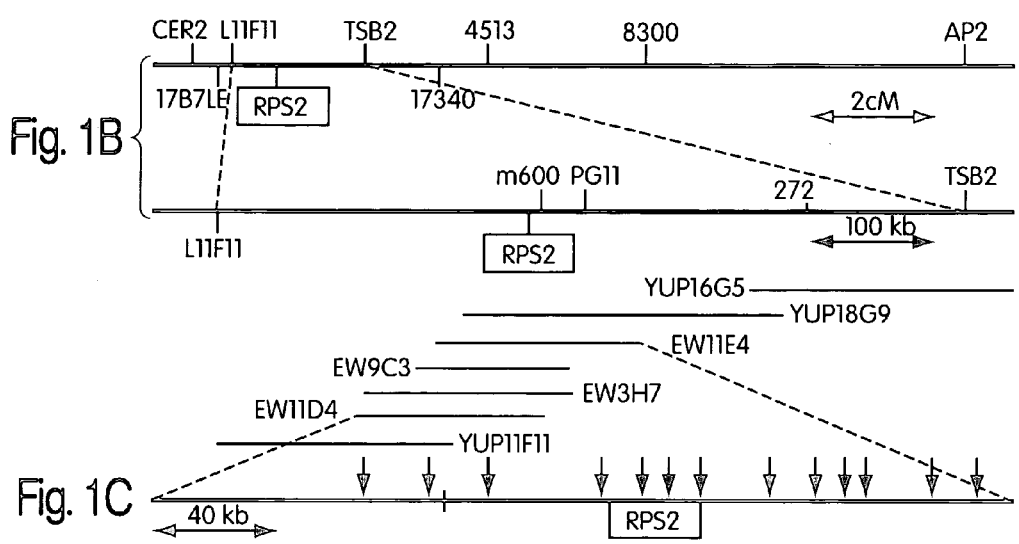
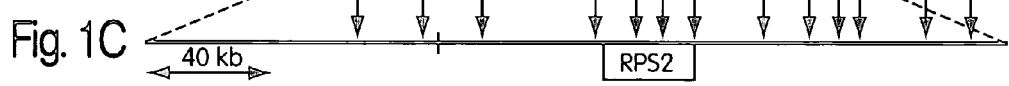
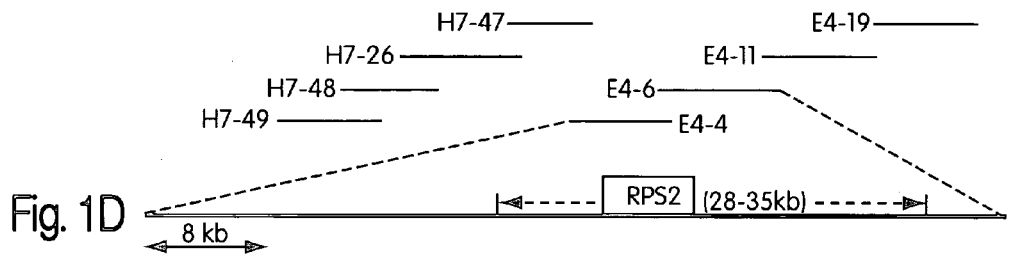
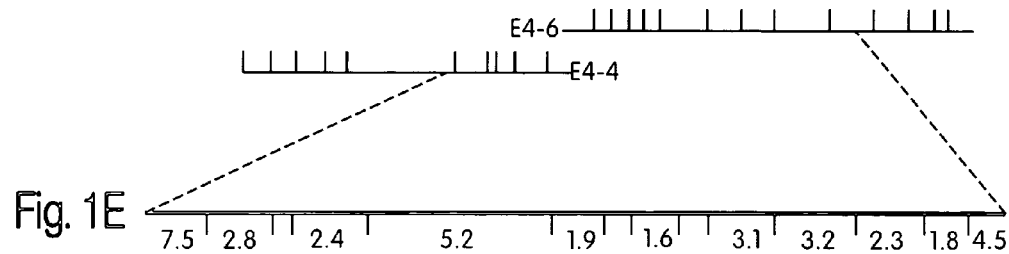
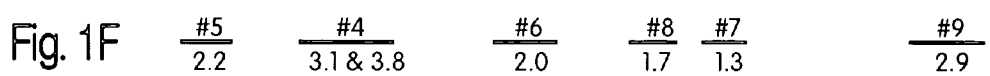

```
          AAGTAAAAGAAAGAGCGAGAAATCATCGAAATGGATTTCATCTCATCTCTTATCGTTGGC
     1    ---------+---------+---------+---------+---------+---------+  60
          TTCATTTTCTTTCTCGCTCTTTAGTAGCTTTACCTAAAGTAGAGTAGAGAATAGCAACCG a    K * K K E R E I I E Ⓜ D F I S S L I V G  -
  b     S K R K S E K S S K W I S S H L L S L A -
  c      V K E R A R N H R N G F H L I S Y R W L -

TGTGCTCAGGTGTTGTGTGAATCTATGAATATGGCGGAGAGAAGAGGACATAAGACTGAT
    61    ---------+---------+---------+---------+---------+---------+ 120
          ACACGAGTCCACAACACACTTAGATACTTATACCGCCTCTCTTCTCCTGTATTCTGACTA a    C A Q V L C E S M N M A E R R G H K T D  -
  b     V L R C C V N L * I W R R E E D I R L I -
  c      C S G V V * I Y E Y G G E K R T * D * S -

CTTAGACAAGCCATCACTGATCTTGAAACAGCCATCGGTGACTTGAAGGCCATACGTGAT
   121    ---------+---------+---------+---------+---------+---------+ 180
          GAATCTGTTCGGTAGTGACTAGAACTTTGTCGGTAGCCACTGAACTTCCGGTATGCACTA a    L R Q A I T D L E T A I G D L K A I R D  -
  b     L D K P S L I L K Q P S V T * R P Y V M -
  c      * T S H H * S * N S H R * L E G H T * * -

GACCTGACTTTACGGATCCAACAAGACGGTCTAGAGGGACGAAGCTGCTCAAATCGTGCC
   181    ---------+---------+---------+---------+---------+---------+ 240
          CTGGACTGAAATGCCTAGGTTGTTCTGCCAGATCTCCCTGCTTCGACGAGTTTAGCACGG a    D L T L R I Q Q D G L E G R S C S N R A  -
  b     T * L Y G S N K T V * R D E A A Q I V P -
  c      P D F T D P T R R S R G T K L L K S C Q -

AGAGAGTGGCTTAGTGCGGTGCAAGTAACGGAGACTAAAACAGCCCTACTTTTAGTGAGG
   241    ---------+---------+---------+---------+---------+---------+ 300
          TCTCTCACCGAATCACGCCACGTTCATTGCCTCTGATTTTGTCGGGATGAAAATCACTCC a    R E W L S A V Q V T E T K T A L L L V R  -
  b     E S G L V R C K * R R L K Q P Y F * * G -
  c      R V A * C G A S N G D * N S P T F S E V -

TTTAGGCGTCGGGAACAGAGGACGCGAATGAGGAGGAGATACCTCAGTTGTTTCGGTTGT
   301    ---------+---------+---------+---------+---------+---------+ 360
          AAATCCGCAGCCCTTGTCTCCTGCGCTTACTCCTCCTCTATGGAGTCAACAAAGCCAACA a    F R R R E Q R T R M R R R Y L S C F G C  -
  b     L G V G N R G R E * G G D T S V V S V V -
  c      * A S G T E D A N E E E I P Q L F R L C -

GCCGACTACAAACTGTGCAAGAAGGTTTCTGCCATATTGAAGAGCATTGGTGAGCTGAGA
   361    ---------+---------+---------+---------+---------+---------+ 420
          CGGCTGATGTTTGACACGTTCTTCCAAAGACGGTATAACTTCTCGTAACCACTCGACTCT
```

GAACGCTCTGAAGCTATCAAAACAGATGGCGGGTCAATTCAAGTAACTTGTAGAGAGATA
421    ---------+---------+---------+---------+---------+---------+ 480
       CTTGCGAGACTTCGATAGTTTTGTCTACCGCCCAGTTAAGTTCATTGAACATCTCTCTAT a   E R S E A I K T D G G S I Q V T C R E I     -
b    N A L K L S K Q M A G Q F K * L V E R Y    -
c     T L * S Y Q N R W R V N S S N L * R D T   -

CCCATCAAGTCCGTTGTCGGAAATACCACGATGATGGAACAGGTTTTGGAATTTCTCAGT
481    ---------+---------+---------+---------+---------+---------+ 540
       GGGTAGTTCAGGCAACAGCCTTTATGGTGCTACTACCTTGTCCAAAACCTTAAAGAGTCA a   P I K S V V G N T T M M E Q V L E F L S     -
b    P S S P L S E I P R * W N R F W N F S V    -
c     H Q V R C R K Y H D D G T G F G I S Q *   -

GAAGAAGAAGAAAGAGGAATCATTGGTGTTTATGGACCTGGTGGGGTTGGGAAGACAACG
541    ---------+---------+---------+---------+---------+---------+ 600
       CTTCTTCTTCTTTCTCCTTAGTAACCACAAATACCTGGACCACCCCAACCCTTCTGTTGC a   E E E E R G I I G V Y G P G G V G K T T     -
b    K K K K E E S L V F M D L V G L G R Q R    -
c     R R R K R N H W C L W T W W G W E D N V   -

TTAATGCAGAGCATTAACAACGAGCTGATCACAAAAGGACATCAGTATGATGTACTGATT
601    ---------+---------+---------+---------+---------+---------+ 660
       AATTACGTCTCGTAATTGTTGCTCGACTAGTGTTTTCCTGTAGTCATACTACATGACTAA a   L M Q S I N N E L I T K G H Q Y D V L I     -
b    * C R A L T T S * S Q K D I S M M Y * F    -
c     N A E H * Q R A D H K R T S V * C T D L   -

TGGGTTCAAATGTCCAGAGAATTCGGCGAGTGTACAATTCAGCAAGCCGTTGGAGCACGG
661    ---------+---------+---------+---------+---------+---------+ 720
       ACCCAAGTTTACAGGTCTCTTAAGCCGCTCACATGTTAAGTCGTTCGGCAACCTCGTGCC a   W V Q M S R E F G E C T I Q Q A V G A R     -
b    G F K C P E N S A S V Q F S K P L E H G    -
c     G S N V Q R I R R V Y N S A S R W S T V   -

TTGGGTTTATCTTGGGACGAGAAGGAGACCGGCGAAAACAGAGCTTTGAAGATATACAGA
721    ---------+---------+---------+---------+---------+---------+ 780
       AACCCAAATAGAACCCTGCTCTTCCTCTGGCCGCTTTTGTCTCGAAACTTCTATATGTCT a   L G L S W D E K E T G E N R A L K I Y R     -
b    W V Y L G T R R R P A K T E L * R Y T E    -
c     G F I L G R E G D R R K Q S F E D I Q S   -

GCTTTGAGACAGAAACGTTTCTTGTTGTTGCTAGATGATGTCTGGGAAGAGATAGACTTG
781    ---------+---------+---------+---------+---------+---------+ 840
       CGAAACTCTGTCTTTGCAAAGAACAACAACGATCTACTACAGACCCTTCTCTATCTGAAC
```

GAGAAAACTGGAGTTCCTCGACCTGACAGGGAAAACAAATGCAAGGTGATGTTCACGACA
841     ---------+---------+---------+---------+---------+---------+ 900
        CTCTTTTGACCTCAAGGAGCTGGACTGTCCCTTTTGTTTACGTTCCACTACAAGTGCTGT a   E K T G V P R P D R E N K C K V M F T T   -
b     R K L E F L D L T G K T N A R * C S R H   -
c       E N W S S S T * Q G K Q M Q G D V H D T -

CGGTCTATAGCATTATGCAACAATATGGGTGCGGAATACAAGTTGAGAGTGGAGTTTCTG
901     ---------+---------+---------+---------+---------+---------+ 960
        GCCAGATATCGTAATACGTTGTTATACCCACGCCTTATGTTCAACTCTCACCTCAAAGAC a   R S I A L C N N M G A E Y K L R V E F L   -
b     G L * H Y A T I W V R N T S * E W S F W   -
c       V Y S I M Q Q Y G C G I Q V E S G V S G -

GAGAAGAAACACGCGTGGGAGCTGTTCTGTAGTAAGGTATGGAGAAAAGATCTTTTAGAG
961     ---------+---------+---------+---------+---------+---------+ 1020
        CTCTTCTTTGTGCGCACCCTCGACAAGACATCATTCCATACCTCTTTTCTAGAAAATCTC a   E K K H A W E L F C S K V W R K D L L E   -
b     R R N T R G S C S V V R Y G E K I F * S   -
c       E E T R V G A V L * * G M E K R S F R V -

TCATCATCAATTCGCCGGCTCGCGGAGATTATAGTGAGTAAATGTGGAGGATTGCCACTA
1021    ---------+---------+---------+---------+---------+---------+ 1080
        AGTAGTAGTTAAGCGGCCGAGCGCCTCTAATATCACTCATTTACACCTCCTAACGGTGAT a   S S S I R R L A E I I V S K C G G L P L   -
b     H H Q F A G S R R L * * V N V E D C H *   -
c       I I N S P A R G D Y S E * M W R I A T S -

GCGTTGATCACTTTAGGAGGAGCCATGGCTCATAGAGAGACAGAAGAAGAGTGGATCCAT
1081    ---------+---------+---------+---------+---------+---------+ 1140
        CGCAACTAGTGAAATCCTCCTCGGTACCGAGTATCTCTCTGTCTTCTTCTCACCTAGGTA a   A L I T L G G A M A H R E T E E E W I H   -
b     R * S L * E E P W L I E R Q K K S G S M   -
c       V D H F R R S H G S * R D R R R V D P C -

GCTAGTGAAGTTCTGACTAGATTTCCAGCAGAGATGAAGGGTATGAACTATGTATTTGCC
1141    ---------+---------+---------+---------+---------+---------+ 1200
        CGATCACTTCAAGACTGATCTAAAGGTCGTCTCTACTTCCCATACTTGATACATAAACGG a   A S E V L T R F P A E M K G M N Y V F A   -
b     L V K F * L D F Q Q R * R V * T M Y L P   -
c       * * S S D * I S S R D E G Y E L C I C P -

CTTTTGAAATTCAGCTACGACAACCTCGAGAGTGATCTGCTTCGGTCTTGTTTCTTGTAC
1201    ---------+---------+---------+---------+---------+---------+ 1260
        GAAAACTTTAAGTCGATGCTGTTGGAGCTCTCACTAGACGAAGCCAGAACAAAGAACATG
```

TGCGCTTTATTCCCAGAAGAACATTCTATAGAGATCGAGCAGCTTGTTGAGTACTGGGTC
1261   ----------+---------+---------+---------+---------+---------+ 1320
       ACGCGAAATAAGGGTCTTCTTGTAAGATATCTCTAGCTCGTCGAACAACTCATGACCCAG a      C A L F P E E H S I E I E Q L V E Y W V -
b      A L Y S Q K N I L * R S S S L L S T G S -
c      R F I P R R T F Y R D R A A C * V L G R -

GGCGAAGGGTTTCTCACCAGCTCCCATGGCGTTAACACCATTTACAAGGGATATTTTCTC
1321   ----------+---------+---------+---------+---------+---------+ 1380
       CCGCTTCCCAAAGAGTGGTCGAGGGTACCGCAATTGTGGTAAATGTTCCCTATAAAAGAG a      G E G F L T S S H G V N T I Y K G Y F L -
b      A K G F S P A P M A L T P F T R D I F S -
c      R R V S H Q L P W R * H H L Q G I F S H -

ATTGGGGATCTGAAAGCGGCATGTTTGTTGGAAACCGGAGATGAGAAAACACAGGTGAAG
1381   ----------+---------+---------+---------+---------+---------+ 1440
       TAACCCCTAGACTTTCGCCGTACAAACAACCTTTGGCCTCTACTCTTTTGTGTCCACTTC a      I G D L K A A C L L E T G D E K T Q V K -
b      L G I * K R H V C W K P E M R K H R * R -
c      W G S E S G M F V G N R R * E N T G E D -

ATGCATAATGTGGTCAGAAGCTTTGCATTGTGGATGGCATCTGAACAGGGGACTTATAAG
1441   ----------+---------+---------+---------+---------+---------+ 1500
       TACGTATTACACCAGTCTTCGAAACGTAACACCTACCGTAGACTTGTCCCCTGAATATTC a      M H N V V R S F A L W M A S E Q G T Y K -
b      C I M W S E A L H C G W H L N R G L I R -
c      A * C G Q K L C I V D G I * T G D L * G -

GAGCTGATCCTAGTTGAGCCTAGCATGGGACATACTGAAGCTCCTAAAGCAGAAAACTGG
1501   ----------+---------+---------+---------+---------+---------+ 1560
       CTCGACTAGGATCAACTCGGATCGTACCCTGTATGACTTCGAGGATTTCGTCTTTTGACC a      E L I L V E P S M G H T E A P K A E N W -
b      S * S * L S L A W D I L K L L K Q K T G -
c      A D P S * A * H G T Y * S S * S R K L A -

CGACAAGCGTTGGTGATCTCATTGTTAGATAACAGAATCCAGACCTTGCCTGAAAAACTC
1561   ----------+---------+---------+---------+---------+---------+ 1620
       GCTGTTCGCAACCACTAGAGTAACAATCTATTGTCTTAGGTCTGGAACGGACTTTTTGAG a      R Q A L V I S L L D N R I Q T L P E K L -
b      D K R W * S H C * I T E S R P C L K N S -
c      T S V G D L I V R * Q N P D L A * K T H -
```

Fig. 2D

```
        ATATGCCCGAAACTGACAACACTGATGCTCCAACAGAACAGCTCTTTGAAGAAGATTCCA
1621    ---------+---------+---------+---------+---------+---------+  1680
        TATACGGGCTTTGACTGTTGTGACTACGAGGTTGTCTTGTCGAGAAACTTCTTCTAAGGT a       I   C   P   K   L   T   T   L   M   L   Q   Q   N   S   S   L   K   K   I   P   -
b         Y   A   R   N   *   Q   H   *   C   S   N   R   T   A   L   *   R   R   F   Q   -
c           M   P   E   T   D   N   T   D   A   P   T   E   Q   L   F   E   E   D   S   N  -

ACAGGGTTTTTCATGCATATGCCTGTTCTCAGAGTCTTGGACTTGTCGTTCACAAGTATC
1681    ---------+---------+---------+---------+---------+---------+  1740
        TGTCCCAAAAAGTACGTATACGGACAAGAGTCTCAGAACCTGAACAGCAAGTGTTCATAG a       T   G   F   F   M   H   M   P   V   L   R   V   L   D   L   S   F   T   S   I   -
b         Q   G   F   S   C   I   C   L   F   S   E   S   W   T   C   R   S   Q   V   S   -
c           R   V   F   H   A   Y   A   C   S   Q   S   L   G   L   V   V   H   K   Y   H  -

ACTGAGATTCCGTTGTCTATCAAGTATTTGGTGGAGTTGTATCATCTGTCTATGTCAGGA
1741    ---------+---------+---------+---------+---------+---------+  1800
        TGACTCTAAGGCAACAGATAGTTCATAAACCACCTCAACATAGTAGACAGATACAGTCCT a       T   E   I   P   L   S   I   K   Y   L   V   E   L   Y   H   L   S   M   S   G   -
b         L   R   F   R   C   L   S   S   I   W   W   S   C   I   I   C   L   C   Q   E   -
c           *   D   S   V   V   Y   Q   V   F   G   G   V   V   S   S   V   Y   V   R   N  -

ACAAAGATAAGTGTATTGCCACAGGAGCTTGGGAATCTTAGAAAACTGAAGCATCTGGAC
1801    ---------+---------+---------+---------+---------+---------+  1860
        TGTTTCTATTCACATAACGGTGTCCTCGAACCCTTAGAATCTTTTGACTTCGTAGACCTG a       T   K   I   S   V   L   P   Q   E   L   G   N   L   R   K   L   K   H   L   D   -
b         Q   R   *   V   Y   C   H   R   S   L   G   I   L   E   N   *   S   I   W   T   -
c           K   D   K   C   I   A   T   G   A   W   E   S   *   K   T   E   A   S   G   P  -

CTACAAAGAACTCAGTTTCTTCAGACGATCCCACGAGATGCCATATGTTGGCTGAGCAAG
1861    ---------+---------+---------+---------+---------+---------+  1920
        GATGTTTCTTGAGTCAAAGAAGTCTGCTAGGGTGCTCTACGGTATACAACCGACTCGTTC a       L   Q   R   T   Q   F   L   Q   T   I   P   R   D   A   I   C   W   L   S   K   -
b         Y   K   E   L   S   F   F   R   R   S   H   E   M   P   Y   V   G   *   A   S   -
c           T   K   N   S   V   S   S   D   D   P   T   R   C   H   M   L   A   E   Q   A  -

CTCGAGGTTCTGAACTTGTACTACAGTTACGCCGGTTGGGAACTGCAGAGCTTTGGAGAA
1921    ---------+---------+---------+---------+---------+---------+  1980
        GAGCTCCAAGACTTGAACATGATGTCAATGCGGCCAACCCTTGACGTCTCGAAACCTCTT a       L   E   V   L   N   L   Y   Y   S   Y   A   G   W   E   L   Q   S   F   G   E   -
b         S   R   F   *   T   C   T   T   V   T   P   V   G   N   C   R   A   L   E   K   -
c           R   G   S   E   L   V   L   Q   L   R   R   L   G   T   A   E   L   W   R   R  -

GATGAAGCAGAAGAACTCGGATTCGCTGACTTGGAATACTTGGAAAACCTAACCACACTC
1981    ---------+---------+---------+---------+---------+---------+  2040
        CTACTTCGTCTTCTTGAGCCTAAGCGACTGAACCTTATGAACCTTTTGGATTGGTGTGAG
```

GGTATCACTGTTCTCTCATTGGAGACCCTAAAAACTCTCTTCGAGTTCGGTGCTTTGCAT
2041  ---------+---------+---------+---------+---------+---------+ 2100
      CCATAGTGACAAGAGAGTAACCTCTGGGATTTTTGAGAGAAGCTCAAGCCACGAAACGTA a     G  I  T  V  L  S  L  E  T  L  K  T  L  F  E  F  G  A  L  H  -
b      V  S  L  F  S  H  W  R  P  *  K  L  S  S  S  S  V  L  C  I  -
c       Y  H  C  S  L  I  G  D  P  K  N  S  L  R  V  R  C  F  A  *  -

AAACATATACAGCATCTCCACGTTGAAGAGTGCAATGAACTCCTCTACTTCAATCTCCCA
2101  ---------+---------+---------+---------+---------+---------+ 2160
      TTTGTATATGTCGTAGAGGTGCAACTTCTCACGTTACTTGAGGAGATGAAGTTAGAGGGT a     K  H  I  Q  H  L  H  V  E  E  C  N  E  L  L  Y  F  N  L  P  -
b      N  I  Y  S  I  S  T  L  K  S  A  M  N  S  S  T  S  I  S  H  -
c       T  Y  T  A  S  P  R  *  R  V  Q  *  T  P  L  L  Q  S  P  I  -

TCACTCACTAACCATGGCAGGAACCTGAGAAGACTTAGCATTAAAAGTTGCCATGACTTG
2161  ---------+---------+---------+---------+---------+---------+ 2220
      AGTGAGTGATTGGTACCGTCCTTGGACTCTTCTGAATCGTAATTTTCAACGGTACTGAAC a     S  L  T  N  H  G  R  N  L  R  R  L  S  I  K  S  C  H  D  L  -
b      H  S  L  T  M  A  G  T  *  E  D  L  A  L  K  V  A  M  T  W  -
c       T  H  *  P  W  Q  E  P  E  K  T  *  H  *  K  L  P  *  L  G  -

GAGTACCTGGTCACACCCGCAGATTTTGAAAATGATTGGCTTCCGAGTCTAGAGGTTCTG
2221  ---------+---------+---------+---------+---------+---------+ 2280
      CTCATGGACCAGTGTGGGCGTCTAAAACTTTTACTAACCGAAGGCTCAGATCTCCAAGAC a     E  Y  L  V  T  P  A  D  F  E  N  D  W  L  P  S  L  E  V  L  -
b      S  T  W  S  H  P  Q  I  L  K  M  I  G  F  R  V  *  R  F  *  -
c       V  P  G  H  T  R  R  F  *  K  *  L  A  S  E  S  R  G  S  D  -

ACGTTACACAGCCTTCACAACTTAACCAGAGTGTGGGGAAATTCTGTAAGCCAAGATTGT
2281  ---------+---------+---------+---------+---------+---------+ 2340
      TGCAATGTGTCGGAAGTGTTGAATTGGTCTCACACCCCTTTAAGACATTCGGTTCTAACA a     T  L  H  S  L  H  N  L  T  R  V  W  G  N  S  V  S  Q  D  C  -
b      R  Y  T  A  F  T  T  *  P  E  C  G  E  I  L  *  A  K  I  V  -
c       V  T  Q  P  S  Q  L  N  Q  S  V  G  K  F  C  K  P  R  L  S  -

CTGCGGAATATCCGTTGCATAAACATTTCACACTGCAACAAGCTGAAGAATGTCTCATGG
2341  ---------+---------+---------+---------+---------+---------+ 2400
      GACGCCTTATAGGCAACGTATTTGTAAAGTGTGACGTTGTTCGACTTCTTACAGAGTACC a     L  R  N  I  R  C  I  N  I  S  H  C  N  K  L  K  N  V  S  W  -
b      C  G  I  S  V  A  *  T  F  H  T  A  T  S  *  R  M  S  H  G  -
c       A  E  Y  P  L  H  K  H  F  T  L  Q  Q  A  E  E  C  L  M  G  -

GTTCAGAAACTCCCAAAGCTAGAGGTGATTGAACTGTTCGACTGCAGAGAGATAGAGGAA
2401  ---------+---------+---------+---------+---------+---------+ 2460
      CAAGTCTTTGAGGGTTTCGATCTCCACTAACTTGACAAGCTGACGTCTCTCTATCTCCTT
```

TTGATAAGCGAACACGAGAGTCCATCCGTCGAAGATCCAACATTGTTCCCAAGCCTGAAG
2461   ---------+---------+---------+---------+---------+---------+ 2520
       AACTATTCGCTTGTGCTCTCAGGTAGGCAGCTTCTAGGTTGTAACAAGGGTTCGGACTTC a    L  I  S  E  H  E  S  P  S  V  E  D  P  T  L  F  P  S  L  K   -
b     *  *  A  N  T  R  V  H  P  S  K  I  Q  H  C  S  Q  A  *  R  -
c      D  K  R  T  R  E  S  I  R  R  R  S  N  I  V  P  K  P  E  D -

ACCTTGAGAACTAGGGATCTGCCAGAACTAAACAGCATCCTCCCATCTCGATTTTCATTC
2521   ---------+---------+---------+---------+---------+---------+ 2580
       TGGAACTCTTGATCCCTAGACGGTCTTGATTTGTCGTAGGAGGGTAGAGCTAAAAGTAAG a    T  L  R  T  R  D  L  P  E  L  N  S  I  L  P  S  R  F  S  F   -
b     P  *  E  L  G  I  C  Q  N  *  T  A  S  S  H  L  D  F  H  S  -
c      L  E  N  *  G  S  A  R  T  K  Q  H  P  P  I  S  I  F  I  P -

CAAAAAGTTGAAACATTAGTCATCACAAATTGCCCCAGAGTTAAGAAACTGCCGTTTCAG
2581   ---------+---------+---------+---------+---------+---------+ 2640
       GTTTTTCAACTTTGTAATCAGTAGTGTTTAACGGGGTCTCAATTCTTTGACGGCAAAGTC a    Q  K  V  E  T  L  V  I  T  N  C  P  R  V  K  K  L  P  F  Q   -
b     K  K  L  K  H  *  S  S  Q  I  A  P  E  L  R  N  C  R  F  R  -
c      K  S  *  N  I  S  H  H  K  L  P  Q  S  *  E  T  A  V  S  G -

GAGAGGAGGACCCAGATGAACTTGCCAACAGTTTATTGTGAGGAGAAATGGTGGAAAGCA
2641   ---------+---------+---------+---------+---------+---------+ 2700
       CTCTCCTCCTGGGTCTACTTGAACGGTTGTCAAATAACACTCCTCTTTACCACCTTTCGT a    E  R  R  T  Q  M  N  L  P  T  V  Y  C  E  E  K  W  W  K  A   -
b     R  G  G  P  R  *  T  C  Q  Q  F  I  V  R  R  N  G  G  K  H  -
c      E  E  D  P  D  E  L  A  N  S  L  L  *  G  E  M  V  E  S  T -

CTGGAAAAAGATCAACCAAACGAAGAGCTTTGTTATTTACCGCGCTTTGTTCCAAATTGA
2701   ---------+---------+---------+---------+---------+---------+ 2760
       GACCTTTTTCTAGTTGGTTTGCTTCTCGAAACAATAAATGGCGCGAAACAAGGTTTAACT a    L  E  K  D  Q  P  N  E  E  L  C  Y  L  P  R  F  V  P  N  *   -
b     W  K  K  I  N  Q  T  K  S  F  V  I  Y  R  A  L  F  Q  I  D  -
c      G  K  R  S  T  K  R  R  A  L  L  F  T  A  L  C  S  K  L  I -

TATAAGAGCTAAGAGCACTCTGTACAAATATGTCCATTCATAAGATGCAGGAAGCCAGGA
2761   ---------+---------+---------+---------+---------+---------+ 2820
       ATATTCTCGATTCTCGTGAGACATGTTTATACAGGTAAGTATTCTACGTCCTTCGGTCCT a    Y  K  S  *  E  H  S  V  Q  I  C  P  F  I  R  C  R  K  P  G   -
b     I  R  A  K  S  T  L  Y  K  Y  V  H  S  *  D  A  G  S  Q  E  -
c      *  E  L  R  A  L  C  T  N  M  S  I  H  K  M  Q  E  A  R  K -

AGGTTGTTCCAGTGAAGTCATCAACTTTCCACATAGCCACAAAACTAGAGATTATGTAAT
2821   ---------+---------+---------+---------+---------+---------+ 2880
       TCCAACAAGGTCACTTCAGTAGTTGAAAGGTGTATCGGTGTTTTGATCTCTAATACATTA
```

CATAAAAACCAAACTATCCGCGA
2881    ---------+---------+---  2903
        GTATTTTTGGTTTGATAGGCGCT a    H K N Q T I R     -
b     I K T K L S A    -
c      * K P N Y P R   -

ENZYMES THAT DO CUT:

NONE

ENZYMES THAT DO NOT CUT:

KpnI
```

Fig. 2H

```
                                                                        -146
ATCGATTGATCTCTGGCTCAGTGCGAGTAGTCCATTTGAGAGCAGTCGTAGCCCCGCGTG           -86

GCGCATCATGGAGCTATTTGGAATTTTCGCAGGGTTATCGATTCGTAGTGGGAACCCATT           -26

1
CATTGTTTGGAACCACCAACGGACGACTTAACAAGCTCCCCGAGGTGCATGATGAAAATT            35
                                                        MetLysIle

GCTCCAGTTGCCATAAATCACAGCCCGCTCAGCAGGGAGGTCCCGTCACACGCGGCACCC            95
AlaProValAlaIleAsnHisSerProLeuSerArgGluValProSerHisAlaAlaPro

ACTCAGGCAAAGCAAACCAACCTTCAATCTGAAGCTGGCGATTTAGATGCAAGAAAAAGT           155
ThrGlnAlaLysGlnThrAsnLeuGlnSerGluAlaGlyAspLeuAspAlaArgLysSer

AGCGCTTCAAGCCCGGAAACCCGCGCATTACTCGCTACTAAGACAGTACTCGGGAGACAC           215
SerAlaSerSerProGluThrArgAlaLeuLeuAlaThrLysThrValLeuGlyArgHis

AAGATAGAGGTTCCGGCCTTTGGAGGGTGGTTCAAAAAGAAATCATCTAAGCACGAGACG           275
LysIleGluValProAlaPheGlyGlyTrpPheLysLysLysSerSerLysHisGluThr

GGCGGTTCAAGTGCCAACGCAGATAGTTCGAGCGTGGCTTCCGATTCCACCGAAAAACCT           335
GlyGlySerSerAlaAsnAlaAspSerSerSerValAlaSerAspSerThrGluLysPro

TTGTTCCGTCTCACGCACGTTCCTTACGTATCCCAAGGTAATGAGCGAATGGGATGTTGG           395
LeuPheArgLeuThrHisValProTyrValSerGlnGlyAsnGluArgMetGlyCysTrp

TATGCCTGCGCAAGAATGGTTGGCCATTCTGTCGAAGCTGGGCCTCGCCTAGGGCTGCCG           455
TyrAlaCysAlaArgMetValGlyHisSerValGluAlaGlyProArgLeuGlyLeuPro

GAGCTCTATGAGGGAAGGGAGGCGCCAGCTGGGCTACAAGATTTTTCAGATGTAGAAAGG           515
GluLeuTyrGluGlyArgGluAlaProAlaGlyLeuGlnAspPheSerAspValGluArg

TTTATTCACAATGAAGGATTAACTCGGGTAGACCTTCCAGACAATGAGAGATTTACACAC           575
PheIleHisAsnGluGlyLeuThrArgValAspLeuProAspAsnGluArgPheThrHis
```

Fig. 3A

```
GAAGAGTTGGGTGCACTGTTGTATAAGCACGGGCCGATTATATTTGGGTGGAAAACTCCG    635
GluGluLeuGlyAlaLeuLeuTyrLysHisGlyProIleIlePheGlyTrpLysThrPro

AATGACAGCTGGCACATGTCGGTCCTCACTGGTGTCGATAAAGAGACGTCGTCCATTACT    695
AsnAspSerTrpHisMetSerValLeuThrGlyValAspLysGluThrSerSerIleThr

TTTCACGATCCCCGACAGGGGCCGGACCTAGCAATGCCGCTCGATTACTTTAATCAGCGA    755
PheHisAspProArgGlnGlyProAspLeuAlaMetProLeuAspTyrPheAsnGlnArg

TTGGCATGGCAGGTTCCACACGCAATGCTCTACCGCTAAGTAGCAGGGTATCTTCACGTG    815
LeuAlaTrpGlnValProHisAlaMetLeuTyrArgEnd

GCGGCATCATGACAAGCCCATGATGCCGCCAGCAGCTACCTGAATGCCGTCTGGCTTTTT    875

GGTCCCTATTGTCGTATCCGGAAGATGACGTCAAAGAATCTCGGCAAGAGCTTTCTTGCT    935

CGACTCCTCAGCTTCCGGATCGATCAGGTCGCTTGCCAGAGCGCGCTTGTCCATGAGCAT    995

CTGCCACAGCTGCTGGTCGATGGTGTCCTCAGCTAAAGGGATTTTGACGACAACCATGCG   1055

CAACTGCCCGTTGCGATACGCTCGATCCTGAAGCCCCGGTGTCCATGGCAGCCCCAAGAA   1115

AAAGACATAGTTCGCCGCTGTGAGGTTGTAGCCTGTGCCGGCGGCCGACCTGGTCCCGAT   1175

AAACACCCTGCAGTCCGGATCCTGCTGGAAAGCATCAATCGCCTTCTGCCGCTTCTTGGG   1235

CGAGTCACTGCCCACCAACGTCACGCACCCGACGCCAAGCTTGAGGCAGTGCTCCCGCAA   1295

CGTGGCCACGGATTCCTGATACTCGCAGAAGAGGATCACCTTGTCGTCGAC   1346
```

Fig. 3B

```
        1                                                           50
L6pro   MSYLREVATA VALLLPFILL NKFWRPNSKD SIVNDDDDST SEVDAISDST
Nprot   .......... .......... .......... .......... .........M
PrfP    .......... .......... .......... .......... ..........
rps2    .......... .......... .......... .......... ..........

51                  6                                      100
L6pro   NPSGSFPSVE YEVFLSFRGP DTREQFTDFL YQSLRRYKIM TFRDDDELLK
Nprot   ASSSSSSRWS YDVFLSFRGE DTRKTFTSHL YEVLNDKGIK TFQDDKRLEY
PrfP    .......... .......... .......... LRSKLDLIID LKHQIESVKE
rps2    .......... MDFISSLIVG CAQVLCESMN MAERRGHKTD LRQAITDLET 101                                                        150
L6pro   GKEIGPNLLR AIDQSKIYVP IISSGYADSK WCLMELAEIV RRQEEDPRRI
Nprot   GATIPGELCK AIEESQFAIV VFSENYATSR WCLNELVKIM ECK.TRFKQT
PrfP    GLLCLRSFID HFSESYDEHD ........EA CGLIARVSVM AYKAE.....
rps2    AIGDLKAIRD DLTLRIQQDG LEGRSCSNRA REWLSAVQVT ETKTA.....

151     7                                                  200
L6pro   ILPIFYMVDP SDVRHQTGCY KKAFRKHANK F..DGQTIQN WKDALKKVGD
Nprot   VIPIFYDVDP SHVRNQKESF AKAFEEHETK YKDDVEGIQR WRIALNEAAN
PrfP    .....YVIDS CLAYSHPLWY KVLW...... ..IS...... .EVLENIKLV
rps2    .....LLLVR FRRREQRTRM RRRY...... ..LSCFGCAD YKLCKKVSAI 201                                          8             250
L6pro   LKGWHIGKND KQGAIADKVS ADIWSHISKE NLILE...TD ELVGIDDHIT
Nprot   LKGSCDNRDK TDADCIRQIV DQISSKLCKI SLSY....LQ NIVGIDTHLE
PrfP    NKVVGETCER RNIEVTVHEV AKTTTYVAPS FSAYTQRANE EMEGFQDTID
rps2    LKSIGELRER SEAIKTDGGS IQVTCREIPI KSVVG..... ......NTTMM 251                          1      -P-loop               300
L6pro   AVLEKLSLDS ENVTMVGLYG MGGIGKTTTA KAVYNKI... ..SSC.FDCC
Nprot   KIESLLEIGI NGVRIMGIWG MGGVGKTTIA RAIFDTLLGR MDSSYQFDGA
PrfP    ELKDKLLGGS PELDVISIVG MPGLGKTTLA KKIYNDPEVT ..SRFDVHAQ
rps2    EQVLEFLSEE EERGIIGVYG PGGVGKTTLM QSINNELITK ..G....HQY 301                                                        350
L6pro   CFIDNIRETQ EKDGVVVLQK KLVSEILRID ..SGSVGFNN DSGGRKTIKE
Nprot   CFLKDIKE.. NKRGMHSLQN ALLSELLR.. ...EKANYNN EEDGKHQMAS
PrfP    CVVTQLYSWR EL.LLTILND VLEP...S.. ...DRNEKED GE.IADELRR
rps2    DVLIWVQMSR EF.GECTIQQ AVGA...RLG ..LSWDEKET GENRALKIYR 351       2                              3                400
L6pro   RVSRFKILVV LDDVDEKFKF EDMLGSPKDF ISQ.SRFIIT SRSMRVLGTL
Nprot   RLRSKKVLIV LDDIDNKDHY LEYLAGDLDW FGNGSRIIIT TRDKHLI...
PrfP    FLLTKRFLIL IDDVWDYKVW DNLCMCFSD. VSNRSRIILT TRLNDVAEYV
rps2    ALRQKRFLLL LDDVWEEIDL EKTGVPRPD. RENKCKVMFT TRSIALCNNM
```

Fig. 5A-1

```
       401                                                              450
L6pro  NEN.QCKLYE  VGSMSKPRSL  ELFSKHAFKK  NT....PPSY  YETLANDVVD
Nprot  .EK.NDIIYE  VTALPDHESI  QLFKQHAFGK  EV....PNEN  FEKLSLEVVN
PrfP   .KC.ESDPHH  LRLFRDDESW  TLLQKEVFQG  E....SCPPE  LEDVGFEISK
rps2   .GA.EYK.LR  VEFLEKKHAW  ELFCSKVWRK  DLLESSSIRR  LAEI...IVS 451         4                                                    500
L6pro  TTAGLPLTLK  VIGSLLFKQE  IAV..WEDTL  EQL....RRT  LNLDEVYDRL
Nprot  YAKGLPLALK  VWGSLLHNLR  LTE..WKSAI  EHM....KNN  .SYSGIIDNV
PrfP   SCRGLPLSVV  LVAGVLKQKK  KTLDSWKVVE  QSLS..SQRI  GSLEESISII
rps2   KCGGLPLALI  TLGGAMAH.R  ETEEEWIHAS  EVLTRFPAEM  KGMNYVFALL 501 5                   9                                        550
L6pro  KISYDALNPE  .AKEIFLDIA  CFFIGQ..NK  EEPYYMWTDC  NFYPASNIIF
Nprot  KISYDGLEPK  .QQEMFLDIA  CFLRGE..EK  DYILQILESC  HIGAEYGLRI
PrfP   GFSYKNL.PH  YLKPCFLYFG  GFLQGKDIHD  SKMTKLWVAE  EFVQANN...
rps2   KFSYDNLESD  LLRSCFLYCA  LFPEEHSIEI  EQLVEYWVGE  GFLTSSHGVN 551                                 10                           600
L6pro  LIQRCMIQVG  ........DD  DEFKMHDQLR  DMGREIVRRE  DVLPWKRSRI
Nprot  LIDKSLVFIS  ........EY  NQVQMHDLIQ  DMGKYIVNFQ  KD.PGERSRL
PrfP   ..........  ........EK  GQEDTRTRF.  .LGRSYW...  ..........
rps2   TIYKGYFLIG  DLKAACLLET  GDEKTQVKMH  NVVRSFALWM  ASEQGTYKEL 601                                                              650
L6pro  WSAEEGIDLL  LNKKGSSKVK  AISI.PWGVK  YEFK.SECFL  NLSELRYLHA
Nprot  WLAKEVEEVM  SNNTGTMAME  AIWVSSYSST  LRFS.NQAVK  NMKRLRVFNM
PrfP   ..........  ..........  ..........  ..........  ..........
rps2   ILVEPSMGHT  EAPKAENWRQ  ALVISLLDNR  IQTL.PEKLI  CPKLTTLMLQ 651                                                              700
L6pro  REAMLTGDFN  NLLPNLKWLE  LPFYKHGEDD  PPLTNYTMKN  LII.VILEHS
Nprot  GRSSTHYAID  YLPNNLRCFV  CTNYPW...E  SFPSTFELKM  LVH.LQLRH.
PrfP   ..........  ..........  ..........  ..........  ..........
rps2   QNSSLKKIPT  GFFMHPVLR   VLDLSF....  TSITEIPLSI  KYL.VELYHL 701                                                              750
L6pro  HITADDWGGW  RHMMKMAERL  KVVRLASNYS  LYGRRVR...  ..........
Nprot  .......NSL  RHLWTETKHL  PSL.......  ...RRID...  ..........
PrfP   ..........  ..........  ..........  ..........  ..........
rps2   SMSGTKISVL  PQELGNLRKL  KHLDLQRTQF  LQTIPRDAIC  WLSKLEVLNL 751                                                              800
L6pro  .LSD.CWRFP  KSIEVLSMTA  IEMDEVDIGE  LKKLKTLVLK  FCPIQKISGG
Nprot  .LSW.SKRLT  RTPDFTGPMN  LEY..VNLYQ  CSNLEEVHHS  LGCCSKVIGL
PrfP   ..........  ..........  ..........  ..........  ..........
rps2   YYSY.AGWEL  QSFGEDEAEE  LGFADLEYLE  NLTTLGITVL  SLETLKTLFE
```

Fig. 5A-2

```
        801                                                      850
L6pro   TFGMLKGLRE  L.CLEFNWGT  NLREVVADIG  QLSSLKVLKT  TGAKEVEINE
Nprot   YLNDCKSLKR  F.........  ..........  ..........  .PCVNVESLE
PrfP    ..........  ..........  ..........  ..........  ..........
rps2    FGALHKHIQH  L.HVEECNEL  LYFNLPSLTN  HGRNLRRLSI  KSCHDLEYLV 851                                                      900
L6pro   FPLGLK....  ...ELSTSSR  IPNLSQLLDL  EVLKVYDCKD  GFDMPPASPS
Nprot   Y.LGLR....  ...SCDSLEK  LPEIYGRMKP  EI........  QIHMQGSGIR
PrfP    ..........  ..........  ..........  ..........  ..........
rps2    TPADFENDWL  PSLEVLTLHS  LHNLTRVWGN  SVSQDCLRNI  RCINISHCNK 901                                                      950
L6pro   EDESSVWWKV  SKLKSLQLEK  TRINVNVVDD  ASSGGHLPRY  LLPTSLTYLK
Nprot   ELPSSIFQYK  THVTKLLL..  .WNMKNLVAL  PSSICRL...  ...KSLVSLS
PrfP    ..........  ..........  ..........  ..........  ..........
rps2    LKNVSWVQKL  PKLEVIELFD  CREIEELISE  HESPSVEDPT  LFP.SLKTLR 951                                                      1000
L6pro   IYQCTEPTWL  P.GIENLENL  TSLEVNDIFQ  TLGGDLDGLQ  GLRSLEILRI
Nprot   VSGCSKLESL  PEEIGDLDNL  RVFDASDTL.  ..........  ......ILRP
PrfP    ..........  ..........  ..........  ..........  ..........
rps2    TRDLPELNSI  LPSRFSFQKV  ETLVITNCPR  VKKLPFQERR  TQMNLPTVYC 1001                                                     1050
L6pro   RKVNGLARIK  GLKDLLCSST  CKLRKFYITE  CPDLIELLPC  ELGGQTVVVP
Nprot   P.........  .......SSI  IRLNKLIILM  FRGFKDGVHF  EFPPVAEGLH
PrfP    ..........  ..........  ..........  ..........  ..........
rps2    EEKWWKALEK  DQPNEELCYL  PRFVPN....  ..........  ..........

1051                                                     1100
L6pro   SMAELTIRDC  PRLEVGPMIR  SLPKFPMLKK  LDLAVANITK  EEDLDAIGSL
Nprot   SLEYLNL.SY  CNLIDGGLPE  EIGSLSSLKK  LDLSRNNF..  EHLPSSIAQL
PrfP    ..........  ..........  ..........  ..........  ..........
rps2    ..........  ..........  ..........  ..........  ..........

1101                                                     1150
L6pro   EELVSLELEL  DDTSSGIERI  VSSSKLQKLT  TLVVKVPSLR  EIEGLEELKS
Nprot   GALQSLDLK.  ..........  .DCQRLTQLP  ELPPELNELH  .VDCHMALKF
PrfP    ..........  ..........  ..........  ..........  ..........
rps2    ..........  ..........  ..........  ..........  ..........

1151                                                     1200
L6pro   LQDLYLEGCT  SLGRLPLEKL  KE......LD  IGGCPDLTEL  VQTVVAVPSL
Nprot   IHDL.VTKRK  KLHRVKLDDA  HNDTMYNLFA  YTMFQNISSM  RHDISASDSL
PrfP    ..........  ..........  ..........  ..........  ..........
rps2    ..........  ..........  ..........  ..........  ..........
```

Fig. 5A-3

```
       1201                                                    1250
L6pro  RGLTIRDCPR LEVGPMIQSL PKFPMLNELT LSMVNITKED ELEVLGSLEE
Nprot  .SLTV..... FTGQPYPEKI PSWFHHQGWD .SSVSVNLPE NWYIPDKFLG
 PrfP  .......... .......... .......... .......... ..........
 rps2  .......... .......... .......... .......... ..........

1251                                                    1300
L6pro  LD.SLELTLD DTCSSIERIS FLSKLQKLTT LIVEVPSLRE IEGLAELKSL
Nprot  FAVCYSRSLI DTTAHLIPVC .DDKMSRMTQ KLALSECDTE SSNYSEWD.I
 PrfP  .......... .......... .......... .......... ..........
 rps2  .......... .......... .......... .......... ..........

1301                                                    1350
L6pro  RILYL..... .......... .EGCTSLERL WPDQQQLGSL KNLNVLDIQG
Nprot  HFFFVPFAGL WDTSKANGKT PNDYGIIRLS FSGEEKMYGL RLLYKEGPEV
 PrfP  .......... .......... .......... .......... ..........
 rps2  .......... .......... .......... .......... ..........

1351                          1387
L6pro  CKSLSVDHLS ALKTTLPPRA RITWPDQPYR .......
Nprot  NALLQMRENS NEPTEHSTGI RRTQYNNRTS FYELING
 PrfP  .......... .......... .......... .......
 rps2  .......... .......... .......... .......
```

Fig. 5A-4

```
                      6
N     2 ASSSSSSSRWSYD VFLSFRG EDTRKTFTSHLYEVLNDKGIKTFQDDKRLEY  51
        ..|:|  ..  .|:|||||||.|||.||.||:|.    |.||.||.|
L6   51 NPSGSFPSVEYE VFLSFRG PDTREQFTDFLYQSLRRYKIMTFRDDDELLK 100

N    52 GATIPGELCKAIEESQFAIVVFSENYATSRWCLNELVKIMECK.TRFKQT 100
        |.|...:|  :||::|.:  :...::|..||.|:|||  ||..|:  .. ...
L6  101 GKEIGPNLLRAIDQSKIYVPIISSGYADSKWCLMELAEIVRRQEEDPRRI 150
                 7
N   101 VI PIFYDVDPS HVRNQKESFAKAFEEHETKYKDDVEGIQRWRIALNEAAN 150
        ::|||||  |||.|.||:|.:::  |||  .|..|:   |:.||.|:||...::
L6  151 IL PIFYMVDPS DVRHQTGCYKKAFRKHANKF..DGQTIQNWKDALKKVGD 198
                                                  .  8
N   151 LKGSCDNRDKTDADCIRQIVDQISSKLCKISLSY.LQNI VGIDTH LEKIE 199
        |||.  .::..::..  .: .:|.|.:|  |.  .   :::||||.||:. :
L6  199 LKGWHIGKNDKQGAIADKVSADIWSHISKENLILETDEL VGIDDH ITAVL 248

N   200 SLLEIGINGVRIMGIW GMGGVGKTTIARAIFDTLLGRMDSSYQFDGACFL 249
        .|..::  :.|  ::|:::|||||:|||||.|:|:::.:    ||:||..||:
L6  249 EKLSLDSENVTMVGLY GMGGIGKTTTAKAVYNKI.....SSC.FDCCCFI 292

N   250 KDIKE..NKRGMHSLQNALLSELLR...EKANYNNEEDGKHQMASRLRSK 294
        .:|:|   :|  |  :   ||.  |:||:||      :....||:.:|:. : .|:..
L6  293 DNIRETQEKDGVVVLQKKLVSEILRIDSGSVGFNNDSGGRKTIKERVSRF 342

N   295 KVLIVLDDIDNKDHYLEYLAGDLDWFGNGSRIIITTRDKHLI....EKND 340
        |:|:||||:|:|  ..: : |::. |::. |:::. ||||||.|..::: |..
L6  343 KILVVLDDVDEKFKFEDMLGSPKDFISQ.SRFIITSRSMRVLGTLNENQC 391

N   341 IIYEVTALPDHESIQLFKQHAFGKEVPNENFEKLSLEVVNYAKGLPLALK 390
        :|||..|...  |::||..||| |:.|  .:|.|.  :||:  .  ||||.||
L6  392 KLYEVGSMSKPRSLELFSKHAFKKNTPPSYYETLANDVVDTTAGLPLTLK 441

N   391 VWGSLLHNLRLTEWKSAIEHMKNN.SYSGIIDNVKISYDGLEPKQQEM FL 439
        ||||  . :. |...:|:::.. ...::.|:|||||||:|:...|:|| 
L6  442 VIGSLLFKQEIAVWEDTLEQLRRTLNLDEVYDRLKISYDALNPEAKEI FL 491
                 9
N   440 DIACF LRGEEKDYILQILESCHIGAEYGLRILIDKSLVFISEYNQVQ MHD 489
        |||||:  |::|:  . ::..|::  :.  .:|||:::::  :::  ::..|||
L6  492 DIACF FIGQNKEEPYYMWTDCNFYPASNIIFLIQRCMIQVGDDDEFK MHD 541
                10
N   490 LIQDMG KYIVNFQKD.PGERSRLWLAKEVEEVMSNNTGTMAMEAIWVSSY 538
        :.|||:||. ::. | .|||:|  |.|.  :::  |..|.  ..||.: ..:
L6  542 QLRDMG REIVRREDVLPWKRSRIWSAEEGIDLLLNKKGSSKVKAISI.PW 590
```

Fig. 5B-1

```
N    539 SSTLRFSNQAVKNMKRLRVFNMGRSSTHYAIDYLPNNLRCFVCTNYPW.. 586
         : .. |...:.. |:. || :: .    .:: |   ||: : .|.
L6   591 GVKYEFKSECFLNLSELRYLHAREAMLTGDFNNLLPNLKWLELPFYKHGE 640

N    587 .ESFPSTFELKMLVHLQLRH........NSLRHLWTETKHLPSL...... 621
         :.  ...::|  |: : | |        .:||:. ...:|.  :
L6   641 DDPPLTNYTMKNLIIVILEHSHITADDWGGWRHMMKMAERLKVVRLASNY 690

N    622 ....RRIDLSWSKRLTRTPDFTGMPNLEY..VNLYQCSNLEEVHHSLGCC 665
             ||: || :.|:..:. :. :|..:|   |:: :  ..|...:  .:...
L6   691 SLYGRRVRLSDCWRFPKSIEVLSMTAIEMDEVDIGELKKLKTLVLKFCPI 740

N    666 SKVIGLYLNDCKSLKRFPCVNVESLEYLGLRSCDSLEKLPEIYGRMKP.. 713
         |: |   :.  |:|: :          :|::.....|  .:... .|.:..
L6   741 QKISGGTFGMLKGLREL.........CLEFNWGTNLREVVADIGQLSSLK 781

N    714 ........EIQIHMQGSGIRELP.SSIFQYKTHVTKLLLWNM....KNLV 750
                 |::|: . |::||. || :.  .:: .| ::.:  ...:
L6   782 VLKTTGAKEVEINEFPLGLKELSTSSRIPNLSQLLDLEVLKVYDCKDGFD 831
                                       11
N    751 ALPSSICRLKSLVSLSVSGCSKLESLPEEIGDLDNLRVFDASDTLILRP. 799
         |.|  :   .|  |.:.|   |||.||  . |  .::   | |||..  |..
L6   832 MPPASPSEDESSVWWKV...SKLKSLQLEKTRINVNVVDDASSGGHLPRY 878

N    800 ..................PSSIIRLNKLIILMFRGFKDGVHFEFPPVAE 830
                           .:|  .|:.|. |  .|.   ::|.. :::.. :
L6   879 LLPTSLTYLKIYQCTEPTWLPGIENLENLTSLEVNDIFQTLGGDLDGL.Q 927
                  12
N    831 GLHSLEYLNLSYCNLID..GGLPEEI.GSLSSLKKLDL..SRNNFEHLPS 875
         ||:|||.|.:.. .| :.       ||.: : :| :.|:|: :   :.: :| ||:
L6   928 GLRSLEILRIRKVNGLARIKGLKDLLCSSTCKLRKFYITECPDLIELLPC 977

N    876 SIA....QLGALQSLDLKDCQRLTQLPELPPELNELHVDCHMALKFIHYL 921
         .::     :...:..|.::||.|| ::::  ...| .:..  || :...
L6   978 ELGGQTVVVPSMAELTIRDCPRL.EVGPMIRSLPKFPM.....LKKLDLA 1021

N    922 VTKRKKLHRVKLDDAHNDTMYNLFAYTMFQNISSMRHDISASDSLSLTVF 971
         |...|  ..:.   :.   ::  :    :...: :.  |:: : :|.|.  .||.:
L6   1022 VANITKEEDLDAIGSLEELV..SLELELDDTSSGIERIVSSSKLQKLTTL 1069

N    972 TGQPYPEKIPSWFHHQGWDSSVSVN.......LPENWYIPDKFLGFAVCY 1014
         ..   |:||: .:|::.  |:.        .  .:.  :| ::::.:.
L6   1070 VV.....KVPSLREIEGLEELKSLQDLYLEGCTSLGRLPLEKLKELDIGG 1114
```

Fig. 5B-2

```
N  1015 SRSLIDTTAHLIPVCDDK...........MSRMTQKLA....LSECDTES 1049
        :..|.:  .. :::|.. :         ::.|.|.|:    |.|  . .
L6 1115 CPDLTELVQTVVAVPSLRGLTIRDCPRLEVGPMIQSLPKFPMLNELTLSM 1164

N  1050 SNYSEWDIHFFFVPFAGLWDTSKANGKTPNDYGIIRLSFSGEEKMYGLRL 1099
        |... |    .:..:::|  . . . :.|.....: |.: :|  :|: .| :
L6 1165 VNITKEDELEVLGSLEELDSLELTLDDTCSSIERISF.LSKLQKLTTLIV 1213

N  1100 LYKEGPEVNALLQMRENSNEPTEHSTGIRRTQYNNRTSFYELIN 1143
        .. .|:::|  :::. .    |:|:: |   : :.  : .| |
L6 1214 EVPSLREIEGLAELKSLRILYLEGCTSLER.LWPDQQQLGSLKN 1256
```

Fig. 5B-3

```
                                                                                          -32  ACAAGTAAAACAAAGAGAGCGAGAAATCATCGAA           -1
ATGGATTTCATCTCATCTCTTATCGTTGGCTGTGTCGTGCTGCTGTCGTGTGTGCTCAGGTTGTTGTGTGCTCAGGTCGCTGTGATATAAGACTGATCTTAGACAAGCCATCACTGATCTTGAAACA  120
 M  D  F  I  S  S  L  I  V  G  C  A  Q  V  L  C  E  S  M  N  M  A  E  R  R  G  H  K  T  D  L  R  Q  A  I  T  D  L  E  T        40
                                                relatively hydrophobic
GCCATCGGTGACTTGAAGGCCATACGTGATGATGAGCTGACTTTACGATCCAACAGACGGTCTGAGGGACGAAGCTGCTCAAATCTGCCAGAGAGTGGCTTAGTGCGGTGCAAGTAACG  240
 A  I  G  D  L  K  A  I  R  D  D  L  T  L  R  I  Q  Q  D  G  L  E  G  R  S  C  S  N  R  A  R  E  W  L  S  A  V  Q  V  T        80
 leucine-zipper
GAGACTAAAACAGCCCTACTTTTAGTGAGGTTTAGGCGTTTGGGACGTCCGAATGAGGAGGAGGAGATACTCAGTTGTTCCGTTGTGCCGACTACAAACTGTCCAAGAAGGTTTCT  360
 E  T  K  T  A  L  L  L  V  R  F  R  R  R  E  Q  R  T  R  M  R  R  R  Y  L  S  C  F  G  C  A  D  Y  K  L  C  K  K  V  S       120
GCCATATTGAAGAGCATTGGTGAGCTGAGAGAACGCTCTGAGGCTATCAAAACTGACGGGGGTCAATTCAAGAACTTGTAGAGATACCCATCAAGTCCGTTGTCGGAAATACCACG  480
 A  I  L  K  S  I  G  E  L  R  E  R  S  E  A  I  K  T  D  G  G  S  I  Q  V  T  C  R  E  I  P  I  K  S  V  V  G  N  T  T       160
ATGATGGAACAGGTTTTGGAATTCTCAGTGAAGAAGAAGAAGAGGAATCATTGGTGTTTATGGACCTTGGTGGGGTTGGAAGACAACGTTAATGCAGAGCATTAACACGAGCTGATC  600
 M  M  E  Q  V  L  E  F  L  S  E  E  E  E  E  R  G  I  I  G  V  Y  G  P  G  G  V  G  K  T  T  L  M  Q  S  I  N  N  E  L  I    200
                                                                                          kinase-1a
ACAAAAGGACACATCAGTATGATGATGATGTCCTTATCATGGTCCAGATGTCAATTGGGTTCAAATGTCCAGAGTGTACAATTCAGCAACCGTTGAGCACCGTTGGGTTTATCTTGGGACGAGAAGGAGACC  720
 T  K  G  H  Q  Y  D  V  L  I  M  W  V  Q  M  S  R  E  F  G  E  C  T  I  Q  Q  A  V  G  A  R  L  G  L  S  W  D  E  K  E  T    240
GGCGAAACAGAGCTTTGAAGATATACAGAGCTTTGAGACACGAAACGTTTCTGTTGTTGCTAGATGATGTCTGGGAAGAAATAGACTTGGAGAAAACTGGAGTTCCTCGACCTGACAGG  840
 G  E  N  R  A  L  K  I  Y  R  A  L  R  Q  K  R  F  L  L  L  D  D  V  W  E  E  I  D  L  E  K  T  G  V  P  R  P  D  R         280
                                           kinase-2

Fig. 6A
```

```
GAAAACAAATGCAAGGTGATGTTCACGACACGGTCTATAGCATTATCCAACAATATGGGTGCGGAATACAAGTTGAGAGTTCTGGAGAAGAAACACGGCGTGGAGCTGTTCTGT   960
 E  N  K  C  K  V  M  F  T  T  R  S  I  A  L  C  N  N  M  G  A  E  Y  K  L  R  V  E  F  L  E  K  K  H  A  W  E  L  F  C   320

AGTAAGGTATGGAGAAAAGATCTTTTAGAGTCATCATCATCAATTCGCCCGGCTCGCGGAGATTATATGAGTAAATGTGGAGGATTGCCACTAGCGTTGATCACTTTAGGAGCCATGGCT  1080
 S  K  V  W  R  K  D  L  L  E  S  S  I  R  R  L  A  E  I  I  V  S  K  C  G  G  L  P  L  A  L  I  T  L  G  G  A  M  A   360
                        kinase-3a                         membrane integarated CATAGAGAGACAGAAGAGTGATCCATGCTAGTGAAGTTCTGACTAGATTTCCAGCAGAGATGAAGGGTATGAACTATGTATTTGCCCTTTTGAAATTCAGTTACGACAACCTCGAG  1200
 H  R  E  T  E  E  E  W  I  H  A  S  E  V  L  T  R  F  P  A  E  M  K  G  M  N  Y  V  F  A  L  L  K  F  S  Y  D  N  L  E   400

AGTGATCTGCTTCGGTCTTGTTTCTTGTACTGCGCTTTATTCCCAGAAGAACATTCTATAGAGATCAGCAGCTTGTGAGTACTGGGTCGCGAAGGGTTTCTCACCAGTCCCATGGC  1320
 S  D  L  L  R  S  C  F  L  Y  C  A  L  F  P  P  E  E  H  S  I  E  I  E  Q  L  V  E  Y  W  V  G  E  G  F  L  T  S  S  H  G   440

GTTAACACCATTTACAAGGGATATTTTCTCATTGGGGATCTGAAAGCGGCATGTTGTTGTGAAACCGGAGATGAGAAACACAGTGAAGATGCATAATGTGGTCAGAAGCTTTGCATTG  1440
 V  N  T  I  Y  K  G  Y  F  L  I  G  D  L  K  A  A  C  L  L  E  T  G  D  E  K  T  Q  V  K  M  H  N  V  V  R  S  F  A  L   480

TGGATGGCATCTGAACAGGGACTTATAAGGAGCTCATCCTAGTTGAGCCATGGACATACTGAAGCTCCTAAAGCAGAAAACTGGCCACAGGCGTTGGTCATCTCATTGTTAGAT  1560
 W  M  A  S  E  Q  G  T  Y  K  E  L  I  L  V  E  P  S  M  G  H  T  E  A  P  K  A  E  N  W  R  Q  A  L  V  I  S  L  L  D   520

AACAGAATCCAGACCTTGCCTGAAAAACTCATATGCCCGAAATTCCAAAGGTCTTCTTGATGCTCCAACAACTGTCCTTTTGAAGAAGATTCCAACAGGGTTTTTCATGCATATGCCTGTTCTC  1680
 N  R  I  Q  T  L  P  E  K  L  I  C  P  K  L  T  T  L  M  L  Q  Q  N  S  S  L  K  K  I  P  T  G  F  F  M  H  M  P  V  L   560

AGAGTCTTGGACTTGTCGTTCACAAGTATCACTGAGATTCCCGTTGTCATCAAGTATTTGGTCGAGTTGTATCATCTGTCTATGTCAGGAACAAAGATAAGTGTATTGCCACAGGAGCTT  1800
 R  V  L  D  L  S  F  T  S  I  T  E  I  P  L  S  I  K  Y  L  V  E  L  Y  H  L  S  M  S  G  T  K  I  S  V  L  P  Q  E  L   600
```

Fig. 6B

```
GGGAATCTTAGAAAACTGAAGCATCTGGACCACTACAAAGAACTCAGTTTCTTCAGACGATCCCAGAGATGCCATATGTTGGCTGAGCAAGCTCGAGTTCTGAACTTGTACTACAGTTAC   1920
 G  N  L  R  K  L  K  H  L  D  L  Q  R  T  Q  F  L  Q  T  I  P  R  D  A  I  C  W  L  S  K  L  E  V  L  N  L  Y  Y  S  Y     640

GCCGGTTGGGAACTCCAGAGCTTGGAGAAGATGAAGCAGAAGAAGAACTCGGATTCGCTGACTTGGAATACTTGGAAAACCTAACCACACTCGGTATCACTGTTCTCTCATTGGAGACCCTA   2040
 A  G  W  E  L  Q  S  L  E  K  M  K  Q  K  K  N  S  D  S  L  T  W  N  T  W  K  T  *  P  H  S  R  Y  H  C  S  H  W  R  P     680
```
(Amino acid row reading: A G W E L Q S L E K M K Q K K N S D S L T W N T W K T ... — reproduced best-effort)

Fig. 6C

```
GTTTATTGTGAGGAGAAATGGTGGAAAGCACTGGAAAAAGATCAACGAAAAGAGCTTTGTTATTTACCGCGCTTTGTTCCAAATTGATATAAGAGCACTCTGTACAAATA  2760
 V  Y  C  E  E  K  W  W  K  A  L  E  K  D  Q  P  N  E  E  L  C  Y  L  P  R  F  V  P  N  *                       909

TGTCCATTCATAAGTAGCAGGAAGCCAGGAAGGTTGTTCCAGTGAAGTCATCAACTTTCCACTAGACCACAAAACTAGAGATTATGTAATCATAAAAACCAAACTATCCGCGATCAAATA  2880

GATCTCACGACTATGAGGACCAAGACTCACCGAGTATCGTCGATATAGAAACTCCAAGCTCCAGTTCCGATCAGTGAAGACGAACAAGTTTATCAGATCTCTGCAACAATTCTGGGAATC  3000

GTCACCTCAGATTAGACCTCCAGTAAGAAGTGAGAAAGCATGGACGACGACTGTGAAGAATTGAGCTAATGAGCTGAACCGGATCCGGTGAAATTGCAGAACCGGATCGGAGAAGAAGAA  3120

TTTTGCATTTGTGCATCTTTATTTTTAATTGTTACGTTTGAGCCCCAATAATCATAGATATTGTAGTGAAGACCAAATTCATGGTGGATCAATCAAATTGTATTTCAAATTTTCGTAG  3240

TGTAATAACGGAAAAAGGAATAAAAGGTCACTGAGT (A)$_n$

Fig. 6D
```

| | | |
|---|---|---|
| consensus | PXXaXX LXXLXXLXaXXXX aXXa | |
| 505 | PKAENW RQALVISLLD NR IQTL | |
| 527 | PEKLIC PK LTTLMLQQNSSLKKI | |
| 550 | PTGFFMHMPVLRVLDLSFTS ITEI | |
| 574 | PLSIKY LVELYHLSMSGTK ISVL | |
| 597 | PQELGN LRKLKHLDLQRTQFLQTI | |
| 621 | PRDAICWLSKLEVLNLYYSYAGWEL | QSFGEDEAEELG |
| 658 | FADLEY LENLTTLGITVLS LETL | KT |
| 683 | LFEFGALHKHIQHLHVEECNELLYF | NL |
| 710 | P SLTNHGRNLRRLSIKSCHDLEYL | VT |
| 736 | PADFENDWLPSLEVLTLHSLHNLTRV | WGN |
| 765 | SVSQDC LRNIRCINISHCNKLKNV | SWVQKL |
| 795 | PK LEV IELFDCREIEELISEHES | PSVED |
| 823 | PT LFPSLKTLRTRDLPELNSI  L | |
| 845 | PSRFS  FQKVETLVITNCPRVKKL | |

Fig. 7

```
                                                Leucine zipper
                                               ─────────────────
MDFISSLIVG  CAQVLCESMN  MAERRGHKTD  LRQAITDLET  AIGDLKAIRD  DLTLRIQQDG   60
LEGRSCSNRA  REWLSAVQVT  ETKTALLLVR  FRRREQRTRM  RRYLSCFGC   ADYKLCKKVS  120
AILKSIGELR  ERSEAIKTDG  GSIQVTCREI  PIKSVVGNTT  MMEQVLEFLS  EEEERGIIGV  180
  P loop
─────────
YGPGGVGKTT  LMQSINNELI  TKGHQYDVLI  WVQMSREFGE  CTIQQAVGAR  LGLSWDEKET  240
GENRALKIYR  ALRQKRFLLL  LDDVWEEIDL  EKTGVPRPDR  ENKCKVMFTT  RSIALCNNMG  300
                                                    Membrane-spanning
                                                   ───────────────────
AEYKLRVEFL  EKKHAWELFC  SKVWRKDLLE  SSSIRRLAEI  IVSKCGGLPL  ALITLGGAMA  360
HRETEEEWIH  ASEVLTRFPA  EMKGMNYVFA  LLKFSYDNLE  SDLLRSCFLY  CALFPEEHSI  420
EIEQLVEYWV  GEGFLTSSHG  VNTIYKGYFL  IGDLKAACLL  ETGDEKTQVK  MHNVVRSFAL  480
WMASEQGTYK  ELILVEPSMG  HTEAPKAENW  RQALVISLLD  NRIQTLPEKL  ICPKLTTLML  540
                       ◁─── Leucine-rich repeats ───▷
QQNSSLKKIP  TGFFMHMPVL  RVLDLSFTSI  TEIPLSIKYL  VELYHLSMSG  TKISVLPQEL  600
GNLRKLKHLD  LQRTQFLQTI  PRDAICWLSK  LEVLNLYYSY  AGWELQSFGE  DEAEELGFAD  660
LEYLENLTTL  GITVLSLETL  KTLFEFGALH  KHIQHLHVEE  CNELLYFNLP  SLTNHGRNLR  720
RLSIKSCHDL  EYLVTPADFE  NDWLPSLEVL  TLHSLHNLTR  VWGNSVSQDC  LRNIRCINIS  780
 (end Leucine-rich repeats)
─────────────────────────────
HCNKLKNVSW  VQKLPKLEVI  ELFDCREIEE  LISEHESPSV  EDPTLFPSLK  TLRTRDLPEL  840
NSILPSRFSF  QKVETLVITN  CPRVKKLPFQ  ERRTQMNLPT  VYCEEKWWKA  LEKDQPNEEL  900
CYLPRFVPN   909
```

Fig. 8

```
      |   10       |   20       |   30       |   40       |   50       |   60
  1 aagctttaca gattggatga tctcttaatg catgctgaag tgactgcaaa aaggttagca   60
 61 atattcagtg gttctcgtta tgaatatttc atgaacggaa gcagcactga gaaaatgagg  120
121 cccttgttat ctgattttct gcaagagatt gagtctgtca aggtagagtt cagaaatgtt  180
181 tgcttgcaag ttctggatat atcaccttttt ccctgacag atggagaagg ccttgttaat  240
241 ttcttattaa aaaaccaggc caaggtgccg aatgatgatg ctgtttcttc tgatggaagt  300
301 ttagaggatg caagcagcac tgagaaaatg ggacttccat ctgattttct ccgagagatt  360
361 gagtctgttg agataaagga ggccagaaaa ttatatgatc aagtttttgga tgcaacacat  420
421 tgtgagacga gtaagcacga tggaaaaagc tttatcaaca ttatgttaac ccaacaggac  480
481 aaggtgctgg actatgatgc tggttcagtg tcttatcttc ttaaccaaat ctcagtagtt  540
541 aaagacaaaa tattgcacat tggctcttta cttgtagata ttgtacagta ccggaatatg  600
601 catatagaac ttacagatct cgctgaacgt gttcaagata aaaactacat tcgtttcttc  660
661 tctgtcaagg gttatattcc tgcttggtat tacacactat atctctctga tgtcaagcaa  720
721 ttgcttaagt ttgttgaggc agaggtaaag attatttgtc tgaaagtacc agattcttca  780
781 agttatagct tccctaagac aaatggatta ggatatctca attgcttttt aggcaaattg  840
841 gaggagcttt tacgttctaa gctcgatttg ataatcgact aaaacatca gattgaatca  900
901 gtcaaggagg gcttattgtg cctaagatca ttcattgatc attttttcaga aagctatgtt  960
961 gagcatgatg aagcttgtgg tcttatagca agagtttctg taatggcata caaggctgag 1020
1021 tatgtcattg actcatgctt ggcctattct catccactct ggtacaaagt tctttggatt 1080
1081 tctgaagttc ttgagaatat taagcttgta aataaagttg ttggggagac atgtgaaaga 1140
1141 aggaacactg aagttactgt gcatgaagtt gcaaagacta ccactaatgt agcaccatct 1200
1201 ttttcagctt atactcaaag agcaaacgaa gaaatggagg gttttcagga tacaatagat 1260
1261 gaattaaagg ataaactact tggaggatca cctgagcttg atgtcatctc aatcgttggc 1320
1321 atgccaggat tgggcaagac tacactagca aagaagattt acaatgatcc agaagtcacc 1380
1381 tctcgcttcg atgtccatgc tcaatgtgtt gtgactcaat tatattcatg gagagagttg 1440
1441 ttgctcacca ttttgaatga tgtgcttgag ccttctgatc gcaatgaaaa agaagatgga 1500
1501 gaaatagctg atgatctacg ccgattttttg ttgaccaaga gattcttgat tctcattgat 1560
1561 gatgtgtggg actataaagt gtgggacaat ctatgtatgt gcttcagtga tgtttcaaat 1620
1621 aggagtagaa ttatcctaac aacccgcttg aatgatgtcg ccgaatatgt caaatgtgaa 1680
1681 agtgatcccc atcatcttcg tttattcaga gatgacgaga gttggacatt attacagaaa 1740
1741 gaagtctttc aaggagagag ctgtccacct gaacttgaag atgtgggatt tgaaatatca 1800
1801 aaaagttgta gagggttgcc tctctcagtt gtgttagtag ctggtgttct gaaacagaaa 1860
1861 aagaagacac tagattcatg gaaagtagta gaacaaagtc taagttccca gaggattggc 1920
1921 agcttggaag agagcatatc tataattgga ttcagttaca agaatttacc acactatctt 1980
1981 aagccttgtt ttctctattt tggaggattt tgcagggaa aggatattca tgactcaaaa 2040
2041 atgaccaagt tgtgggtagc tgaagagttt gtacaagcaa caacgaaaa aggacaagaa 2100
2101 gatacccgca caaggtttct tggacgatct tattggtagg aatctggtga tggccatgga 2160
2161 gaagagacct aatgccaagg tgaaaacgtg ccgcattcat gatttgttgc ataaattctg 2220
2221 catggaaaag gccaaacaag aggatttcct tctccagatc aataggtaaa aaaaactgta 2280
2281 ttaattttac attacaaaaa aaaagaactg tattaatttt actgtattat gtttatgcca 2340
2341 actctcattt ccatgtgttc tcttttattc aattcagtgg agaaggtgta tttcctgaac 2400
2401 gattggaaga ataccgattg ttcgttcatt cttaccaaga tgaaattgat ctgtggcgcc 2460
2461 catctcgctc taatgtccgc tctttactat tcaatgcaat tgatccagat aacttgttat 2520
2521 ggccgcgtga tatctccttc atttttgaga gcttcaagct tgttaaagtg ttggatttgg 2580
```

Fig. 12A

```
2581 aatcattcaa cattggtggt acttttccca ttgaaacaca atatctaatt cagatgaagt 2640
2641 actttgcggc ccaaactgat gcaaattcaa ttccttcatc tatagctaag cttgaaaatc 2700
2701 ttgagacttt tgtcgtaaga ggattgggag gagagatgat attaccttgt tcacttctga 2760
2761 agatggtgaa attgaggcat atacatgtaa atgatcgggt ttcttttggt ttgcgtgaga 2820
2821 acatggatgt tttaactggt aactcacaat aacctaattt ggaaaccttt tctactccgc 2880
2881 gtctctttta tggtaaagac gcagagaaga ttttgaggaa gatgccaaaa ttgagaaaat 2940
2941 tgagttgcat attttcaggg acatttggtt attcaaggaa attgaagggt aggtgtgttc 3000
3001 gttttcccag attagatttt ctaagtcacc ttgagtccct caagctggtt tcgaacagct 3060
3061 atccagccaa acttcctcac aagttcaatt tcccctcgca actaagggaa ctgactttat 3120
3121 caaagttccg tctaccttgg acccaaattt cgatcattgc agaactgccc aacttggtga 3180
3181 ttcttaagtt attgctcaga gcctttgaag gggatcactg ggaagtgaaa gattcagagt 3240
3241 tcctagaact caaatactta aaactggaca acctcaaagt tgtacaatgg tccatctctg 3300
3301 atgatgcttt tcctaagctt gaacatttgg ttttaacgaa atgtaagcat cttgagaaaa 3360
3361 tcccttctcg ttttgaagat gctgtttgtc taaatagagt tgaggtgaac tggtgcaaact 3420
3421 ggaatgttgc caattcagcc caagatattc aaactatgca acatgaagtt atagcaaatg 3480
3481 attcattcac agttactata cagcctccag attggtctaa agaacagccc cttgactctt 3540
3541 agcaaaggtt tgttcttgct gtgttcatcc aagtgcattt aacatttatt cattttgttt 3600
3601 tacaccagaa catgtttatt ttgctagtat tacttgatac attaaaagaa atcgaactca 3660
3661 tatttctgct acagtcttaa cttttcttgg gcttacttga ggtctagatt agatcaatgg 3720
3721 ttcatgtaat ttttaattca ctgtttcatt caactgtctt atgatagttg tgaaatgaca 3780
3781 atattgttat ccctagccaa atttattatg ttcaaatgaa aactgatgtc acaactactt 3840
3841 ttttgtgaaa tgttttgaa ttttttgcta taaaattgac gaattgacag cttctatatt 3900
3901 tgtcagctaa actctttgtc accagaagtg tatttagaat tactgtggtt ttatgaaaga 3960
3961 gttctgtaga attttatgct tttgcagaat atagtttaaa acaacaacac ttctctgttt 4020
4021 cagagatagc agaagctaaa gttcaaggca ttttgtttat ttctagaaca agtggagttc 4080
4081 ttatgttgaa ttcttgaaaa gaagaagaat caggagcagg taaagttatc tcttttatg 4140
4141 ttttcttct tttagatgtt atttcttcat cttgaacgtg aacaccgctg aaagcatttt 4200
4201 aataaaaccg gagagaaaaa taagatcttt ttatataaag cattatcatg taaatatgcc 4260
4261 taaatccata tggtacaact gtttgacaaa atgatagaga ggggagtttt atagtataag 4320
4321 taaaacagga ttgagaaaaa aatccttgca cgattttcaa tttctggcca catcacaatg 4380
4381 tgtgtcaaag ttcccctctt taagtggaac aagcaatcag aaaagctcat tcttatcggt 4440
4441 gacataccaa taccagctga ctgtctcatc ttggttaact tagccttgct tacttagact 4500
4501 attagattag ttactaatga actggtaaat tggaaccaaa tgtagttagc ttgatgagct 4560
4561 ggtagacatg tatatatgaa gatacacgcg taactttagt cgatggttaa ttttcatttt 4620
4621 ttgatttttt ttcttcacag agtatatatg aacttggcct aaaagttttg cttcactaat 4680
4681 ttaactatta ccgtggatga acaagcatg gcaacatttt caacaactat cactcaagca 4740
4741 atgtaaaaaa tggaggttct acgagcggta catgtaagag ttttgtgcac acaagaggtt 4800
4801 ctgagacttg aaccatccat gtccaaggca gttgagatgc tagtaaagaa agaagaagat 4860
4861 gagcctgcac taattaatct ccctgtatga atgagagaat gagaaaaaga tggagcttca 4920
4921 tgaaccaaaa gttaccttt ttttttcttc ttaatggcat tactttgaag cacatgtttg 4980
4981 ttagttgtaa attgtaatgg tgaagtgttt gtaaatatag ggagtgatat ttgaaagaat 5040
5041 ggttgtgtta tcttacaaa ccggaatcat ttctgtataa ttttcttctg taattttttgg 5100
5101 tttcggttta ttcattactc atttcagtaa gctt                              5134
         |    10   |   20    |   30    |   40    |   50   |   60
```

Fig. 12B

SEQUENCE LISTING

<160> NUMBER OF SEQ ID NOS: 214

<210> SEQ ID NO 1
<211> LENGTH: 2903
<212> TYPE: DNA
<213> ORGANISM: Arabidopsis thaliana

<400> SEQUENCE: 1
aagtaaaaga aagagcgaga aatcatcgaa atggatttca tctcatctct tatcgttggc    60
tgtgctcagg tgttgtgtga atctatgaat atggcggaga gaagaggaca taagactgat   120
cttagacaag ccatcactga tcttgaaaca gccatcggtg acttgaaggc catacgtgat   180

-continued

| | |
|---|---|
| gacctgactt tacggatcca acaagacggt ctagagggac gaagctgctc aaatcgtgcc | 240 |
| agagagtggc ttagtgcggt gcaagtaacg gagactaaaa cagccctact tttagtgagg | 300 |
| tttaggcgtc gggaacagag gacgcgaatg aggaggagat acctcagttg tttcggttgt | 360 |
| gccgactaca aactgtgcaa gaaggtttct gccatattga agagcattgg tgagctgaga | 420 |
| gaacgctctg aagctatcaa acagatggc gggtcaattc aagtaacttg tagagagata | 480 |
| cccatcaagt ccgttgtcgg aaataccacg atgatggaac aggttttgga atttctcagt | 540 |
| gaagaagaag aaagaggaat cattggtgtt tatggacctg gtggggttgg aagacaacg | 600 |
| ttaatgcaga gcattaacaa cgagctgatc acaaaaggaa atcagtatga tgtactgatt | 660 |
| tgggttcaaa tgtccagaga attcggcgag tgtacaattc agcaagccgt tggagcacgg | 720 |
| ttgggtttat cttgggacga gaaggagacc ggcgaaaaca gagctttgaa gatatacaga | 780 |
| gctttgagac agaaacgttt cttgttgttg ctagatgatg tctgggaaga gatagacttg | 840 |
| gagaaaactg gagttcctcg acctgacagg gaaaacaaat gcaaggtgat gttcacgaca | 900 |
| cggtctatag cattatgcaa caatatgggt gcggaataca agttgagagt ggagtttctg | 960 |
| gagaagaaac acgcgtggga gctgttctgt agtaaggtat ggagaaaaga tcttttagag | 1020 |
| tcatcatcaa ttcgccggct cgcggagatt atagtgagta aatgtggagg attgccacta | 1080 |
| gcgttgatca ctttaggagg agccatggct catagagaga cagaagaaga gtggatccat | 1140 |
| gctagtgaag ttctgactag atttccagca gagatgaagg gtatgaacta tgtatttgcc | 1200 |
| cttttgaaat tcagctacga caacctcgag agtgatctgc ttcggtcttg tttcttgtac | 1260 |
| tgcgctttat tcccagaaga acattctata gagatcgagc agcttgttga gtactgggtc | 1320 |
| ggcgaagggt ttctcaccag ctcccatggc gttaacacca tttacaaggg atattttctc | 1380 |
| attggggatc tgaaagcggc atgtttgttg gaaaccggag atgagaaaac acaggtgaag | 1440 |
| atgcataatg tggtcagaag ctttgcattg tggatggcat ctgaacaggg gacttataag | 1500 |
| gagctgatcc tagttgagcc tagcatggga catactgaag ctcctaaagc agaaaactgg | 1560 |
| cgacaagcgt tggtgatctc attgttagat aacagaatcc agaccttgcc tgaaaaactc | 1620 |
| atatgcccga aactgacaac actgatgctc caacagaaca gctctttgaa gaagattcca | 1680 |
| acagggtttt tcatgcatat gcctgttctc agagtcttgg acttgtcgtt cacaagtatc | 1740 |
| actgagattc cgttgtctat caagtatttg gtggagttgt atcatctgtc tatgtcagga | 1800 |
| acaaagataa gtgtattgcc acaggagctt gggaatctta gaaaactgaa gcatctggac | 1860 |
| ctacaaagaa ctcagtttct tcagacgatc ccacgagatg ccatatgttg gctgagcaag | 1920 |
| ctcgaggttc tgaacttgta ctacagttac gccggttggg aactgcagag ctttggagaa | 1980 |
| gatgaagcag aagaactcgg attcgctgac ttggaatact tggaaaacct aaccacactc | 2040 |
| ggtatcactg ttctctcatt ggagacccta aaaactctct tcgagttcgg tgctttgcat | 2100 |
| aaacatatac agcatctcca cgttgaagag tgcaatgaac cctctactt caatctccca | 2160 |
| tcactcacta accatggcag gaacctgaga agacttagca ttaaaagttg ccatgacttg | 2220 |
| gagtacctgg tcacacccgc agattttgaa aatgattggc ttccgagtct agaggttctg | 2280 |
| acgttacaca gccttcacaa cttaaccaga gtgtgggaa attctgtaag ccaagattgt | 2340 |
| ctgcggaata tccgttgcat aaacatttca cactgcaaca agctgaagaa tgtctcatgg | 2400 |
| gttcagaaac tcccaaagct agaggtgatt gaactgttcg actgcagaga gatagaggaa | 2460 |
| ttgataagcg aacacgagag tccatccgtc gaagatccaa cattgttccc aagcctgaag | 2520 |
| accttgagaa ctagggatct gccagaacta aacagcatcc tcccatctcg attttcattc | 2580 |

-continued

```
caaaaagttg aaacattagt catcacaaat tgccccagag ttaagaaact gccgtttcag    2640
gagaggagga cccagatgaa cttgccaaca gtttattgtg aggagaaatg gtggaaagca    2700
ctggaaaaag atcaaccaaa cgaagagctt tgttatttac cgcgctttgt tccaaattga    2760
tataagagct aagagcactc tgtacaaata tgtccattca taagtagcag gaagccagga    2820
aggttgttcc agtgaagtca tcaactttcc acatagccac aaaactagag attatgtaat    2880
cataaaaacc aaactatccg cga                                            2903
```

<210> SEQ ID NO 2
<211> LENGTH: 885
<212> TYPE: PRT
<213> ORGANISM: Arabidopsis thaliana

<400> SEQUENCE: 2

```
Lys Lys Glu Arg Glu Ile Ile Glu Met Asp Phe Ile Ser Ser Leu Ile
 1               5                  10                  15

Val Gly Cys Ala Gln Val Leu Cys Glu Ser Met Asn Met Ala Glu Arg
            20                  25                  30

Arg Gly His Lys Thr Asp Leu Arg Gln Ala Ile Thr Asp Leu Arg Ile
        35                  40                  45

Gln Gln Asp Gly Leu Glu Gly Arg Ser Cys Ser Asn Arg Ala Arg Glu
    50                  55                  60

Trp Leu Ser Ala Val Gln Val Thr Glu Thr Lys Thr Ala Leu Leu Leu
65                  70                  75                  80

Val Arg Phe Arg Arg Glu Gln Arg Thr Arg Met Arg Arg Arg Tyr
                85                  90                  95

Leu Ser Cys Phe Gly Cys Ala Asp Tyr Lys Leu Cys Lys Lys Val Ser
            100                 105                 110

Ala Ile Leu Lys Ser Ile Gly Glu Leu Arg Glu Arg Ser Glu Ala Ile
        115                 120                 125

Lys Thr Asp Gly Gly Ser Ile Gln Val Thr Cys Arg Glu Ile Pro Ile
    130                 135                 140

Lys Ser Val Val Gly Asn Thr Thr Met Met Glu Gln Val Leu Glu Phe
145                 150                 155                 160

Leu Ser Glu Glu Glu Arg Gly Ile Ile Gly Val Tyr Gly Pro Gly
                165                 170                 175

Gly Val Gly Lys Thr Thr Leu Met Gln Ser Ile Asn Asn Glu Leu Ile
            180                 185                 190

Thr Lys Gly His Gln Tyr Asp Val Leu Ile Trp Val Gln Met Ser Arg
        195                 200                 205

Glu Phe Gly Glu Cys Thr Ile Gln Gln Ala Val Gly Ala Arg Leu Gly
    210                 215                 220

Leu Ser Trp Asp Glu Lys Glu Thr Gly Glu Asn Arg Ala Leu Lys Ile
225                 230                 235                 240

Tyr Arg Ala Leu Arg Gln Lys Arg Phe Leu Leu Leu Asp Asp Val
                245                 250                 255

Trp Glu Glu Ile Asp Leu Glu Lys Thr Gly Val Pro Arg Pro Asp Arg
            260                 265                 270

Glu Asn Lys Cys Lys Val Met Phe Thr Thr Arg Ser Ile Ala Leu Cys
        275                 280                 285

Asn Asn Met Gly Ala Glu Tyr Lys Leu Arg Val Glu Phe Leu Glu Lys
    290                 295                 300

Lys His Ala Trp Glu Leu Phe Cys Ser Lys Val Trp Arg Lys Asp Leu
```

-continued

```
            305                 310                 315                 320
Leu Glu Ser Ser Ser Ile Arg Arg Leu Ala Glu Ile Ile Val Ser Lys
                    325                 330                 335

Cys Gly Gly Leu Pro Leu Ala Leu Ile Thr Leu Gly Gly Ala Met Ala
                340                 345                 350

His Arg Glu Thr Glu Glu Trp Ile His Ala Ser Glu Val Leu Thr
            355                 360                 365

Arg Phe Pro Ala Glu Met Lys Gly Met Asn Tyr Val Phe Ala Leu Leu
        370                 375                 380

Lys Phe Ser Tyr Asp Asn Leu Glu Ser Asp Leu Leu Arg Ser Cys Phe
385                 390                 395                 400

Leu Tyr Cys Ala Leu Phe Pro Glu His Ser Ile Glu Ile Glu Gln
                405                 410                 415

Leu Val Glu Tyr Trp Val Gly Glu Phe Leu Thr Ser Ser His Gly
                420                 425                 430

Val Asn Thr Ile Tyr Lys Gly Tyr Phe Leu Ile Gly Asp Leu Lys Ala
                435                 440                 445

Ala Cys Leu Leu Glu Thr Gly Asp Glu Lys Thr Gln Val Lys Met His
450                 455                 460

Asn Val Val Arg Ser Phe Ala Leu Trp Met Ala Ser Glu Gln Gly Thr
465                 470                 475                 480

Tyr Lys Glu Leu Ile Leu Val Glu Pro Ser Met Gly His Thr Glu Ala
                485                 490                 495

Pro Lys Ala Glu Asn Trp Arg Gln Ala Leu Val Ile Ser Leu Leu Asp
                500                 505                 510

Asn Arg Ile Gln Thr Leu Pro Glu Lys Leu Ile Cys Pro Lys Leu Thr
            515                 520                 525

Thr Leu Met Leu Gln Gln Asn Ser Ser Leu Lys Lys Ile Pro Thr Gly
            530                 535                 540

Phe Phe Met His Met Pro Val Leu Arg Val Leu Asp Leu Ser Phe Thr
545                 550                 555                 560

Ser Ile Thr Glu Ile Pro Leu Ser Ile Lys Tyr Leu Val Glu Leu Tyr
                565                 570                 575

His Leu Ser Met Ser Gly Thr Lys Ile Ser Val Leu Pro Gln Glu Leu
                580                 585                 590

Gly Asn Leu Arg Lys Leu Lys His Leu Asp Leu Gln Arg Thr Gln Phe
            595                 600                 605

Leu Gln Thr Ile Pro Arg Asp Ala Ile Cys Trp Leu Ser Lys Leu Glu
        610                 615                 620

Val Leu Asn Leu Tyr Tyr Ser Tyr Ala Gly Trp Glu Leu Gln Ser Phe
625                 630                 635                 640

Gly Glu Asp Glu Ala Glu Glu Leu Gly Phe Ala Asp Leu Glu Tyr Leu
                645                 650                 655

Glu Asn Leu Thr Thr Leu Gly Ile Thr Val Leu Ser Leu Glu Thr Leu
            660                 665                 670

Lys Thr Leu Phe Glu Phe Gly Ala Leu His Lys His Ile Gln His Leu
        675                 680                 685

His Val Glu Glu Cys Asn Glu Leu Leu Tyr Phe Asn Leu Pro Ser Leu
        690                 695                 700

Thr Asn His Gly Arg Asn Leu Arg Arg Leu Ser Ile Lys Ser Cys His
705                 710                 715                 720

Asp Leu Glu Tyr Leu Val Thr Pro Ala Asp Phe Glu Asn Asp Trp Leu
                725                 730                 735
```

```
Pro Ser Leu Glu Val Leu Thr Leu His Ser Leu His Asn Leu Arg Cys
            740                 745                 750

Ile Asn Ile Ser His Cys Asn Lys Leu Lys Asn Val Ser Trp Val Gln
            755                 760                 765

Lys Leu Pro Lys Leu Glu Val Ile Glu Leu Phe Asp Cys Arg Glu Ile
            770                 775                 780

Glu Glu Leu Ile Ser Glu His Glu Ser Pro Ser Val Glu Asp Pro Thr
785                 790                 795                 800

Leu Phe Pro Ser Leu Lys Thr Leu Arg Thr Arg Asp Leu Pro Glu Leu
                805                 810                 815

Asn Ser Ile Leu Pro Ser Arg Phe Ser Phe Gln Lys Val Glu Thr Leu
                820                 825                 830

Val Ile Thr Asn Cys Pro Arg Val Lys Lys Leu Pro Phe Gln Glu Arg
                835                 840                 845

Arg Thr Gln Met Asn Leu Pro Thr Val Tyr Cys Glu Glu Lys Trp Trp
            850                 855                 860

Lys Ala Leu Glu Lys Asp Gln Pro Asn Glu Glu Leu Cys Tyr Leu Pro
865                 870                 875                 880

Arg Phe Val Pro Asn
                885

<210> SEQ ID NO 3
<211> LENGTH: 20
<212> TYPE: PRT
<213> ORGANISM: Arabidopsis thaliana

<400> SEQUENCE: 3

Glu His Ser Val Gln Ile Cys Pro Phe Ile Ser Ser Arg Lys Pro Gly
1               5                   10                  15

Arg Leu Phe Gln
            20

<210> SEQ ID NO 4
<211> LENGTH: 6
<212> TYPE: PRT
<213> ORGANISM: Arabidopsis thaliana

<400> SEQUENCE: 4

Ser His Gln Leu Ser Thr
1               5

<210> SEQ ID NO 5
<211> LENGTH: 11
<212> TYPE: PRT
<213> ORGANISM: Arabidopsis thaliana

<400> SEQUENCE: 5

Arg Leu Cys Asn His Lys Asn Gln Thr Ile Arg
1               5                   10

<210> SEQ ID NO 6
<211> LENGTH: 28
<212> TYPE: PRT
<213> ORGANISM: Arabidopsis thaliana

<400> SEQUENCE: 6

Ser Lys Arg Lys Ser Glu Lys Ser Ser Lys Trp Ile Ser Ser His Leu
1               5                   10                  15

Leu Ser Leu Ala Val Leu Arg Cys Cys Val Asn Leu
```

```
                   20                  25

<210> SEQ ID NO 7
<211> LENGTH: 25
<212> TYPE: PRT
<213> ORGANISM: Arabidopsis thaliana

<400> SEQUENCE: 7

Ile Trp Arg Arg Glu Glu Asp Ile Arg Leu Ile Leu Asp Lys Pro Ser
1               5                  10                  15

Leu Ile Leu Lys Gln Pro Ser Val Thr
            20                  25

<210> SEQ ID NO 8
<211> LENGTH: 6
<212> TYPE: PRT
<213> ORGANISM: Arabidopsis thaliana

<400> SEQUENCE: 8

Arg Pro Tyr Val Met Thr
1               5

<210> SEQ ID NO 9
<211> LENGTH: 8
<212> TYPE: PRT
<213> ORGANISM: Arabidopsis thaliana

<400> SEQUENCE: 9

Leu Tyr Gly Ser Asn Lys Thr Val
1               5

<210> SEQ ID NO 10
<211> LENGTH: 17
<212> TYPE: PRT
<213> ORGANISM: Arabidopsis thaliana

<400> SEQUENCE: 10

Arg Asp Glu Ala Ala Gln Ile Val Pro Glu Ser Gly Leu Val Arg Cys
1               5                  10                  15

Lys

<210> SEQ ID NO 11
<211> LENGTH: 8
<212> TYPE: PRT
<213> ORGANISM: Arabidopsis thaliana

<400> SEQUENCE: 11

Arg Arg Leu Lys Gln Pro Tyr Phe
1               5

<210> SEQ ID NO 12
<211> LENGTH: 10
<212> TYPE: PRT
<213> ORGANISM: Arabidopsis thaliana

<400> SEQUENCE: 12

Gly Leu Gly Val Gly Asn Arg Gly Arg Glu
1               5                  10

<210> SEQ ID NO 13
<211> LENGTH: 22
<212> TYPE: PRT
<213> ORGANISM: Arabidopsis thaliana
```

-continued

<400> SEQUENCE: 13

Gly Gly Asp Thr Ser Val Val Ser Val Val Pro Thr Thr Asn Cys Ala
1               5                   10                  15
Arg Arg Phe Leu Pro Tyr
            20

<210> SEQ ID NO 14
<211> LENGTH: 5
<212> TYPE: PRT
<213> ORGANISM: Arabidopsis thaliana

<400> SEQUENCE: 14

Arg Ala Leu Val Ser
1               5

<210> SEQ ID NO 15
<211> LENGTH: 15
<212> TYPE: PRT
<213> ORGANISM: Arabidopsis thaliana

<400> SEQUENCE: 15

Glu Asn Ala Leu Lys Leu Ser Lys Gln Met Ala Gly Gln Phe Lys
1               5                   10                  15

<210> SEQ ID NO 16
<211> LENGTH: 15
<212> TYPE: PRT
<213> ORGANISM: Arabidopsis thaliana

<400> SEQUENCE: 16

Leu Val Glu Arg Tyr Pro Ser Ser Pro Leu Ser Glu Ile Pro Arg
1               5                   10                  15

<210> SEQ ID NO 17
<211> LENGTH: 29
<212> TYPE: PRT
<213> ORGANISM: Arabidopsis thaliana

<400> SEQUENCE: 17

Trp Asn Arg Phe Trp Asn Phe Ser Val Lys Lys Lys Glu Glu Ser
1               5                   10                  15
Leu Val Phe Met Asp Leu Val Gly Leu Gly Arg Gln Arg
            20                  25

<210> SEQ ID NO 18
<211> LENGTH: 7
<212> TYPE: PRT
<213> ORGANISM: Arabidopsis thaliana

<400> SEQUENCE: 18

Cys Arg Ala Leu Thr Thr Ser
1               5

<210> SEQ ID NO 19
<211> LENGTH: 9
<212> TYPE: PRT
<213> ORGANISM: Arabidopsis thaliana

<400> SEQUENCE: 19

Ser Gln Lys Asp Ile Ser Met Met Tyr
1               5

<210> SEQ ID NO 20

```
<211> LENGTH: 36
<212> TYPE: PRT
<213> ORGANISM: Arabidopsis thaliana

<400> SEQUENCE: 20

Phe Gly Phe Lys Cys Pro Glu Asn Ser Ala Ser Val Gln Phe Ser Lys
 1               5                  10                  15

Pro Leu Glu His Gly Trp Val Tyr Leu Gly Thr Arg Arg Pro Ala
            20                  25                  30

Lys Thr Glu Leu
        35

<210> SEQ ID NO 21
<211> LENGTH: 5
<212> TYPE: PRT
<213> ORGANISM: Arabidopsis thaliana

<400> SEQUENCE: 21

Arg Tyr Thr Glu Leu
 1               5

<210> SEQ ID NO 22
<211> LENGTH: 8
<212> TYPE: PRT
<213> ORGANISM: Arabidopsis thaliana

<400> SEQUENCE: 22

Asp Arg Asn Val Ser Cys Cys Cys
 1               5

<210> SEQ ID NO 23
<211> LENGTH: 6
<212> TYPE: PRT
<213> ORGANISM: Arabidopsis thaliana

<400> SEQUENCE: 23

Met Met Ser Gly Lys Arg
 1               5

<210> SEQ ID NO 24
<211> LENGTH: 17
<212> TYPE: PRT
<213> ORGANISM: Arabidopsis thaliana

<400> SEQUENCE: 24

Thr Trp Arg Lys Leu Glu Phe Leu Asp Leu Thr Gly Lys Thr Asn Ala
 1               5                  10                  15

Arg

<210> SEQ ID NO 25
<211> LENGTH: 6
<212> TYPE: PRT
<213> ORGANISM: Arabidopsis thaliana

<400> SEQUENCE: 25

Cys Ser Arg His Gly Leu
 1               5

<210> SEQ ID NO 26
<211> LENGTH: 11
<212> TYPE: PRT
<213> ORGANISM: Arabidopsis thaliana

<400> SEQUENCE: 26
```

His Tyr Ala Thr Ile Trp Val Arg Asn Thr Ser
1               5                   10

<210> SEQ ID NO 27
<211> LENGTH: 23
<212> TYPE: PRT
<213> ORGANISM: Arabidopsis thaliana

<400> SEQUENCE: 27

Glu Trp Ser Phe Trp Arg Arg Asn Thr Arg Gly Ser Cys Ser Val Val
1               5                   10                  15

Arg Tyr Gly Glu Lys Ile Phe
            20

<210> SEQ ID NO 28
<211> LENGTH: 11
<212> TYPE: PRT
<213> ORGANISM: Arabidopsis thaliana

<400> SEQUENCE: 28

Ser His His Gln Phe Ala Gly Ser Arg Arg Leu
1               5                   10

<210> SEQ ID NO 29
<211> LENGTH: 7
<212> TYPE: PRT
<213> ORGANISM: Arabidopsis thaliana

<400> SEQUENCE: 29

Val Asn Val Glu Asp Cys His
1               5

<210> SEQ ID NO 30
<211> LENGTH: 19
<212> TYPE: PRT
<213> ORGANISM: Arabidopsis thaliana

<400> SEQUENCE: 30

Glu Glu Pro Trp Leu Ile Glu Arg Gln Lys Lys Ser Gly Ser Met Leu
1               5                   10                  15

Val Lys Phe

<210> SEQ ID NO 31
<211> LENGTH: 6
<212> TYPE: PRT
<213> ORGANISM: Arabidopsis thaliana

<400> SEQUENCE: 31

Leu Asp Phe Gln Gln Arg
1               5

<210> SEQ ID NO 32
<211> LENGTH: 6
<212> TYPE: PRT
<213> ORGANISM: Arabidopsis thaliana

<400> SEQUENCE: 32

Thr Met Tyr Leu Pro Phe
1               5

<210> SEQ ID NO 33
<211> LENGTH: 27
<212> TYPE: PRT

-continued

<213> ORGANISM: Arabidopsis thaliana

<400> SEQUENCE: 33

Asn Ser Ala Thr Thr Thr Ser Arg Val Ile Cys Phe Gly Leu Val Ser
1               5                   10                  15

Cys Thr Ala Leu Tyr Ser Gln Lys Asn Ile Leu
            20                  25

<210> SEQ ID NO 34
<211> LENGTH: 33
<212> TYPE: PRT
<213> ORGANISM: Arabidopsis thaliana

<400> SEQUENCE: 34

Arg Ser Ser Ser Leu Leu Ser Thr Gly Ser Ala Lys Gly Phe Ser Pro
1               5                   10                  15

Ala Pro Met Ala Leu Thr Pro Phe Thr Arg Asp Ile Phe Ser Leu Gly
            20                  25                  30

Ile

<210> SEQ ID NO 35
<211> LENGTH: 14
<212> TYPE: PRT
<213> ORGANISM: Arabidopsis thaliana

<400> SEQUENCE: 35

Lys Arg His Val Cys Trp Lys Pro Glu Met Arg Lys His Arg
1               5                   10

<210> SEQ ID NO 36
<211> LENGTH: 22
<212> TYPE: PRT
<213> ORGANISM: Arabidopsis thaliana

<400> SEQUENCE: 36

Arg Cys Ile Met Trp Ser Glu Ala Leu His Cys Gly Trp His Leu Asn
1               5                   10                  15

Arg Gly Leu Ile Arg Ser
            20

<210> SEQ ID NO 37
<211> LENGTH: 20
<212> TYPE: PRT
<213> ORGANISM: Arabidopsis thaliana

<400> SEQUENCE: 37

Leu Ser Leu Ala Trp Asp Ile Leu Lys Leu Leu Lys Gln Lys Thr Gly
1               5                   10                  15

Asp Lys Arg Trp
            20

<210> SEQ ID NO 38
<211> LENGTH: 15
<212> TYPE: PRT
<213> ORGANISM: Arabidopsis thaliana

<400> SEQUENCE: 38

Ile Thr Glu Ser Arg Pro Cys Leu Lys Asn Ser Tyr Ala Arg Asn
1               5                   10                  15

<210> SEQ ID NO 39
<211> LENGTH: 7

```
<212> TYPE: PRT
<213> ORGANISM: Arabidopsis thaliana

<400> SEQUENCE: 39

Cys Ser Asn Arg Thr Ala Leu
 1               5

<210> SEQ ID NO 40
<211> LENGTH: 46
<212> TYPE: PRT
<213> ORGANISM: Arabidopsis thaliana

<400> SEQUENCE: 40

Arg Arg Phe Gln Gln Gly Phe Ser Cys Ile Cys Leu Phe Ser Glu Ser
 1               5                  10                  15

Trp Thr Cys Arg Ser Gln Val Ser Leu Arg Phe Arg Cys Leu Ser Ser
                20                  25                  30

Ile Trp Trp Ser Cys Ile Ile Cys Leu Cys Gln Glu Gln Arg
            35                  40                  45

<210> SEQ ID NO 41
<211> LENGTH: 12
<212> TYPE: PRT
<213> ORGANISM: Arabidopsis thaliana

<400> SEQUENCE: 41

Val Tyr Cys His Arg Ser Leu Gly Ile Leu Glu Asn
 1               5                  10

<210> SEQ ID NO 42
<211> LENGTH: 21
<212> TYPE: PRT
<213> ORGANISM: Arabidopsis thaliana

<400> SEQUENCE: 42

Ser Ile Trp Thr Tyr Lys Glu Leu Ser Phe Phe Arg Arg Ser His Glu
 1               5                  10                  15

Met Pro Tyr Val Gly
            20

<210> SEQ ID NO 43
<211> LENGTH: 5
<212> TYPE: PRT
<213> ORGANISM: Arabidopsis thaliana

<400> SEQUENCE: 43

Ala Ser Ser Arg Phe
 1               5

<210> SEQ ID NO 44
<211> LENGTH: 32
<212> TYPE: PRT
<213> ORGANISM: Arabidopsis thaliana

<400> SEQUENCE: 44

Thr Cys Thr Thr Val Thr Pro Val Gly Asn Cys Arg Ala Leu Glu Lys
 1               5                  10                  15

Met Lys Gln Lys Asn Ser Asp Ser Leu Thr Trp Asn Thr Trp Lys Thr
                20                  25                  30

<210> SEQ ID NO 45
<211> LENGTH: 12
<212> TYPE: PRT
```

<213> ORGANISM: Arabidopsis thaliana

<400> SEQUENCE: 45

Pro His Ser Val Ser Leu Phe Ser His Trp Arg Pro
1               5                   10

<210> SEQ ID NO 46
<211> LENGTH: 38
<212> TYPE: PRT
<213> ORGANISM: Arabidopsis thaliana

<400> SEQUENCE: 46

Lys Leu Ser Ser Ser Val Leu Cys Ile Asn Ile Tyr Ser Ile Ser
1               5                   10                  15

Thr Leu Lys Ser Ala Met Asn Ser Ser Thr Ser Ile Ser His His Ser
            20                  25                  30

Leu Thr Met Ala Gly Thr
        35

<210> SEQ ID NO 47
<211> LENGTH: 27
<212> TYPE: PRT
<213> ORGANISM: Arabidopsis thaliana

<400> SEQUENCE: 47

Glu Asp Leu Ala Leu Lys Val Ala Met Thr Trp Ser Thr Trp Ser His
1               5                   10                  15

Pro Gln Ile Leu Lys Met Ile Gly Phe Arg Val
            20                  25

<210> SEQ ID NO 48
<211> LENGTH: 7
<212> TYPE: PRT
<213> ORGANISM: Arabidopsis thaliana

<400> SEQUENCE: 48

Arg Tyr Thr Ala Phe Thr Thr
1               5

<210> SEQ ID NO 49
<211> LENGTH: 7
<212> TYPE: PRT
<213> ORGANISM: Arabidopsis thaliana

<400> SEQUENCE: 49

Pro Glu Cys Gly Glu Ile Leu
1               5

<210> SEQ ID NO 50
<211> LENGTH: 10
<212> TYPE: PRT
<213> ORGANISM: Arabidopsis thaliana

<400> SEQUENCE: 50

Ala Lys Ile Val Cys Gly Ile Ser Val Ala
1               5                   10

<210> SEQ ID NO 51
<211> LENGTH: 7
<212> TYPE: PRT
<213> ORGANISM: Arabidopsis thaliana

<400> SEQUENCE: 51

Thr Phe His Thr Ala Thr Ser
1               5

<210> SEQ ID NO 52
<211> LENGTH: 6
<212> TYPE: PRT
<213> ORGANISM: Arabidopsis thaliana

<400> SEQUENCE: 52

Phe Arg Asn Ser Gln Ser
1               5

<210> SEQ ID NO 53
<211> LENGTH: 8
<212> TYPE: PRT
<213> ORGANISM: Arabidopsis thaliana

<400> SEQUENCE: 53

Leu Asn Cys Ser Thr Ala Glu Arg
1               5

<210> SEQ ID NO 54
<211> LENGTH: 16
<212> TYPE: PRT
<213> ORGANISM: Arabidopsis thaliana

<400> SEQUENCE: 54

Ala Asn Thr Arg Val His Pro Ser Lys Ile Gln His Cys Ser Gln Ala
1               5                   10                  15

<210> SEQ ID NO 55
<211> LENGTH: 7
<212> TYPE: PRT
<213> ORGANISM: Arabidopsis thaliana

<400> SEQUENCE: 55

Glu Leu Gly Ile Cys Gln Asn
1               5

<210> SEQ ID NO 56
<211> LENGTH: 15
<212> TYPE: PRT
<213> ORGANISM: Arabidopsis thaliana

<400> SEQUENCE: 56

Thr Ala Ser Ser His Leu Asp Phe His Ser Lys Lys Leu Lys His
1               5                   10                  15

<210> SEQ ID NO 57
<211> LENGTH: 19
<212> TYPE: PRT
<213> ORGANISM: Arabidopsis thaliana

<400> SEQUENCE: 57

Ser Ser Gln Ile Ala Pro Glu Leu Arg Asn Cys Arg Phe Arg Arg Gly
1               5                   10                  15

Gly Pro Arg

<210> SEQ ID NO 58
<211> LENGTH: 47
<212> TYPE: PRT
<213> ORGANISM: Arabidopsis thaliana

<400> SEQUENCE: 58

```
Thr Cys Gln Gln Phe Ile Val Arg Arg Asn Gly Gly Lys His Trp Lys
 1               5                  10                  15

Lys Ile Asn Gln Thr Lys Ser Phe Val Ile Tyr Arg Ala Leu Phe Gln
                20                  25                  30

Ile Asp Ile Arg Ala Lys Ser Thr Leu Tyr Lys Tyr Val His Ser
                35                  40                  45
```

<210> SEQ ID NO 59
<211> LENGTH: 33
<212> TYPE: PRT
<213> ORGANISM: Arabidopsis thaliana

<400> SEQUENCE: 59

```
Asp Ala Gly Ser Gln Glu Gly Cys Ser Ser Glu Val Ile Asn Phe Pro
 1               5                  10                  15

His Ser His Lys Thr Arg Asp Tyr Val Ile Ile Lys Thr Lys Leu Ser
                20                  25                  30

Ala
```

<210> SEQ ID NO 60
<211> LENGTH: 25
<212> TYPE: PRT
<213> ORGANISM: Arabidopsis thaliana

<400> SEQUENCE: 60

```
Val Lys Glu Arg Ala Arg Asn His Arg Asn Gly Phe His Leu Ile Ser
 1               5                  10                  15

Tyr Arg Trp Leu Cys Ser Gly Val Val
                20                  25
```

<210> SEQ ID NO 61
<211> LENGTH: 10
<212> TYPE: PRT
<213> ORGANISM: Arabidopsis thaliana

<400> SEQUENCE: 61

```
Ile Tyr Glu Tyr Gly Gly Glu Lys Arg Thr
 1               5                  10
```

<210> SEQ ID NO 62
<211> LENGTH: 5
<212> TYPE: PRT
<213> ORGANISM: Arabidopsis thaliana

<400> SEQUENCE: 62

```
Leu Glu Gly His Thr
 1               5
```

<210> SEQ ID NO 63
<211> LENGTH: 23
<212> TYPE: PRT
<213> ORGANISM: Arabidopsis thaliana

<400> SEQUENCE: 63

```
Pro Asp Phe Thr Asp Pro Thr Arg Arg Ser Arg Gly Thr Lys Leu Leu
 1               5                  10                  15

Lys Ser Cys Gln Arg Val Ala
                20
```

<210> SEQ ID NO 64
<211> LENGTH: 7
<212> TYPE: PRT

<210> SEQ ID NO 64
...

<400> SEQUENCE: 64

Cys Gly Ala Ser Asn Gly Asp
1               5

<210> SEQ ID NO 65
<211> LENGTH: 8
<212> TYPE: PRT
<213> ORGANISM: Arabidopsis thaliana

<400> SEQUENCE: 65

Asn Ser Pro Thr Phe Ser Glu Val
1               5

<210> SEQ ID NO 66
<211> LENGTH: 35
<212> TYPE: PRT
<213> ORGANISM: Arabidopsis thaliana

<400> SEQUENCE: 66

Ala Ser Gly Thr Glu Asp Ala Asn Glu Glu Ile Pro Gln Leu Phe
1               5                   10                  15

Arg Leu Cys Arg Leu Gln Thr Val Gln Glu Gly Phe Cys His Ile Glu
            20                  25                  30

Glu His Trp
        35

<210> SEQ ID NO 67
<211> LENGTH: 5
<212> TYPE: PRT
<213> ORGANISM: Arabidopsis thaliana

<400> SEQUENCE: 67

Ala Glu Arg Thr Leu
1               5

<210> SEQ ID NO 68
<211> LENGTH: 13
<212> TYPE: PRT
<213> ORGANISM: Arabidopsis thaliana

<400> SEQUENCE: 68

Ser Tyr Gln Asn Arg Trp Arg Val Asn Ser Ser Asn Leu
1               5                   10

<210> SEQ ID NO 69
<211> LENGTH: 22
<212> TYPE: PRT
<213> ORGANISM: Arabidopsis thaliana

<400> SEQUENCE: 69

Arg Asp Thr His Gln Val Arg Cys Arg Lys Tyr His Asp Asp Gly Thr
1               5                   10                  15

Gly Phe Gly Ile Ser Gln
            20

<210> SEQ ID NO 70
<211> LENGTH: 24
<212> TYPE: PRT
<213> ORGANISM: Arabidopsis thaliana

<400> SEQUENCE: 70

Arg Arg Arg Lys Arg Asn His Trp Cys Leu Trp Thr Trp Trp Gly Trp
1               5                   10                  15

Glu Asp Asn Val Asn Ala Glu His
            20

<210> SEQ ID NO 71
<211> LENGTH: 10
<212> TYPE: PRT
<213> ORGANISM: Arabidopsis thaliana

<400> SEQUENCE: 71

Gln Arg Ala Asp His Lys Arg Thr Ser Val
1               5                   10

<210> SEQ ID NO 72
<211> LENGTH: 55
<212> TYPE: PRT
<213> ORGANISM: Arabidopsis thaliana

<400> SEQUENCE: 72

Cys Thr Asp Leu Gly Ser Asn Val Gln Arg Ile Arg Arg Val Tyr Asn
1               5                   10                  15

Ser Ala Ser Arg Trp Ser Thr Val Gly Phe Ile Leu Gly Arg Glu Gly
            20                  25                  30

Asp Arg Arg Lys Gln Ser Phe Glu Asp Ile Gln Ser Phe Glu Thr Glu
        35                  40                  45

Thr Phe Leu Val Val Ala Arg
    50                  55

<210> SEQ ID NO 73
<211> LENGTH: 15
<212> TYPE: PRT
<213> ORGANISM: Arabidopsis thaliana

<400> SEQUENCE: 73

Cys Leu Gly Arg Asp Arg Leu Gly Glu Asn Trp Ser Ser Ser Thr
1               5                   10                  15

<210> SEQ ID NO 74
<211> LENGTH: 9
<212> TYPE: PRT
<213> ORGANISM: Arabidopsis thaliana

<400> SEQUENCE: 74

Arg Asp Arg Arg Arg Val Asp Pro Cys
1               5

<210> SEQ ID NO 75
<211> LENGTH: 41
<212> TYPE: PRT
<213> ORGANISM: Arabidopsis thaliana

<400> SEQUENCE: 75

Gln Gly Lys Gln Met Gln Gly Asp Val His Asp Thr Val Tyr Ser Ile
1               5                   10                  15

Met Gln Gln Tyr Gly Cys Gly Ile Gln Val Glu Ser Gly Val Ser Gly
            20                  25                  30

Glu Glu Thr Arg Val Gly Ala Val Leu
        35                  40

<210> SEQ ID NO 76
<211> LENGTH: 21

```
<212> TYPE: PRT
<213> ORGANISM: Arabidopsis thaliana

<400> SEQUENCE: 76

Gly Met Glu Lys Arg Ser Phe Arg Val Ile Ile Asn Ser Pro Ala Arg
 1               5                  10                  15
Gly Asp Tyr Ser Glu
            20

<210> SEQ ID NO 77
<211> LENGTH: 17
<212> TYPE: PRT
<213> ORGANISM: Arabidopsis thaliana

<400> SEQUENCE: 77

Met Trp Arg Ile Ala Thr Ser Val Asp His Phe Arg Arg Ser His Gly
 1               5                  10                  15
Ser

<210> SEQ ID NO 78
<211> LENGTH: 24
<212> TYPE: PRT
<213> ORGANISM: Arabidopsis thaliana

<400> SEQUENCE: 78

Ile Ser Ser Arg Asp Glu Gly Tyr Glu Leu Cys Ile Cys Pro Phe Glu
 1               5                  10                  15
Ile Gln Leu Arg Gln Pro Arg Glu
            20

<210> SEQ ID NO 79
<211> LENGTH: 24
<212> TYPE: PRT
<213> ORGANISM: Arabidopsis thaliana

<400> SEQUENCE: 79

Ser Ala Ser Val Leu Phe Leu Val Leu Arg Phe Ile Pro Arg Arg Thr
 1               5                  10                  15
Phe Tyr Arg Asp Arg Ala Ala Cys
            20

<210> SEQ ID NO 80
<211> LENGTH: 14
<212> TYPE: PRT
<213> ORGANISM: Arabidopsis thaliana

<400> SEQUENCE: 80

Val Leu Gly Arg Arg Val Ser His Gln Leu Pro Trp Arg
 1               5                  10

<210> SEQ ID NO 81
<211> LENGTH: 22
<212> TYPE: PRT
<213> ORGANISM: Arabidopsis thaliana

<400> SEQUENCE: 81

His His Leu Gln Gly Ile Phe Ser His Trp Gly Ser Glu Ser Gly Met
 1               5                  10                  15
Phe Val Gly Asn Arg Arg
            20

<210> SEQ ID NO 82
```

```
<211> LENGTH: 7
<212> TYPE: PRT
<213> ORGANISM: Arabidopsis thaliana

<400> SEQUENCE: 82

Glu Asn Thr Gly Glu Asp Ala
 1               5

<210> SEQ ID NO 83
<211> LENGTH: 43
<212> TYPE: PRT
<213> ORGANISM: Arabidopsis thaliana

<400> SEQUENCE: 83

Lys Thr His Met Pro Glu Thr Asp Asn Thr Asp Ala Pro Thr Glu Gly
 1               5                  10                  15

Leu Phe Glu Glu Asp Ser Asn Arg Val Phe His Ala Tyr Ala Cys Ser
            20                  25                  30

Gln Ser Leu Gly Leu Val Val His Lys Tyr His
        35                  40

<210> SEQ ID NO 84
<211> LENGTH: 11
<212> TYPE: PRT
<213> ORGANISM: Arabidopsis thaliana

<400> SEQUENCE: 84

Cys Gly Gln Lys Leu Cys Ile Val Asp Gly Ile
 1               5                  10

<210> SEQ ID NO 85
<211> LENGTH: 5
<212> TYPE: PRT
<213> ORGANISM: Arabidopsis thaliana

<400> SEQUENCE: 85

Gly Ala Asp Pro Ser
 1               5

<210> SEQ ID NO 86
<211> LENGTH: 14
<212> TYPE: PRT
<213> ORGANISM: Arabidopsis thaliana

<400> SEQUENCE: 86

Ser Arg Lys Leu Ala Thr Ser Val Gly Asp Leu Ile Val Arg
 1               5                  10

<210> SEQ ID NO 87
<211> LENGTH: 6
<212> TYPE: PRT
<213> ORGANISM: Arabidopsis thaliana

<400> SEQUENCE: 87

Gln Asn Pro Asp Leu Ala
 1               5

<210> SEQ ID NO 88
<211> LENGTH: 31
<212> TYPE: PRT
<213> ORGANISM: Arabidopsis thaliana

<400> SEQUENCE: 88

Asp Ser Val Val Tyr Gln Val Phe Gly Gly Val Val Ser Ser Val Tyr
```

```
                1               5                   10                  15
Val Arg Asn Lys Asp Lys Cys Ile Ala Thr Gly Ala Trp Glu Ser
                    20                  25                  30
```

<210> SEQ ID NO 89
<211> LENGTH: 47
<212> TYPE: PRT
<213> ORGANISM: Arabidopsis thaliana

<400> SEQUENCE: 89

```
Lys Thr Glu Ala Ser Gly Pro Thr Lys Asn Ser Val Ser Asp Asp
 1               5                   10                  15
Pro Thr Arg Cys His Met Leu Ala Glu Gln Ala Arg Gly Ser Glu Leu
                20                  25                  30
Val Leu Gln Leu Arg Arg Leu Gly Thr Ala Glu Leu Trp Arg Arg
            35                  40                  45
```

<210> SEQ ID NO 90
<211> LENGTH: 7
<212> TYPE: PRT
<213> ORGANISM: Arabidopsis thaliana

<400> SEQUENCE: 90

```
Ser Arg Arg Thr Arg Ile Arg
 1               5
```

<210> SEQ ID NO 91
<211> LENGTH: 30
<212> TYPE: PRT
<213> ORGANISM: Arabidopsis thaliana

<400> SEQUENCE: 91

```
Leu Gly Ile Leu Gly Lys Pro Asn His Thr Arg Tyr His Cys Ser Leu
 1               5                   10                  15
Ile Gly Asp Pro Lys Asn Ser Leu Arg Val Arg Cys Phe Ala
                20                  25                  30
```

<210> SEQ ID NO 92
<211> LENGTH: 7
<212> TYPE: PRT
<213> ORGANISM: Arabidopsis thaliana

<400> SEQUENCE: 92

```
Thr Tyr Thr Ala Ser Pro Arg
 1               5
```

<210> SEQ ID NO 93
<211> LENGTH: 10
<212> TYPE: PRT
<213> ORGANISM: Arabidopsis thaliana

<400> SEQUENCE: 93

```
Thr Pro Leu Leu Gln Ser Pro Ile Thr His
 1               5                   10
```

<210> SEQ ID NO 94
<211> LENGTH: 8
<212> TYPE: PRT
<213> ORGANISM: Arabidopsis thaliana

<400> SEQUENCE: 94

```
Pro Trp Gln Glu Pro Glu Lys Thr
 1               5
```

<210> SEQ ID NO 95
<211> LENGTH: 10
<212> TYPE: PRT
<213> ORGANISM: Arabidopsis thaliana

<400> SEQUENCE: 95

Leu Gly Val Pro Gly His Thr Arg Arg Phe
1               5                   10

<210> SEQ ID NO 96
<211> LENGTH: 58
<212> TYPE: PRT
<213> ORGANISM: Arabidopsis thaliana

<400> SEQUENCE: 96

Leu Ala Ser Glu Ser Arg Gly Ser Asp Val Thr Gln Pro Ser Gln Leu
1               5                   10                  15

Asn Gln Ser Val Gly Lys Phe Cys Lys Pro Arg Leu Ser Ala Glu Tyr
            20                  25                  30

Pro Leu His Lys His Phe Thr Leu Gln Gln Ala Glu Glu Cys Leu Met
        35                  40                  45

Gly Ser Glu Thr Pro Lys Ala Arg Gly Asp
    50                  55

<210> SEQ ID NO 97
<211> LENGTH: 33
<212> TYPE: PRT
<213> ORGANISM: Arabidopsis thaliana

<400> SEQUENCE: 97

Thr Val Arg Leu Gln Arg Asp Arg Gly Ile Asp Lys Arg Thr Arg Glu
1               5                   10                  15

Ser Ile Arg Arg Arg Ser Asn Ile Val Pro Lys Pro Glu Asp Leu Glu
            20                  25                  30

Asn

<210> SEQ ID NO 98
<211> LENGTH: 18
<212> TYPE: PRT
<213> ORGANISM: Arabidopsis thaliana

<400> SEQUENCE: 98

Gly Ser Ala Arg Thr Lys Gln His Pro Pro Ile Ser Ile Phe Ile Pro
1               5                   10                  15

Lys Ser

<210> SEQ ID NO 99
<211> LENGTH: 10
<212> TYPE: PRT
<213> ORGANISM: Arabidopsis thaliana

<400> SEQUENCE: 99

Asn Ile Ser His His Lys Leu Pro Gln Ser
1               5                   10

<210> SEQ ID NO 100
<211> LENGTH: 18
<212> TYPE: PRT
<213> ORGANISM: Arabidopsis thaliana

<400> SEQUENCE: 100

Glu Thr Ala Val Ser Gly Glu Glu Asp Pro Asp Glu Leu Ala Asn Ser
1               5                   10                  15

Leu Leu

<210> SEQ ID NO 101
<211> LENGTH: 4
<212> TYPE: PRT
<213> ORGANISM: Arabidopsis thaliana

<400> SEQUENCE: 101

Thr Ser His His
1

<210> SEQ ID NO 102
<211> LENGTH: 14
<212> TYPE: PRT
<213> ORGANISM: Arabidopsis thaliana

<400> SEQUENCE: 102

Glu Leu Arg Ala Leu Cys Thr Asn Met Ser Ile His Lys Met
1               5                   10

<210> SEQ ID NO 103
<211> LENGTH: 23
<212> TYPE: PRT
<213> ORGANISM: Arabidopsis thaliana

<400> SEQUENCE: 103

Gln Glu Ala Arg Lys Val Val Pro Val Lys Ser Ser Thr Phe His Ile
1               5                   10                  15

Ala Thr Lys Leu Glu Ile Met
            20

<210> SEQ ID NO 104
<211> LENGTH: 6
<212> TYPE: PRT
<213> ORGANISM: Arabidopsis thaliana

<400> SEQUENCE: 104

Lys Pro Asn Tyr Pro Arg
1               5

<210> SEQ ID NO 105
<211> LENGTH: 1491
<212> TYPE: DNA
<213> ORGANISM: Arabidopsis thaliana

<400> SEQUENCE: 105
atcgattgat ctctggctca gtgcgagtag tccatttgag agcagtcgta gccccgcgtg      60
gcgcatcatg gagctatttg gaattttcgc agggttatcg attcgtagtg ggaacccatt     120
cattgtttgg aaccaccaac ggacgactta acaagctccc cgaggtgcat gatgaaaatt     180
gctccagttg ccataaatca cagcccgctc agcagggagg tcccgtcaca cgcggcaccc     240
actcaggcaa agcaaaccaa ccttcaatct gaagctggcg atttagatgc aagaaaaagt     300
agcgcttcaa gcccggaaac ccgcgcatta ctcgctacta agacagtact cgggagacac     360
aagatagagg ttccggcctt tggagggtgg ttcaaaaaga atcatctaa gcacgagacg      420 ggcggttcaa gtgccaacgc agatagttcg agcgtggctt ccgattccac cgaaaaacct     480
ttgttccgtc tcacgcacgt tccttacgta tcccaaggta atgagcgaat gggatgttgg     540

-continued

```
tatgcctgcg caagaatggt tggccattct gtcgaagctg ggcctcgcct agggctgccg      600
gagctctatg agggaaggga ggcgccagct gggctacaag attttttcaga tgtagaaagg     660
tttattcaca atgaaggatt aactcgggta gaccttccag acaatgagag atttacacac    720
gaagagttgg gtgcactgtt gtataagcac gggccgatta tatttgggtg gaaaactccg    780
aatgacagct ggcacatgtc ggtcctcact ggtgtcgata agagacgtc gtccattact    840
tttcacgatc cccgacaggg gccggaccta gcaatgccgc tcgattactt taatcagcga    900
ttggcatggc aggttccaca cgcaatgctc taccgctaag tagcagggta tcttcacgtg    960
gcggcatcat gacaagccca tgatgccgcc agcagctacc tgaatgccgt ctggcttttt    020
ggtccctatt gtcgtatccg aagatgacg tcaaagaatc tcggcaagag ctttcttgct    080
cgactcctca gcttccggat cgatcaggtc gcttgccaga gcgcgcttgt ccatgagcat    140
ctgccacagc tgctggtcga tggtgtcctc agctaaaggg attttgacga caaccatgcg    200
caactgcccg ttgcgatacg ctcgatcctg aagccccggt gtccatggca gccccaagaa    260
aaagacatag ttcgccgctg tgaggttgta gcctgtgccg gcggccgacc tggtcccgat    320
aaacaccctg cagtccggat cctgctggaa agcatcaatc gccttctgcc gcttcttggg    380
cgagtcactg cccaccaacg tcacgcaccc gacgccaagc ttgaggcagt gctcccgcaa    440
cgtggccacg gattcctgat actcgcagaa gaggatcacc ttgtcgtcga c            491
```

<210> SEQ ID NO 106
<211> LENGTH: 255
<212> TYPE: PRT
<213> ORGANISM: Arabidopsis thaliana

<400> SEQUENCE: 106

```
Met Lys Ile Ala Pro Val Ala Ile Asn His Ser Pro Leu Ser Arg Glu
  1               5                  10                  15

Val Pro Ser His Ala Ala Pro Thr Gln Ala Lys Gln Thr Asn Leu Gln
             20                  25                  30

Ser Glu Ala Gly Asp Leu Asp Ala Arg Lys Ser Ser Ala Ser Ser Pro
         35                  40                  45

Glu Thr Arg Ala Leu Leu Ala Thr Lys Thr Val Leu Gly Arg His Lys
     50                  55                  60

Ile Glu Val Pro Ala Phe Gly Gly Trp Phe Lys Lys Ser Lys
 65                  70                  75                  80

His Glu Thr Gly Gly Ser Ser Ala Asn Ala Asp Ser Ser Ser Val Ala
                 85                  90                  95

Ser Asp Ser Thr Glu Lys Pro Leu Phe Arg Leu Thr His Val Pro Tyr
            100                 105                 110

Val Ser Gln Gly Asn Glu Arg Met Gly Cys Trp Tyr Ala Cys Ala Arg
        115                 120                 125

Met Val Gly His Ser Val Glu Ala Gly Pro Arg Leu Gly Leu Pro Glu
    130                 135                 140

Leu Tyr Glu Gly Arg Glu Ala Pro Ala Gly Leu Gln Asp Phe Ser Asp
145                 150                 155                 160

Val Glu Arg Phe Ile His Asn Glu Gly Leu Thr Arg Val Asp Leu Pro
                165                 170                 175

Asp Asn Glu Arg Phe Thr His Glu Leu Gly Ala Leu Leu Tyr Lys
            180                 185                 190

His Gly Pro Ile Ile Phe Gly Trp Lys Thr Pro Asn Asp Ser Trp His
        195                 200                 205
```

-continued

Met Ser Val Leu Thr Gly Val Asp Lys Glu Thr Ser Ser Ile Thr Phe
210                 215                 220

His Asp Pro Arg Gln Gly Pro Asp Leu Ala Met Pro Leu Asp Tyr Phe
225                 230                 235                 240

Asn Gln Arg Leu Ala Trp Gln Val Pro His Ala Met Leu Tyr Arg
            245                 250                 255

<210> SEQ ID NO 107
<211> LENGTH: 1258
<212> TYPE: PRT
<213> ORGANISM: Arabidopsis thaliana

<400> SEQUENCE: 107

Met Ser Tyr Leu Arg Glu Val Ala Thr Ala Val Ala Leu Leu Leu Pro
1               5                   10                  15

Phe Ile Leu Leu Asn Lys Phe Asn Arg Pro Asn Ser Lys Asp Ser Ile
            20                  25                  30

Val Asn Asp Asp Asp Ser Thr Ser Glu Val Asp Ala Ile Ser Asp
        35                  40                  45

Ser Thr Asn Pro Ser Gly Ser Phe Pro Ser Val Glu Tyr Glu Val Phe
50                  55                  60

Leu Ser Phe Arg Gly Pro Asp Thr Arg Glu Gln Phe Thr Asp Phe Leu
65                  70                  75                  80

Tyr Gln Ser Leu Arg Arg Tyr Lys Ile His Thr Phe Arg Asp Asp Asp
                85                  90                  95

Glu Leu Leu Lys Gly Lys Glu Ile Gly Pro Asn Leu Leu Arg Ala Ile
            100                 105                 110

Asp Gln Ser Lys Ile Tyr Val Pro Ile Ile Ser Ser Gly Tyr Ala Asp
        115                 120                 125

Ser Lys Trp Cys Leu Met Glu Leu Ala Glu Ile Val Arg Arg Gln Glu
130                 135                 140

Glu Asp Pro Arg Arg Ile Ile Leu Pro Ile Phe Tyr Met Val Asp Pro
145                 150                 155                 160

Ser Asp Val Arg His Gln Thr Gly Cys Tyr Lys Lys Ala Phe Arg Lys
                165                 170                 175

His Ala Asn Lys Phe Asp Gly Gln Thr Ile Gln Asn Trp Lys Asp Ala
            180                 185                 190

Leu Lys Lys Val Gly Asp Leu Lys Gly Trp His Ile Gly Lys Asn Asp
        195                 200                 205

Lys Gln Gly Ala Ile Ala Asp Lys Val Ser Ala Asp Ile Trp Ser His
210                 215                 220

Ile Ser Lys Glu Asn Leu Ile Leu Glu Thr Asp Glu Leu Val Gly Ile
225                 230                 235                 240

Asp Asp His Ile Thr Ala Val Leu Glu Lys Leu Ser Leu Asp Ser Glu
                245                 250                 255

Asn Val Thr Met Val Gly Leu Tyr Gly Met Gly Ile Gly Lys Thr
            260                 265                 270

Thr Thr Ala Lys Ala Val Tyr Asn Lys Ile Ser Ser Cys Phe Asp Cys
        275                 280                 285

Cys Cys Phe Ile Asp Asn Ile Arg Glu Thr Gln Glu Lys Asp Gly Val
    290                 295                 300

Val Val Leu Gln Lys Lys Leu Val Ser Glu Ile Leu Arg Ile Asp Ser
305                 310                 315                 320

Gly Ser Val Gly Phe Asn Asn Asp Ser Gly Gly Arg Lys Thr Ile Lys
                325                 330                 335

```
Glu Arg Val Ser Arg Phe Lys Ile Leu Val Leu Asp Asp Val Asp
            340                 345                 350

Glu Lys Phe Lys Phe Glu Asp Met Leu Gly Ser Pro Lys Asp Phe Ile
            355                 360                 365

Ser Gln Ser Arg Phe Ile Ile Thr Ser Arg Ser Met Arg Val Leu Gly
            370                 375                 380

Thr Leu Asn Glu Asn Gln Cys Lys Leu Tyr Glu Val Gly Ser Met Ser
385                 390                 395                 400

Lys Pro Arg Ser Leu Glu Leu Phe Ser Lys His Ala Phe Lys Lys Asn
            405                 410                 415

Thr Pro Pro Ser Ser Tyr Tyr Glu Thr Leu Ala Asn Asp Val Val Asp
            420                 425                 430

Thr Thr Ala Gly Leu Pro Leu Thr Leu Lys Val Ile Gly Ser Leu Leu
            435                 440                 445

Phe Lys Gln Glu Ile Ala Val Trp Glu Asp Thr Leu Glu Gln Leu Arg
            450                 455                 460

Arg Thr Leu Asn Leu Asp Glu Val Tyr Asp Arg Leu Lys Ile Ser Tyr
465                 470                 475                 480

Asp Ala Leu Asn Pro Glu Ala Lys Glu Ile Phe Leu Asp Ile Ala Cys
                    485                 490                 495

Phe Phe Ile Gly Gln Asn Lys Glu Glu Pro Tyr Tyr Met Trp Thr Asp
                500                 505                 510

Cys Asn Phe Tyr Pro Ala Ser Asn Ile Ile Phe Leu Ile Gln Arg Cys
            515                 520                 525

Met Ile Gln Val Gly Asp Asp Asp Glu Phe Lys Met His Asp Gln Leu
            530                 535                 540

Arg Asp Met Gly Arg Glu Ile Val Arg Arg Glu Asp Val Leu Pro Trp
545                 550                 555                 560

Lys Ser Arg Ile Trp Ser Ala Glu Gly Ile Asp Leu Leu Leu Asn
                565                 570                 575

Lys Arg Lys Gly Ser Ser Lys Val Lys Ala Ile Ser Ile Pro Trp Gly
            580                 585                 590

Val Lys Tyr Glu Phe Lys Ser Glu Cys Phe Leu Asn Leu Ser Glu Leu
            595                 600                 605

Arg Tyr Leu His Ala Arg Glu Ala Met Leu Thr Gly Asp Phe Asn Asn
            610                 615                 620

Leu Leu Pro Asn Leu Lys Trp Leu Glu Leu Pro Phe Tyr Lys His Gly
625                 630                 635                 640

Glu Asp Asp Pro Pro Leu Thr Asn Tyr Thr Met Lys Asn Leu Ile Ile
                    645                 650                 655

Val Ile Leu Glu His Ser His Ile Thr Ala Asp Asp Trp Gly Gly Trp
                660                 665                 670

Arg His Met Met Lys Met Ala Glu Arg Leu Lys Val Val Arg Leu Ala
            675                 680                 685

Ser Asn Tyr Ser Leu Tyr Gly Arg Arg Val Arg Leu Ser Asp Cys Trp
            690                 695                 700

Arg Phe Pro Lys Ser Ile Glu Val Leu Ser Met Thr Ala Ile Glu Met
705                 710                 715                 720

Asp Glu Val Asp Ile Gly Glu Leu Lys Lys Leu Lys Thr Leu Val Leu
                    725                 730                 735

Lys Pro Cys Pro Ile Gln Lys Ile Ser Gly Gly Thr Phe Gly Met Leu
                    740                 745                 750
```

-continued

```
Lys Gly Leu Arg Glu Leu Cys Leu Glu Phe Asn Trp Gly Thr Asn Leu
        755                 760                 765
Arg Glu Val Val Ala Asp Ile Gly Gln Leu Ser Ser Leu Lys Val Leu
        770                 775                 780
Lys Thr Gly Ala Lys Glu Val Glu Ile Asn Glu Phe Pro Leu Gly Leu
785                 790                 795                 800
Lys Thr Glu Leu Ser Thr Ser Ser Arg Ile Pro Asn Asn Leu Ser Gln
                805                 810                 815
Leu Leu Asp Leu Glu Val Leu Lys Val Tyr Asp Cys Lys Asp Gly Phe
                820                 825                 830
Asp Met Pro Pro Ala Ser Pro Ser Glu Asp Glu Ser Ser Val Trp Trp
        835                 840                 845
Lys Val Ser Lys Leu Lys Ser Leu Gln Leu Glu Lys Thr Arg Ile Asn
        850                 855                 860
Val Asn Val Val Asp Asp Ala Ser Ser Gly Gly His Leu Pro Arg Tyr
865                 870                 875                 880
Leu Leu Pro Thr Ser Leu Thr Tyr Leu Lys Ile Tyr Gln Cys Thr Glu
                885                 890                 895
Pro Thr Trp Leu Pro Gly Ile Glu Asn Leu Glu Asn Leu Thr Ser Leu
        900                 905                 910
Glu Val Asn Asp Ile Phe Gln Thr Leu Gly Gly Asp Leu Asp Gly Leu
        915                 920                 925
Gln Gly Leu Arg Ser Leu Glu Ile Leu Arg Ile Arg Lys Val Asn Gly
        930                 935                 940
Leu Ala Arg Ile Lys Gly Leu Lys Asp Leu Leu Cys Ser Ser Thr Cys
945                 950                 955                 960
Lys Leu Arg Lys Phe Tyr Ile Thr Glu Cys Pro Asp Leu Ile Glu Leu
                965                 970                 975
Leu Pro Cys Glu Leu Gly Val Gln Thr Val Val Pro Ser Met Ala
                980                 985                 990
Glu Leu Thr Ile Arg Asp Cys Pro Arg Leu Glu Val Gly Pro Met Ile
        995                 1000                1005
Arg Ser Leu Pro Lys Phe Pro Met Leu Lys Lys Leu Asp Leu Ala Val
        1010                1015                1020
Ala Asn Ile Thr Lys Glu Glu Asp Leu Asp Ala Ile Gly Ser Leu Glu
1025                1030                1035                1040
Glu Leu Val Ser Leu Glu Leu Glu Leu Asp Asp Thr Ser Ser Gly Ile
                1045                1050                1055
Glu Arg Ile Val Ser Ser Lys Leu Gln Lys Leu Thr Thr Leu Val
                1060                1065                1070
Val Lys Val Pro Ser Leu Arg Glu Ile Glu Gly Leu Glu Glu Leu Lys
        1075                1080                1085
Ser Leu Gln Asp Leu Tyr Leu Glu Gly Cys Thr Ser Leu Gly Arg Leu
        1090                1095                1100
Pro Leu Glu Lys Leu Lys Glu Leu Asp Ile Gly Gly Cys Pro Asp Leu
1105                1110                1115                1120
Thr Glu Leu Val Gln Thr Val Val Ala Val Pro Ser Leu Arg Gly Leu
                1125                1130                1135
Thr Ile Arg Asp Cys Pro Arg Leu Glu Val Gly Pro Met Ile Gln Ser
                1140                1145                1150
Leu Pro Lys Phe Pro Met Leu Asn Glu Leu Thr Leu Ser Met Val Asn
        1155                1160                1165
Ile Thr Lys Glu Asp Glu Leu Glu Val Leu Gly Ser Leu Glu Glu Leu
```

-continued

```
            1170                1175                1180
Asp Ser Leu Glu Leu Thr Leu Asp Asp Thr Cys Ser Ser Ile Glu Arg
1185                1190                1195                1200

Ile Ser Phe Leu Ser Lys Leu Gln Lys Leu Thr Thr Leu Ile Val Glu
                1205                1210                1215

Val Pro Ser Leu Arg Glu Ile Glu Gly Leu Ala Glu Leu Lys Ser Leu
                1220                1225                1230

Arg Ile Leu Tyr Leu Glu Gly Cys Thr Ser Leu Glu Arg Leu Trp Pro
                1235                1240                1245

Asp Gln Gln Gln Leu Gly Ser Leu Lys Asn
                1250                1255

<210> SEQ ID NO 108
<211> LENGTH: 1143
<212> TYPE: PRT
<213> ORGANISM: Arabidopsis thaliana

<400> SEQUENCE: 108

Met Ala Ser Ser Ser Ser Ser Arg Trp Ser Tyr Asp Val Phe Leu
1               5                   10                  15

Ser Phe Arg Gly Glu Asp Thr Arg Lys Thr Phe Thr Ser His Leu Tyr
                20                  25                  30

Glu Val Leu Asn Asp Lys Gly Ile Lys Thr Phe Gln Asp Asp Lys Arg
            35                  40                  45

Leu Glu Tyr Gly Ala Thr Ile Pro Gly Glu Leu Cys Lys Ala Ile Glu
        50                  55                  60

Glu Ser Gln Phe Ala Ile Val Val Phe Ser Glu Asn Tyr Ala Thr Ser
65                  70                  75                  80

Arg Trp Cys Leu Asn Glu Leu Val Lys Ile Met Glu Cys Lys Thr Arg
                85                  90                  95

Phe Lys Gln Thr Val Ile Pro Ile Phe Tyr Asp Val Asp Pro Ser His
                100                 105                 110

Val Arg Asn Gln Lys Glu Ser Phe Ala Lys Ala Phe Glu Glu His Glu
            115                 120                 125

Thr Lys Tyr Lys Asp Val Glu Gly Ile Gln Arg Trp Arg Ile Ala
        130                 135                 140

Leu Asn Glu Ala Ala Asn Leu Lys Gly Ser Cys Asp Asn Arg Asp Lys
145                 150                 155                 160

Thr Asp Ala Asp Cys Ile Arg Gln Ile Val Asp Gln Ile Ser Ser Lys
                165                 170                 175

Leu Cys Lys Ile Ser Leu Ser Tyr Leu Gln Asn Ile Val Gly Ile Asp
                180                 185                 190

Thr His Leu Glu Lys Ile Glu Ser Leu Leu Glu Ile Gly Ile Asn Gly
            195                 200                 205

Val Arg Ile Met Gly Ile Trp Gly Met Gly Gly Val Gly Lys Thr Thr
        210                 215                 220

Ile Ala Arg Ala Ile Phe Asp Thr Leu Leu Gly Arg Met Asp Ser Ser
225                 230                 235                 240

Tyr Gln Phe Asp Gly Ala Cys Phe Leu Lys Asp Ile Lys Glu Asn Lys
                245                 250                 255

Arg Gly Met His Ser Leu Gln Asn Ala Leu Leu Ser Glu Leu Leu Arg
                260                 265                 270

Glu Lys Ala Asn Tyr Asn Asn Glu Glu Asp Gly Lys His Gln Met Ala
            275                 280                 285
```

-continued

```
Ser Arg Leu Arg Ser Lys Lys Val Leu Ile Val Leu Asp Asp Ile Asp
        290                 295                 300

Asn Lys Asp His Tyr Leu Glu Tyr Leu Ala Gly Asp Leu Asp Trp Phe
305                 310                 315                 320

Gly Asn Gly Ser Arg Ile Ile Ile Thr Thr Arg Asp Lys His Leu Ile
                325                 330                 335

Glu Lys Asn Asp Ile Ile Tyr Glu Val Thr Ala Leu Pro Asp His Glu
            340                 345                 350

Ser Ile Gln Leu Phe Lys Gln His Ala Phe Gly Lys Glu Val Pro Asn
        355                 360                 365

Glu Asn Phe Glu Lys Leu Ser Leu Glu Val Val Asn Tyr Ala Lys Gly
    370                 375                 380

Leu Pro Leu Ala Leu Lys Val Trp Gly Ser Leu Leu His Asn Leu Arg
385                 390                 395                 400

Leu Thr Glu Trp Lys Ser Ala Ile Glu His Met Lys Asn Asn Ser Tyr
                405                 410                 415

Ser Gly Ile Ile Asp Lys Leu Lys Ile Ser Tyr Asp Gly Leu Glu Pro
            420                 425                 430

Lys Gln Gln Glu Met Phe Leu Asp Ile Ala Cys Phe Leu Arg Gly Glu
        435                 440                 445

Glu Lys Asp Tyr Ile Leu Gln Ile Leu Glu Ser Cys His Ile Gly Ala
    450                 455                 460

Glu Tyr Gly Leu Arg Ile Leu Ile Asp Lys Ser Leu Val Phe Ile Ser
465                 470                 475                 480

Glu Tyr Asn Gln Val Gln Met His Asp Leu Ile Gln Asp Met Gly Lys
                485                 490                 495

Tyr Ile Val Asn Phe Gln Lys Asp Pro Gly Glu Arg Ser Arg Leu Trp
            500                 505                 510

Leu Ala Lys Glu Val Glu Glu Val Met Ser Asn Asn Thr Gly Thr Met
        515                 520                 525

Ala Met Glu Ala Ile Trp Val Ser Ser Tyr Ser Ser Thr Leu Arg Phe
    530                 535                 540

Ser Asn Gln Ala Val Lys Asn Met Lys Arg Leu Arg Val Phe Asn Met
545                 550                 555                 560

Gly Arg Ser Ser Thr His Tyr Ala Ile Asp Tyr Leu Pro Asn Asn Leu
                565                 570                 575

Arg Cys Phe Val Cys Thr Asn Tyr Pro Trp Glu Ser Phe Pro Ser Thr
            580                 585                 590

Phe Glu Leu Lys Met Leu Val His Leu Gln Leu Arg His Asn Ser Leu
        595                 600                 605

Arg His Leu Trp Thr Glu Thr Lys His Leu Pro Ser Leu Arg Arg Ile
    610                 615                 620

Asp Leu Ser Trp Ser Lys Arg Leu Thr Arg Thr Pro Asp Phe Thr Gly
625                 630                 635                 640

Met Pro Asn Leu Glu Tyr Val Asn Leu Tyr Gln Cys Ser Asn Leu Glu
                645                 650                 655

Glu Val His His Ser Leu Gly Cys Cys Ser Lys Val Ile Gly Leu Tyr
            660                 665                 670

Leu Asn Asp Cys Lys Ser Leu Lys Arg Phe Pro Cys Val Asn Val Glu
        675                 680                 685

Ser Leu Glu Tyr Leu Gly Leu Arg Ser Cys Asp Ser Leu Glu Lys Leu
    690                 695                 700

Pro Glu Ile Tyr Gly Arg Met Lys Pro Glu Ile Gln Ile His Met Gln
```

-continued

```
            705                 710                 715                 720
Gly Ser Gly Ile Arg Glu Leu Pro Ser Ser Ile Phe Gln Tyr Lys Thr
                725                 730                 735
His Val Thr Lys Leu Leu Leu Trp Asn Met Lys Asn Leu Val Ala Leu
                740                 745                 750
Pro Ser Ser Ile Cys Arg Leu Lys Ser Leu Val Ser Leu Ser Val Ser
                755                 760                 765
Gly Cys Ser Lys Leu Glu Ser Leu Pro Glu Glu Ile Gly Asp Leu Asp
                770                 775                 780
Asn Leu Arg Val Phe Asp Ala Ser Asp Thr Leu Ile Leu Arg Pro Pro
785                 790                 795                 800
Ser Ser Ile Ile Arg Leu Asn Lys Leu Ile Ile Leu Met Phe Arg Gly
                805                 810                 815
Phe Lys Asp Gly Val His Phe Glu Phe Pro Pro Val Ala Glu Gly Leu
                820                 825                 830
His Ser Leu Glu Tyr Leu Asn Leu Ser Tyr Cys Asn Leu Ile Asp Gly
                835                 840                 845
Gly Leu Pro Glu Glu Ile Gly Ser Leu Ser Ser Leu Lys Lys Leu Asp
                850                 855                 860
Leu Ser Arg Asn Asn Phe Glu His Leu Pro Ser Ser Ile Ala Gln Leu
865                 870                 875                 880
Gly Ala Leu Gln Ser Leu Asp Leu Lys Asp Cys Gln Arg Leu Thr Gln
                885                 890                 895
Leu Pro Glu Leu Pro Glu Leu Asn Glu Leu His Val Asp Cys His
                900                 905                 910
Met Ala Leu Lys Phe Ile His Tyr Leu Val Thr Lys Arg Lys Lys Leu
                915                 920                 925
His Arg Val Lys Leu Asp Asp Ala His Asn Asp Thr Met Tyr Asn Leu
                930                 935                 940
Phe Ala Tyr Thr Met Phe Gln Asn Ile Ser Ser Met Arg His Asp Ile
945                 950                 955                 960
Ser Ala Ser Asp Ser Leu Ser Leu Thr Val Phe Thr Gly Gln Pro Tyr
                965                 970                 975
Pro Glu Lys Ile Pro Ser Trp Phe His His Gln Gly Trp Asp Ser Ser
                980                 985                 990
Val Ser Val Asn Leu Pro Glu Asn Trp Tyr Ile Pro Asp Lys Phe Leu
                995                 1000                1005
Gly Phe Ala Val Cys Tyr Ser Arg Ser Leu Ile Asp Thr Thr Ala His
                1010                1015                1020
Leu Ile Pro Val Cys Asp Asp Lys Met Ser Arg Met Thr Gln Lys Leu
1025                1030                1035                1040
Ala Leu Ser Glu Cys Asp Thr Glu Ser Ser Asn Tyr Ser Glu Trp Asp
                1045                1050                1055
Ile His Phe Phe Phe Val Pro Phe Ala Gly Leu Trp Asp Thr Ser Lys
                1060                1065                1070
Ala Asn Gly Lys Thr Pro Asn Asp Tyr Gly Ile Arg Leu Ser Phe
                1075                1080                1085
Ser Gly Glu Glu Lys Met Tyr Gly Arg Leu Arg Leu Tyr Lys Glu Gly
                1090                1095                1100
Pro Glu Val Asn Ala Leu Leu Gln Met Arg Glu Asn Ser Asn Glu Pro
1105                1110                1115                1120
Thr Glu His Ser Thr Gly Ile Arg Arg Thr Gln Tyr Asn Asn Arg Thr
                1125                1130                1135
```

```
Ser Phe Tyr Glu Leu Ile Asn
            1140

<210> SEQ ID NO 109
<211> LENGTH: 429
<212> TYPE: PRT
<213> ORGANISM: Arabidopsis thaliana

<400> SEQUENCE: 109

Leu Arg Ser Lys Leu Asp Leu Ile Ile Asp Leu Lys His Gln Ile Glu
 1               5                  10                  15

Ser Val Lys Glu Gly Leu Leu Cys Leu Arg Ser Phe Ile Asp His Phe
                20                  25                  30

Ser Glu Ser Tyr Val Glu His Asp Glu Ala Cys Gly Leu Ile Ala Arg
            35                  40                  45

Val Ser Val Met Ala Tyr Lys Ala Glu Tyr Val Ile Asp Ser Cys Leu
 50                  55                  60

Ala Tyr Ser His Pro Leu Trp Tyr Lys Val Leu Trp Ile Ser Glu Val
 65                  70                  75                  80

Leu Glu Asn Ile Lys Leu Val Asn Lys Val Gly Glu Thr Cys Glu
                85                  90                  95

Arg Arg Asn Thr Glu Val Thr Val His Glu Val Ala Lys Thr Thr Thr
            100                 105                 110

Asn Val Ala Pro Ser Phe Ser Ala Tyr Thr Gln Arg Ala Asn Glu Glu
        115                 120                 125

Met Glu Gly Phe Gln Asp Thr Ile Asp Glu Leu Lys Asp Lys Leu Leu
130                 135                 140

Gly Gly Ser Pro Glu Leu Asp Val Ile Ser Ile Val Gly Met Pro Gly
145                 150                 155                 160

Leu Gly Lys Thr Thr Leu Ala Lys Lys Ile Tyr Asn Asp Pro Glu Val
                165                 170                 175

Thr Ser Arg Phe Asp Val His Ala Gln Cys Val Val Thr Gln Leu Tyr
            180                 185                 190

Ser Trp Arg Glu Leu Leu Leu Thr Ile Leu Asn Asp Val Leu Glu Pro
        195                 200                 205

Ser Asp Arg Asn Glu Lys Glu Asp Gly Glu Ile Ala Asp Glu Leu Arg
210                 215                 220

Arg Phe Leu Leu Thr Lys Arg Phe Leu Ile Leu Ile Asp Asp Val Trp
225                 230                 235                 240

Asp Tyr Lys Val Trp Asp Asn Leu Cys Met Cys Phe Ser Asp Val Ser
                245                 250                 255

Asn Arg Ser Arg Ile Ile Leu Thr Thr Arg Leu Asn Asp Val Ala Glu
            260                 265                 270

Tyr Val Lys Cys Glu Ser Asp Pro His His Leu Arg Leu Phe Arg Asp
        275                 280                 285

Asp Glu Ser Trp Thr Leu Leu Gln Lys Glu Val Phe Gln Gly Glu Ser
290                 295                 300

Cys Pro Pro Glu Leu Glu Asp Val Gly Phe Glu Ile Ser Lys Ser Cys
305                 310                 315                 320

Arg Gly Leu Pro Leu Ser Val Val Leu Ala Gly Val Leu Lys Gln
                325                 330                 335

Lys Lys Lys Thr Leu Asp Ser Trp Lys Val Val Glu Gln Ser Leu Ser
            340                 345                 350

Ser Gln Arg Ile Gly Ser Leu Glu Glu Ser Ile Ser Ile Ile Gly Phe
```

-continued

```
                    355                 360                 365
Ser Tyr Lys Asn Leu Pro His Tyr Leu Lys Pro Cys Phe Leu Tyr Phe
        370                 375                 380
Gly Gly Phe Leu Gln Gly Lys Asp Ile His Asp Ser Lys Met Thr Lys
385                 390                 395                 400
Leu Trp Val Ala Glu Glu Phe Val Gln Ala Asn Asn Glu Lys Gly Gln
                405                 410                 415
Glu Asp Thr Arg Thr Arg Phe Leu Gly Arg Ser Tyr Trp
                420                 425

<210> SEQ ID NO 110
<211> LENGTH: 11
<212> TYPE: PRT
<213> ORGANISM: Arabidopsis thaliana

<400> SEQUENCE: 110

Gly Met Gly Gly Ile Gly Lys Thr Thr Thr Ala
1               5                   10

<210> SEQ ID NO 111
<211> LENGTH: 11
<212> TYPE: PRT
<213> ORGANISM: Arabidopsis thaliana

<400> SEQUENCE: 111

Gly Met Gly Gly Val Gly Lys Thr Thr Ile Ala
1               5                   10

<210> SEQ ID NO 112
<211> LENGTH: 11
<212> TYPE: PRT
<213> ORGANISM: Arabidopsis thaliana

<400> SEQUENCE: 112

Gly Met Pro Gly Leu Gly Lys Thr Thr Leu Ala
1               5                   10

<210> SEQ ID NO 113
<211> LENGTH: 11
<212> TYPE: PRT
<213> ORGANISM: Arabidopsis thaliana

<400> SEQUENCE: 113

Gly Pro Gly Gly Val Gly Lys Thr Thr Leu Met
1               5                   10

<210> SEQ ID NO 114
<211> LENGTH: 11
<212> TYPE: PRT
<213> ORGANISM: Arabidopsis thaliana

<400> SEQUENCE: 114

Phe Lys Ile Leu Val Val Leu Asp Asp Val Asp
1               5                   10

<210> SEQ ID NO 115
<211> LENGTH: 11
<212> TYPE: PRT
<213> ORGANISM: Arabidopsis thaliana

<400> SEQUENCE: 115

Lys Lys Val Leu Ile Val Leu Asp Asp Ile Asp
1               5                   10
```

<210> SEQ ID NO 116
<211> LENGTH: 11
<212> TYPE: PRT
<213> ORGANISM: Arabidopsis thaliana

<400> SEQUENCE: 116

Lys Arg Phe Leu Ile Leu Ile Asp Asp Val Trp
1               5                   10

<210> SEQ ID NO 117
<211> LENGTH: 11
<212> TYPE: PRT
<213> ORGANISM: Arabidopsis thaliana

<400> SEQUENCE: 117

Lys Arg Phe Leu Leu Leu Leu Asp Asp Val Trp
1               5                   10

<210> SEQ ID NO 118
<211> LENGTH: 8
<212> TYPE: PRT
<213> ORGANISM: Arabidopsis thaliana

<400> SEQUENCE: 118

Ser Arg Phe Ile Ile Thr Ser Arg
1               5

<210> SEQ ID NO 119
<211> LENGTH: 8
<212> TYPE: PRT
<213> ORGANISM: Arabidopsis thaliana

<400> SEQUENCE: 119

Ser Arg Ile Ile Ile Thr Thr Arg
1               5

<210> SEQ ID NO 120
<211> LENGTH: 8
<212> TYPE: PRT
<213> ORGANISM: Arabidopsis thaliana

<400> SEQUENCE: 120

Ser Arg Ile Ile Leu Thr Thr Arg
1               5

<210> SEQ ID NO 121
<211> LENGTH: 8
<212> TYPE: PRT
<213> ORGANISM: Arabidopsis thaliana

<400> SEQUENCE: 121

Cys Lys Val Met Phe Thr Thr Arg
1               5

<210> SEQ ID NO 122
<211> LENGTH: 8
<212> TYPE: PRT
<213> ORGANISM: Arabidopsis thaliana

<400> SEQUENCE: 122

Gly Leu Pro Leu Thr Leu Lys Val
1               5

```
<210> SEQ ID NO 123
<211> LENGTH: 8
<212> TYPE: PRT
<213> ORGANISM: Arabidopsis thaliana

<400> SEQUENCE: 123

Gly Leu Pro Leu Ala Leu Lys Val
 1               5

<210> SEQ ID NO 124
<211> LENGTH: 8
<212> TYPE: PRT
<213> ORGANISM: Arabidopsis thaliana

<400> SEQUENCE: 124

Gly Leu Pro Leu Ser Val Val Leu
 1               5

<210> SEQ ID NO 125
<211> LENGTH: 8
<212> TYPE: PRT
<213> ORGANISM: Arabidopsis thaliana

<400> SEQUENCE: 125

Gly Leu Pro Leu Ala Leu Ile Thr
 1               5

<210> SEQ ID NO 126
<211> LENGTH: 7
<212> TYPE: PRT
<213> ORGANISM: Arabidopsis thaliana

<400> SEQUENCE: 126

Lys Ile Ser Tyr Asp Ala Leu
 1               5

<210> SEQ ID NO 127
<211> LENGTH: 7
<212> TYPE: PRT
<213> ORGANISM: Arabidopsis thaliana

<400> SEQUENCE: 127

Lys Ile Ser Tyr Asp Gly Leu
 1               5

<210> SEQ ID NO 128
<211> LENGTH: 7
<212> TYPE: PRT
<213> ORGANISM: Arabidopsis thaliana

<400> SEQUENCE: 128

Gly Phe Ser Tyr Lys Asn Leu
 1               5

<210> SEQ ID NO 129
<211> LENGTH: 7
<212> TYPE: PRT
<213> ORGANISM: Arabidopsis thaliana

<400> SEQUENCE: 129

Val Phe Leu Ser Phe Arg Gly
 1               5

<210> SEQ ID NO 130
<211> LENGTH: 9
```

```
<212> TYPE: PRT
<213> ORGANISM: Arabidopsis thaliana

<400> SEQUENCE: 130

Pro Ile Phe Tyr Met Val Asp Pro Ser
1               5

<210> SEQ ID NO 131
<211> LENGTH: 9
<212> TYPE: PRT
<213> ORGANISM: Arabidopsis thaliana

<400> SEQUENCE: 131

Pro Ile Phe Tyr Asp Val Asp Pro Ser
1               5

<210> SEQ ID NO 132
<211> LENGTH: 6
<212> TYPE: PRT
<213> ORGANISM: Arabidopsis thaliana

<400> SEQUENCE: 132

Val Gly Ile Asp Asp His
1               5

<210> SEQ ID NO 133
<211> LENGTH: 6
<212> TYPE: PRT
<213> ORGANISM: Arabidopsis thaliana

<400> SEQUENCE: 133

Val Gly Ile Asp Thr His
1               5

<210> SEQ ID NO 134
<211> LENGTH: 7
<212> TYPE: PRT
<213> ORGANISM: Arabidopsis thaliana

<400> SEQUENCE: 134

Phe Leu Asp Ile Ala Cys Phe
1               5

<210> SEQ ID NO 135
<211> LENGTH: 9
<212> TYPE: PRT
<213> ORGANISM: Arabidopsis thaliana

<400> SEQUENCE: 135

Met His Asp Gln Leu Arg Asp Met Gly
1               5

<210> SEQ ID NO 136
<211> LENGTH: 9
<212> TYPE: PRT
<213> ORGANISM: Arabidopsis thaliana

<400> SEQUENCE: 136

Met His Asp Leu Ile Gln Asp Met Gly
1               5

<210> SEQ ID NO 137

<400> SEQUENCE: 137
```

<210> SEQ ID NO 138
<211> LENGTH: 6
<212> TYPE: PRT
<213> ORGANISM: Arabidopsis thaliana

<400> SEQUENCE: 138

Ser Lys Leu Glu Ser Leu
 1               5

<210> SEQ ID NO 139
<211> LENGTH: 8
<212> TYPE: PRT
<213> ORGANISM: Arabidopsis thaliana

<400> SEQUENCE: 139

Gly Leu His Ser Leu Glu Tyr Leu
 1               5

<210> SEQ ID NO 140
<211> LENGTH: 8
<212> TYPE: PRT
<213> ORGANISM: Arabidopsis thaliana

<400> SEQUENCE: 140

Gly Leu Arg Ser Leu Glu Ile Leu
 1               5

<210> SEQ ID NO 141
<211> LENGTH: 3432
<212> TYPE: DNA
<213> ORGANISM: Arabidopsis thaliana

<400> SEQUENCE: 141

| | | | | | | |
|---|---|---|---|---|---|---|
| acaagtaaaa | gaaagagcga | gaaatcatcg | aaatggattt | catctcatct | cttatcgttg | 60 |
| gctgtgctca | ggtgttgtgt | gaatctatga | atatggcgga | gagaagagga | cataagactg | 120 |
| atcttagaca | agccatcact | gatcttgaaa | cagccatcgg | tgacttgaag | gccatacgtg | 180 |
| atgacctgac | tttacggatc | caacaagacg | gtctagaggg | acgaagctgc | tcaaatcgtg | 240 |
| ccagagagtg | gcttagtgcg | gtgcaagtaa | cggagactaa | aacagcccta | cttttagtga | 300 |
| ggtttaggcg | tcgggaacag | aggacgcgaa | tgaggaggag | atacctcagt | tgtttcggtt | 360 |
| gtgccgacta | caaactgtgc | aagaaggttt | ctgccatatt | gaagagcatt | ggtgagctga | 420 |
| gagaacgctc | tgaagctatc | aaaacagatg | gcgggtcaat | tcaagtaact | tgtagagaga | 480 |
| tacccatcaa | gtccgttgtc | ggaaatacca | cgatgatgga | acaggttttg | gaatttctca | 540 |
| gtgaagaaga | agaaagagga | atcattggtg | tttatggacc | tggtgggggtt | gggaagacaa | 600 |
| cgttaatgca | gagcattaac | aacgagctga | tcacaaaagg | acatcagtat | gatgtactga | 660 |
| tttgggttca | aatgtccaga | gaattcggcg | agtgtacaat | tcagcaagcc | gttggagcac | 720 |
| ggttgggttt | atcttgggac | gagaaggaga | ccggcgaaaa | cagagctttg | aagatataca | 780 |
| gagctttgag | acagaaacgt | tccttgttgt | tgctagatga | gtctgggaag | agatagactt | 840 |
| ggagaaaact | ggagttcctc | gaccttgaca | gggaaaacaa | atgcaaggtg | atgttcacga | 900 |
| cacggtctat | agcattatgc | aacaatatgg | gtgcggaata | caagttgaga | gtggagtttc | 960 |
| tggagaagaa | acacgcgtgg | gagctgttct | gtagtaaggt | atggagaaaa | gatcttttag | 1020 |
| agtcatcatc | aattcgccgg | ctcgcggaga | ttatagtgag | taaatgtgga | ggattgccac | 1080 |

```
tagcgttgat cactttagga ggagccatgg ctcatagaga gacagaagaa gagtggatcc   1140
atgctagtga agttctgact agatttccag cagagatgaa gggtatgaac tatgtatttg   1200
cccttttgaa attcagctac gacaacctcg agagtgatct gcttcggtct tgtttcttgt   1260
actgcgcttt attcccagaa gaacattgta tagagatcga gcagcttgtt cagtactggg   1320
tcggcgaagg gtttctcacc agctcccatg gcgttaacac catttacaag ggatattttc   1380
tcattgggga tctgaaagcg gcatgtttgt tggaaaccgg agatgagaaa acacaggtga   1440
agatgcataa tgtggtcaga agctttgcat tgtggatggc atctgaacag gggacttata   1500
aggagctgat cctagttgag cctagcatgg gacatactga agctcctaaa gcagaaaact   1560
ggcgacaagc ttggtgatct cattgttaga taacagaatc cagaccttgc ctgaaaaact   1620
catatgcccg aaactgacaa cactgatgct ccaacagaac agctctttga agaagattcc   1680
aacagggttt tcatgcata tgcctgttct cagagtcttg gacttgtcgt tcacaagtat   1740
cactgagatt ccgttgtcta tcaagtattt ggtggagttg tatcatctgt ctatgtcagg   1800
aacaaagata agtgtattgc cacaggagct tgggaatctt agaaaactga agcatctgga   1860
cctacaaaga actcagtttc ttcagacgat cccacgagat gccatatgtt ggctgagcaa   1920
gctcgaggtt ctgaacttgt actacagtta cgccggttgg gaactgcaga gctttggaga   1980
agatgaagca aagaactcg gattcgctga cttggaatac ttggaaaacc taaccacact   2040
cggtatcact gttctctcat ggagaccct aaaaactctc ttcgagttcg gtgctttgca   2100
taaacatata cagcatctcc acgttgaaga gtgcaatgaa ctcctctact tcaatctccc   2160
atcactcact aaccatggca ggaacctgag aagacttagc attaaaagtt gccatgactt   2220
ggagtacctg gtcacacccg cagattttga aaatgattgg cttccgagtc tagaggttct   2280
gacgttacac agccttcaca acttaaccag agtgtgggga aattctgtaa gccaagattg   2340
tctgcggaat atccgttgca taaacatttc acactgcaac aagctgaaga atgtctcatg   2400
ggttcagaaa ctcccaaagc tagaggtgat tgaactgttc gactgcagag agatagagga   2460
attgataagc gaacacgaga gtccatccgt cgaagatcca acattgttcc caagcctgaa   2520
gaccttgaga actagggatc tgccagaact aaacagcatc ctcccatctc gattttcatt   2580
ccaaaaagtt gaaacattag tcatcacaaa ttgccccaga gttaagaaac tgccgtttca   2640
ggagaggagg acccagatga acttgccaac agtttattgt gaggagaaat ggtggaaagc   2700
actggaaaaa gttgaaacat tagtcatcac aaattgcccc agagttaaga aactgccgtt   2760
tcaggagagg aggacccaga tgaacttgcc aacagtttat tgtgaggaga atggtggaa   2820
agcactggaa aaagatcaac caaacgaaga gctttgttat ttaccgcgct ttgttccaaa   2880
ttgatataag agctaagagc actctgtaca aatatgtcca ttcataagta gcaggaagcc   2940
aggaaggttg ttccagtgaa gtcatcaact ttccactaga ccacaaaact agagattatg   3000
taatcataaa aaccaaacta tccgcgatca aatagatctc acgactatga ggacgaagac   3060
tcaccgagta tcgtcgatat agaaactcca agctccagtt ccgatcagtg aagacgaaca   3120
agtttatcag atctctgcaa caattctggg aatcgtcacc tcagattaga cctccagtaa   3180
gaagtgagaa agcatggacg acgactgtga agaattgagc taatgagctg aaccggatcc   3240
ggtgaaattg cagaaccgga tcggagaaga agaattttgc atttgtgcat ctttattttt   3300
aattgttacg tttgagcccc aataatcata gatattgtag tgaagaccaa atttcatggt   3360
ggatcaatca aattgtattt tcaaattttc gtagtgtaat aacggaaaaa ggaataaaaa   3420
ggtcactgag ta                                                      3432
```

<210> SEQ ID NO 142
<211> LENGTH: 909
<212> TYPE: PRT
<213> ORGANISM: Arabidopsis thaliana

<400> SEQUENCE: 142

Met Asp Phe Ile Ser Ser Leu Ile Val Gly Cys Ala Gln Val Leu Cys
1               5                   10                  15

Glu Ser Met Asn Met Ala Glu Arg Arg Gly His Lys Thr Asp Leu Arg
            20                  25                  30

Gln Ala Ile Thr Asp Leu Glu Thr Ala Ile Gly Asp Leu Lys Ala Ile
        35                  40                  45

Arg Asp Asp Leu Thr Leu Arg Ile Gln Gln Asp Gly Leu Glu Gly Arg
    50                  55                  60

Ser Cys Ser Asn Arg Ala Arg Glu Trp Leu Ser Ala Val Gln Val Thr
65                  70                  75                  80

Glu Thr Lys Thr Ala Leu Leu Val Arg Phe Arg Arg Glu Gln
                85                  90                  95

Arg Thr Arg Met Arg Arg Arg Tyr Leu Ser Cys Phe Gly Cys Ala Asp
            100                 105                 110

Tyr Lys Leu Cys Lys Lys Val Ser Ala Ile Leu Lys Ser Ile Gly Glu
        115                 120                 125

Leu Arg Glu Arg Ser Glu Ala Ile Lys Thr Asp Gly Gly Ser Ile Gln
    130                 135                 140

Val Thr Cys Arg Glu Ile Pro Ile Lys Ser Val Val Gly Asn Thr Thr
145                 150                 155                 160

Met Met Glu Gln Val Leu Glu Phe Leu Ser Glu Glu Glu Arg Gly
                165                 170                 175

Ile Ile Gly Val Tyr Gly Pro Gly Gly Val Gly Lys Thr Thr Leu Met
            180                 185                 190

Gln Ser Ile Asn Asn Glu Leu Ile Thr Lys Gly His Gln Tyr Asp Val
        195                 200                 205

Leu Ile Trp Val Gln Met Ser Arg Glu Phe Gly Glu Cys Thr Ile Gln
    210                 215                 220

Gln Ala Val Gly Ala Arg Leu Gly Leu Ser Trp Asp Glu Lys Glu Thr
225                 230                 235                 240

Gly Glu Asn Arg Ala Leu Lys Ile Tyr Arg Ala Leu Arg Gln Lys Arg
                245                 250                 255

Phe Leu Leu Leu Leu Asp Asp Val Trp Glu Glu Ile Asp Leu Glu Lys
            260                 265                 270

Thr Gly Val Pro Arg Pro Asp Arg Glu Asn Lys Cys Lys Val Met Phe
        275                 280                 285

Thr Thr Arg Ser Ile Ala Leu Cys Asn Asn Met Gly Ala Glu Tyr Lys
    290                 295                 300

Leu Arg Val Glu Phe Leu Glu Lys Lys His Ala Trp Glu Leu Phe Cys
305                 310                 315                 320

Ser Lys Val Trp Arg Lys Asp Leu Leu Glu Ser Ser Ile Arg Arg
                325                 330                 335

Leu Ala Glu Ile Ile Val Ser Lys Cys Gly Gly Leu Pro Leu Ala Leu
            340                 345                 350

Ile Thr Leu Gly Gly Ala Met Ala His Arg Glu Thr Glu Glu Glu Trp
        355                 360                 365

Ile His Ala Ser Glu Val Leu Thr Arg Phe Pro Ala Glu Met Lys Gly

-continued

```
            370                 375                 380
Met Asn Tyr Val Phe Ala Leu Leu Lys Phe Ser Tyr Asp Asn Leu Glu
385                 390                 395                 400

Ser Asp Leu Leu Arg Ser Cys Phe Leu Tyr Cys Ala Leu Phe Pro Glu
                405                 410                 415

Glu His Ser Ile Glu Ile Glu Gln Leu Val Glu Tyr Trp Val Gly Glu
                420                 425                 430

Gly Phe Leu Thr Ser Ser His Gly Val Asn Thr Ile Tyr Lys Gly Tyr
                435                 440                 445

Phe Leu Ile Gly Asp Leu Lys Ala Ala Cys Leu Leu Glu Thr Gly Asp
450                 455                 460

Glu Lys Thr Gln Val Lys Met His Asn Val Val Arg Ser Phe Ala Leu
465                 470                 475                 480

Trp Met Ala Ser Glu Gln Gly Thr Tyr Lys Glu Leu Ile Leu Val Glu
                485                 490                 495

Pro Ser Met Gly His Thr Glu Ala Pro Lys Ala Glu Asn Trp Arg Gln
                500                 505                 510

Ala Leu Val Ile Ser Leu Leu Asp Asn Arg Ile Gln Thr Leu Pro Glu
                515                 520                 525

Lys Leu Ile Cys Pro Lys Leu Thr Thr Leu Met Leu Gln Gln Asn Ser
530                 535                 540

Ser Leu Lys Lys Ile Pro Thr Gly Phe Phe Met His Met Pro Val Leu
545                 550                 555                 560

Arg Val Leu Asp Leu Ser Phe Thr Ser Ile Thr Glu Ile Pro Leu Ser
                565                 570                 575

Ile Lys Tyr Leu Val Glu Leu Tyr His Leu Ser Met Ser Gly Thr Lys
                580                 585                 590

Ile Ser Val Leu Pro Gln Glu Leu Gly Asn Leu Arg Lys Leu Lys His
                595                 600                 605

Leu Asp Leu Gln Arg Thr Gln Phe Leu Gln Thr Ile Pro Arg Asp Ala
                610                 615                 620

Ile Cys Trp Leu Ser Lys Leu Glu Val Leu Asn Leu Tyr Tyr Ser Tyr
625                 630                 635                 640

Ala Gly Trp Glu Leu Gln Ser Phe Gly Glu Asp Glu Ala Glu Glu Leu
                645                 650                 655

Gly Phe Ala Asp Leu Glu Tyr Leu Glu Asn Leu Thr Thr Leu Gly Ile
                660                 665                 670

Thr Val Leu Ser Leu Glu Thr Leu Lys Thr Leu Phe Glu Phe Gly Ala
                675                 680                 685

Leu His Lys His Ile Gln His Leu His Val Glu Glu Cys Asn Glu Leu
                690                 695                 700

Leu Tyr Phe Asn Leu Pro Ser Leu Thr Asn His Gly Arg Asn Leu Arg
705                 710                 715                 720

Arg Leu Ser Ile Lys Ser Cys His Asp Leu Glu Tyr Leu Val Thr Pro
                725                 730                 735

Ala Asp Phe Glu Asn Asp Trp Leu Pro Ser Leu Glu Val Leu Thr Leu
                740                 745                 750

His Ser Leu His Asn Leu Thr Arg Val Trp Gly Asn Ser Val Ser Gln
                755                 760                 765

Asp Cys Leu Arg Asn Ile Arg Cys Ile Asn Ile Ser His Cys Asn Lys
                770                 775                 780

Leu Lys Asn Val Ser Trp Val Gln Lys Leu Pro Lys Leu Glu Val Ile
785                 790                 795                 800
```

-continued

```
Glu Leu Phe Asp Cys Arg Glu Ile Glu Leu Ile Ser Glu His Glu
            805                 810                 815

Ser Pro Ser Val Glu Asp Pro Thr Leu Phe Pro Ser Leu Lys Thr Leu
            820                 825                 830

Arg Thr Arg Asp Leu Pro Glu Leu Asn Ser Ile Leu Pro Ser Arg Phe
            835                 840                 845

Ser Phe Gln Lys Val Glu Thr Leu Val Ile Thr Asn Cys Pro Arg Val
            850                 855                 860

Lys Lys Leu Pro Phe Gln Glu Arg Arg Thr Gln Met Asn Leu Pro Thr
865                 870                 875                 880

Val Tyr Cys Glu Glu Lys Trp Trp Lys Ala Leu Glu Lys Asp Gln Pro
                885                 890                 895

Asn Glu Glu Leu Cys Tyr Leu Pro Arg Phe Val Pro Asn
            900                 905

<210> SEQ ID NO 143
<211> LENGTH: 22
<212> TYPE: PRT
<213> ORGANISM: Arabidopsis thaliana

<400> SEQUENCE: 143

Pro Lys Ala Glu Asn Trp Arg Gln Ala Leu Val Ile Ser Leu Leu Asp
1               5                   10                  15

Asn Arg Ile Gln Thr Leu
            20

<210> SEQ ID NO 144
<211> LENGTH: 23
<212> TYPE: PRT
<213> ORGANISM: Arabidopsis thaliana

<400> SEQUENCE: 144

Pro Glu Lys Leu Ile Cys Pro Lys Leu Thr Thr Leu Met Leu Gln Gln
1               5                   10                  15

Asn Ser Ser Leu Lys Lys Ile
            20

<210> SEQ ID NO 145
<211> LENGTH: 24
<212> TYPE: PRT
<213> ORGANISM: Arabidopsis thaliana

<400> SEQUENCE: 145

Pro Thr Gly Phe Phe Met His Met Pro Val Leu Arg Val Leu Asp Leu
1               5                   10                  15

Ser Phe Thr Ser Ile Thr Glu Ile
            20

<210> SEQ ID NO 146
<211> LENGTH: 23
<212> TYPE: PRT
<213> ORGANISM: Arabidopsis thaliana

<400> SEQUENCE: 146

Pro Leu Ser Ile Lys Tyr Leu Val Glu Leu Tyr His Leu Ser Met Ser
1               5                   10                  15

Gly Thr Lys Ile Ser Val Leu
            20
```

```
<210> SEQ ID NO 147
<211> LENGTH: 24
<212> TYPE: PRT
<213> ORGANISM: Arabidopsis thaliana

<400> SEQUENCE: 147

Pro Gln Glu Leu Gly Asn Leu Arg Lys Leu Lys His Leu Asp Leu Gln
 1               5                  10                  15

Arg Thr Gln Phe Leu Gln Thr Ile
            20

<210> SEQ ID NO 148
<211> LENGTH: 37
<212> TYPE: PRT
<213> ORGANISM: Arabidopsis thaliana

<400> SEQUENCE: 148

Pro Arg Asp Ala Ile Cys Trp Leu Ser Lys Leu Glu Val Leu Asn Leu
 1               5                  10                  15

Tyr Tyr Ser Tyr Ala Gly Trp Glu Leu Gln Ser Phe Gly Glu Asp Glu
            20                  25                  30

Ala Glu Glu Leu Gly
        35

<210> SEQ ID NO 149
<211> LENGTH: 25
<212> TYPE: PRT
<213> ORGANISM: Arabidopsis thaliana

<400> SEQUENCE: 149

Phe Ala Asp Leu Glu Tyr Leu Glu Asn Leu Thr Thr Leu Gly Ile Thr
 1               5                  10                  15

Val Leu Ser Leu Glu Thr Leu Lys Thr
            20                  25

<210> SEQ ID NO 150
<211> LENGTH: 27
<212> TYPE: PRT
<213> ORGANISM: Arabidopsis thaliana

<400> SEQUENCE: 150

Leu Phe Glu Phe Gly Ala Leu His Lys His Ile Gln His Leu His Val
 1               5                  10                  15

Glu Glu Cys Asn Glu Leu Leu Tyr Phe Asn Leu
            20                  25

<210> SEQ ID NO 151
<211> LENGTH: 26
<212> TYPE: PRT
<213> ORGANISM: Arabidopsis thaliana

<400> SEQUENCE: 151

Pro Ser Leu Thr Asn His Gly Arg Asn Leu Arg Arg Leu Ser Ile Lys
 1               5                  10                  15

Ser Cys His Asp Leu Glu Tyr Leu Val Thr
            20                  25

<210> SEQ ID NO 152
<211> LENGTH: 29
<212> TYPE: PRT
<213> ORGANISM: Arabidopsis thaliana

<400> SEQUENCE: 152
```

Pro Ala Asp Phe Glu Asn Asp Trp Leu Pro Ser Leu Glu Val Leu Thr
1               5                   10                  15

Leu His Ser Leu His Asn Leu Thr Arg Val Trp Gly Asn
            20                  25

<210> SEQ ID NO 153
<211> LENGTH: 30
<212> TYPE: PRT
<213> ORGANISM: Arabidopsis thaliana

<400> SEQUENCE: 153

Ser Val Ser Gln Asp Cys Leu Arg Asn Ile Arg Cys Ile Asn Ile Ser
1               5                   10                  15

His Cys Asn Lys Leu Lys Asn Val Ser Trp Val Gln Lys Leu
            20                  25                  30

<210> SEQ ID NO 154
<211> LENGTH: 28
<212> TYPE: PRT
<213> ORGANISM: Arabidopsis thaliana

<400> SEQUENCE: 154

Pro Lys Leu Glu Val Ile Glu Leu Phe Asp Cys Arg Glu Ile Glu Glu
1               5                   10                  15

Leu Ile Ser Glu His Glu Ser Pro Ser Val Glu Asp
            20                  25

<210> SEQ ID NO 155
<211> LENGTH: 22
<212> TYPE: PRT
<213> ORGANISM: Arabidopsis thaliana

<400> SEQUENCE: 155

Pro Thr Leu Phe Pro Ser Leu Lys Thr Leu Arg Thr Arg Asp Leu Pro
1               5                   10                  15

Glu Leu Asn Ser Ile Leu
            20

<210> SEQ ID NO 156
<211> LENGTH: 23
<212> TYPE: PRT
<213> ORGANISM: Arabidopsis thaliana

<400> SEQUENCE: 156

Pro Ser Arg Phe Ser Phe Gln Lys Val Glu Thr Leu Val Ile Thr Asn
1               5                   10                  15

Cys Pro Arg Val Lys Lys Leu
            20

<210> SEQ ID NO 157
<211> LENGTH: 5134
<212> TYPE: DNA
<213> ORGANISM: Arabidopsis thaliana

<400> SEQUENCE: 157
aagctttaca gattggatga tctcttaatg catgctgaag tgactgcaaa aaggttagca      60
atattcagtg gttctcgtta tgaatatttc atgaacggaa gcagcactga gaaaatgagg     120
cccttgttat ctgattttct gcaagagatt gagtctgtca aggtagagtt cagaaatgtt     180
tgcttgcaag ttctggatat atcaccttt tccctgacag atggagaagg ccttgttaat     240

-continued

```
ttcttattaa aaaaccaggc caaggtgccg aatgatgatg ctgtttcttc tgatggaagt      300
ttagaggatg caagcagcac tgagaaaatg ggacttccat ctgattttct ccgagagatt      360
gagtctgttg agataaagga ggccagaaaa ttatatgatc aagttttgga tgcaacacat      420
tgtgagacga gtaagcacga tggaaaaagc tttatcaaca ttatgttaac ccaacaggac      480
aaggtgctgg actatgatgc tggttcagtg tcttatcttc ttaaccaaat ctcagtagtt      540
aaagacaaaa tattgcacat tggctcttta cttgtagata ttgtacagta ccggaatatg      600
catatagaac ttacagatct cgctgaacgt gttcaagata aaaactacat tcgtttcttc      660
tctgtcaagg gttatattcc tgcttggtat tacacactat atctctctga tgtcaagcaa      720
ttgcttaagt ttgttgaggc agaggtaaag attatttgtc tgaaagtacc agattcttca      780
agttatagct tccctaagac aaatggatta ggatatctca attgcttttt aggcaaattg      840
gaggagcttt tacgttctaa gctcgatttg ataatcgact aaaacatca gattgaatca       900 gtcaaggagg gcttattgtg cctaagatca ttcattgatc attttcaga aagctatgtt       960 gagcatgatg aagcttgtgg tcttatagca agagtttctg taatggcata caaggctgag     1020
tatgtcattg actcatgctt ggcctattct catccactct ggtacaaagt tctttggatt     1080
tctgaagttc ttgagaatat taagcttgta aataaagttg ttggggagac atgtgaaaga     1140
aggaacactg aagttactgt gcatgaagtt gcaaagacta ccactaatgt agcaccatct     1200
ttttcagctt atactcaaag agcaaacgaa gaaatggagg gttttcagga tacaatagat     1260
gaattaaagg ataaactact tggaggatca cctgagcttg atgtcatctc aatcgttggc     1320
atgccaggat tgggcaagac tacactagca aagaagattt acaatgatcc agaagtcacc     1380
tctcgcttcg atgtccatgc tcaatgtgtt gtgactcaat tatattcatg gagagagttg     1440
ttgctcacca ttttgaatga tgtgcttgag ccttctgatc gcaatgaaaa agaagatgga     1500
gaaatagctg atgatctacg ccgatttttg ttgaccaaga gattcttgat tctcattgat     1560
gatgtgtggg actataaagt gtgggacaat ctatgtatgt gcttcagtga tgtttcaaat     1620
aggagtagaa ttatcctaac aacccgcttg aatgatgtcg ccgaatatgt caaatgtgaa     1680
agtgatcccc atcatcttcg tttattcaga gatgacgaga gttggacatt attacagaaa     1740
gaagtctttc aaggagagag ctgtccacct gaacttgaag atgtgggatt tgaaatatca     1800
aaaagttgta gagggttgcc tctctcagtt gtgttagtag ctggtgttct gaaacagaaa     1860
aagaagacac tagattcatg gaaagtagta gaacaaagtc taagttccca gaggattggc     1920
agcttggaag agagcatatc tataattgga ttcagttaca agaatttacc acactatctt     1980
aagccttgtt ttctctatt tggaggattt tgcagggaa aggatattca tgactcaaaa       2040
atgaccaagt tgtgggtagc tgaagagttt gtacaagcaa caacgaaaa aggacaagaa      2100 gatacccgca aaggtttct tggacgatct tattggtagg aatctggtga tggccatgga     2160
gaagagacct aatgccaagg tgaaaacgtg ccgcattcat gatttgttgc ataaattctg     2220
catggaaaag gccaaacaag aggatttcct tctccagatc aataggtaaa aaaaactgta     2280
ttaattttac attacaaaaa aaaagaactg tattaatttt actgtattat gtttatgcca     2340
actctcattt ccatgtgttc tcttttattc aattcagtgg agaaggtgta tttcctgaac     2400
gattggaaga ataccgattg ttcgttcatt cttaccaaga tgaaattgat ctgtggcgcc     2460
catctcgctc taatgtccgc tctttactat tcaatgcaat tgatccagat aacttgttat     2520
ggccgcgtga tatctccttc attttttgaga gcttcaagct tgttaaagtg ttggatttgg     2580
aatcattcaa cattggtggt acttttccca ttgaaacaca atatctaatt cagatgaagt     2640
```

-continued

```
actttgcggc ccaaactgat gcaaattcaa ttccttcatc tatagctaag cttgaaaatc    2700
ttgagacttt tgtcgtaaga ggattgggag gagagatgat attaccttgt tcacttctga    2760
agatggtgaa attgaggcat atacatgtaa atgatcggt  ttcttttggt ttgcgtgaga    2820
acatggatgt tttaactggt aactcacaat aacctaattt ggaaaccttt tctactccgc    2880
gtctctttta tggtaaagac gcagagaaga ttttgaggaa gatgccaaaa ttgagaaaat    2940
tgagttgcat attttcaggg acatttggtt attcaaggaa attgaagggt aggtgtgttc    3000
gttttcccag attagatttt ctaagtcacc ttgagtccct caagctggtt tcgaacagct    3060
atccagccaa acttcctcac aagttcaatt tcccctcgca actaagggaa ctgactttat    3120
caaagttccg tctaccttgg acccaaattt cgatcattgc agaactgccc aacttggtga    3180
ttcttaagtt attgctcaga gcctttgaag gggatcactg ggaagtgaaa gattcagagt    3240
tcctagaact caaatactta aaactggaca acctcaaagt tgtacaatgg tccatctctg    3300
atgatgcttt tcctaagctt gaacatttgg ttttaacgaa atgtaagcat cttgagaaaa    3360
tcccttctcg ttttgaagat gctgtttgtc taaatagagt tgaggtgaac tggtgcaact    3420
ggaatgttgc caattcagcc caagatattc aaactatgca acatgaagtt atagcaaatg    3480
attcattcac agttactata cagcctccag attggtctaa agaacagccc cttgactctt    3540
agcaaaggtt tgttcttgct gtgttcatcc aagtgcattt aacatttatt cattttgttt    3600
tacaccagaa catgtttatt ttgctagtat tacttgatac attaaaagaa atcgaactca    3660
tatttctgct acagtcttaa cttttcttgg gcttacttga ggtctagatt agatcaatgg    3720
ttcatgtaat ttttaattca ctgtttcatt caactgtctt atgatagttg tgaaatgaca    3780
atattgttat ccctagccaa atttattatg ttcaaatgaa aactgatgtc acaactactt    3840
ttttgtgaaa tgttttttgaa tttttttgcta taaaattgac gaattgacag cttctatatt    3900
tgtcagctaa actctttgtc accagaagtg tatttagaat tactgtggtt ttatgaaaga    3960
gttctgtaga attttatgct tttgcagaat atagtttaaa acaacaacac ttctctgttt    4020
cagagatagc agaagctaaa gttcaaggca ttttgtttat ttctagaaca agtggagttc    4080
ttatgttgaa ttcttgaaaa gaagaagaat caggagcagg taaagttatc tcttttatg     4140 ttttttcttct tttagatgtt atttcttcat cttgaacgtg aacaccgctg aaagcatttt    4200
aataaaaccg gagagaaaaa taagatcttt ttatataaag cattatcatg taaatatgcc    4260
taaatccata tggtacaact gtttgacaaa atgatagaga ggggagtttt atagtataag    4320
taaaacagga ttgagaaaaa atccttgca  cgattttcaa tttctggcca catcacaatg    4380
tgtgtcaaag ttcccctctt taagtggaac aagcaatcag aaaagctcat tcttatcggt    4440
gacataccaa taccagctga ctgtctcatc ttggttaact tagccttgct tacttagact    4500
attagattag ttactaatga actggtaaat tggaaccaaa tgtagttagc ttgatgagct    4560
ggtagacatg tatatatgaa gatacacgcg taactttagt cgatggttaa ttttcatt     4620 ttgattttt  ttcttcacag agtatatatg aacttggcct aaaagttttg cttcactaat    4680
ttaactatta ccgtggatga aacaagcatg gcaacatttt caacaactat cactcaagca    4740
atgtaaaaaa tggaggttct acgagcggta catgtaagag ttttgtgcac acaagaggtt    4800
ctgagacttg aaccatccat gtccaaggca gttgagatgc tagtaaagaa agaagaagat    4860
gagcctgcac taattaatct ccctgtatga atgagagaat gagaaaaaga tggagcttca    4920
tgaaccaaaa gttacctttt tttttctttc ttaatggcat tactttgaag cacatgtttg    4980
```

```
ttagttgtaa attgtaatgg tgaagtgttt gtaaatatag ggagtgatat ttgaaagaat      5040
ggttgtgtta tctttacaaa ccggaatcat ttctgtataa ttttcttctg taattttgg       5100 tttcggttta ttcattactc atttcagtaa gctt                                  5134
```

<210> SEQ ID NO 158
<211> LENGTH: 26
<212> TYPE: DNA
<213> ORGANISM: Arabidopsis thaliana
<220> FEATURE:
<221> NAME/KEY: misc_feature
<222> LOCATION: (1)...(26)
<223> OTHER INFORMATION: n = A,T,C or G

<400> SEQUENCE: 158

```
ggnatgggng gnntnggnaa racnac                                           26
```

<210> SEQ ID NO 159
<211> LENGTH: 20
<212> TYPE: DNA
<213> ORGANISM: Arabidopsis thaliana
<220> FEATURE:
<221> NAME/KEY: misc_feature
<222> LOCATION: (1)...(20)
<223> OTHER INFORMATION: n = A,T,C or G

<400> SEQUENCE: 159

```
ncgngwngtn akdawncgna                                                  20
```

<210> SEQ ID NO 160
<211> LENGTH: 17
<212> TYPE: DNA
<213> ORGANISM: Arabidopsis thaliana
<220> FEATURE:
<221> NAME/KEY: misc_feature
<222> LOCATION: (1)...(17)
<223> OTHER INFORMATION: n = A,T,C or G

<400> SEQUENCE: 160

```
ggwntbggwa arachac                                                     17
```

<210> SEQ ID NO 161
<211> LENGTH: 33
<212> TYPE: DNA
<213> ORGANISM: Arabidopsis thaliana
<220> FEATURE:
<221> NAME/KEY: misc_feature
<222> LOCATION: (1)...(33)
<223> OTHER INFORMATION: n = A,T,C or G

<400> SEQUENCE: 161

```
nrynrdngtn gtyttnccna nnccnssnrk ncc                                   33
```

<210> SEQ ID NO 162
<211> LENGTH: 26
<212> TYPE: DNA
<213> ORGANISM: Arabidopsis thaliana
<220> FEATURE:
<221> NAME/KEY: misc_feature
<222> LOCATION: (1)...(26)
<223> OTHER INFORMATION: n = A,T,C or G

<400> SEQUENCE: 162

```
ggnmynssng gnntnggnaa racnac                                           26
```

<210> SEQ ID NO 163
<211> LENGTH: 13

```
<212> TYPE: DNA
<213> ORGANISM: Arabidopsis thaliana

<400> SEQUENCE: 163
tygaygayrt bra                                                      13

<210> SEQ ID NO 164
<211> LENGTH: 16
<212> TYPE: DNA
<213> ORGANISM: Arabidopsis thaliana
<220> FEATURE:
<221> NAME/KEY: misc_feature
<222> LOCATION: (1)...(16)
<223> OTHER INFORMATION: n = A,T,C or G

<400> SEQUENCE: 164
tyccavayrt crtcna                                                   16

<210> SEQ ID NO 165
<211> LENGTH: 26
<212> TYPE: DNA
<213> ORGANISM: Arabidopsis thaliana
<220> FEATURE:
<221> NAME/KEY: misc_feature
<222> LOCATION: (1)...(26)
<223> OTHER INFORMATION: n = A,T,C or G

<400> SEQUENCE: 165
vymnayrtcr tcnadnavna nnarna                                        26

<210> SEQ ID NO 166
<211> LENGTH: 26
<212> TYPE: DNA
<213> ORGANISM: Arabidopsis thaliana
<220> FEATURE:
<221> NAME/KEY: misc_feature
<222> LOCATION: (1)...(26)
<223> OTHER INFORMATION: n = A,T,C or G

<400> SEQUENCE: 166
wwnmrrdtny tnntnbtnht ngayga                                        26

<210> SEQ ID NO 167
<211> LENGTH: 21
<212> TYPE: DNA
<213> ORGANISM: Arabidopsis thaliana
<220> FEATURE:
<221> NAME/KEY: misc_feature
<222> LOCATION: (1)...(21)
<223> OTHER INFORMATION: n = A,T,C or G

<400> SEQUENCE: 167
ncgngwngtn akdawncgng a                                             21

<210> SEQ ID NO 168
<211> LENGTH: 21
<212> TYPE: DNA
<213> ORGANISM: Arabidopsis thaliana
<220> FEATURE:
<221> NAME/KEY: misc_feature
<222> LOCATION: (1)...(21)
<223> OTHER INFORMATION: n = A,T,C or G

<400> SEQUENCE: 168
ncknswngtn addatdaatn g                                             21

<210> SEQ ID NO 169
```

<211> LENGTH: 12
<212> TYPE: DNA
<213> ORGANISM: Arabidopsis thaliana
<220> FEATURE:
<221> NAME/KEY: misc_feature
<222> LOCATION: (1)...(12)
<223> OTHER INFORMATION: n = A,T,C or G

<400> SEQUENCE: 169
narnggnarn cc                                                                12

<210> SEQ ID NO 170
<211> LENGTH: 17
<212> TYPE: DNA
<213> ORGANISM: Arabidopsis thaliana

<400> SEQUENCE: 170
ggwytbccwy tbgchyt                                                           17

<210> SEQ ID NO 171
<211> LENGTH: 17
<212> TYPE: DNA
<213> ORGANISM: Arabidopsis thaliana
<220> FEATURE:
<221> NAME/KEY: misc_feature
<222> LOCATION: (1)...(17)
<223> OTHER INFORMATION: n = A,T,C or G

<400> SEQUENCE: 171
ardgcvarwg gvarncc                                                           17

<210> SEQ ID NO 172
<211> LENGTH: 24
<212> TYPE: DNA
<213> ORGANISM: Arabidopsis thaliana
<220> FEATURE:
<221> NAME/KEY: misc_feature
<222> LOCATION: (1)...(24)
<223> OTHER INFORMATION: n = A,T,C or G

<400> SEQUENCE: 172
nrnnwynavn shnarnggna rncc                                                   24

<210> SEQ ID NO 173
<211> LENGTH: 17
<212> TYPE: DNA
<213> ORGANISM: Arabidopsis thaliana
<220> FEATURE:
<221> NAME/KEY: misc_feature
<222> LOCATION: (1)...(17)
<223> OTHER INFORMATION: n = A,T,C or G

<400> SEQUENCE: 173
ggnytnccny tndsnbt                                                           17

<210> SEQ ID NO 174
<211> LENGTH: 20
<212> TYPE: DNA
<213> ORGANISM: Arabidopsis thaliana

<400> SEQUENCE: 174
arrttrtcrt adswrawytt                                                        20

<210> SEQ ID NO 175
<211> LENGTH: 20
<212> TYPE: DNA
<213> ORGANISM: Arabidopsis thaliana

```
<220> FEATURE:
<221> NAME/KEY: misc_feature
<222> LOCATION: (1)...(20)
<223> OTHER INFORMATION: n = A,T,C or G

<400> SEQUENCE: 175
arnyyntyrt ansrnannyy                                              20

<210> SEQ ID NO 176
<211> LENGTH: 20
<212> TYPE: DNA
<213> ORGANISM: Arabidopsis thaliana
<220> FEATURE:
<221> NAME/KEY: misc_feature
<222> LOCATION: (1)...(20)
<223> OTHER INFORMATION: n = A,T,C or G

<400> SEQUENCE: 176
rrnwthwsnt ayranrvnyt                                              20

<210> SEQ ID NO 177
<211> LENGTH: 20
<212> TYPE: DNA
<213> ORGANISM: Arabidopsis thaliana
<220> FEATURE:
<221> NAME/KEY: misc_feature
<222> LOCATION: (1)...(20)
<223> OTHER INFORMATION: n = A,T,C or G

<400> SEQUENCE: 177
gtnttyytnw snttymgrgg                                              20

<210> SEQ ID NO 178
<211> LENGTH: 23
<212> TYPE: DNA
<213> ORGANISM: Arabidopsis thaliana
<220> FEATURE:
<221> NAME/KEY: misc_feature
<222> LOCATION: (1)...(23)
<223> OTHER INFORMATION: n = A,T,C or G

<400> SEQUENCE: 178
ccnathttyt ayrwbgtnga ycc                                          23

<210> SEQ ID NO 179
<211> LENGTH: 17
<212> TYPE: DNA
<213> ORGANISM: Arabidopsis thaliana
<220> FEATURE:
<221> NAME/KEY: misc_feature
<222> LOCATION: (1)...(17)
<223> OTHER INFORMATION: n = A,T,C or G

<400> SEQUENCE: 179
gtnggnathg ayrmnca                                                 17

<210> SEQ ID NO 180
<211> LENGTH: 21
<212> TYPE: DNA
<213> ORGANISM: Arabidopsis thaliana
<220> FEATURE:
<221> NAME/KEY: misc_feature
<222> LOCATION: (1)...(21)
<223> OTHER INFORMATION: n = A,T,C or G

<400> SEQUENCE: 180
raarcangcd atrtcnarra a                                            21
```

<210> SEQ ID NO 181
<211> LENGTH: 20
<212> TYPE: DNA
<213> ORGANISM: Arabidopsis thaliana
<220> FEATURE:
<221> NAME/KEY: misc_feature
<222> LOCATION: (1)...(20)
<223> OTHER INFORMATION: n = A,T,C or G

<400> SEQUENCE: 181
ttyytngaya thgcntgytt                                               20

<210> SEQ ID NO 182
<211> LENGTH: 26
<212> TYPE: DNA
<213> ORGANISM: Arabidopsis thaliana
<220> FEATURE:
<221> NAME/KEY: misc_feature
<222> LOCATION: (1)...(26)
<223> OTHER INFORMATION: n = A,T,C or G

<400> SEQUENCE: 182
cccatrtcyy knadnwrrtc rtgcat                                        26

<210> SEQ ID NO 183
<211> LENGTH: 26
<212> TYPE: DNA
<213> ORGANISM: Arabidopsis thaliana
<220> FEATURE:
<221> NAME/KEY: misc_feature
<222> LOCATION: (1)...(26)
<223> OTHER INFORMATION: n = A,T,C or G

<400> SEQUENCE: 183
atgcaygayy wnhtnmrrga yatggg                                        26

<210> SEQ ID NO 184
<211> LENGTH: 15
<212> TYPE: DNA
<213> ORGANISM: Arabidopsis thaliana
<220> FEATURE:
<221> NAME/KEY: misc_feature
<222> LOCATION: (1)...(15)
<223> OTHER INFORMATION: n = A,T,C or G

<400> SEQUENCE: 184
narnswytyn arytt                                                    15

<210> SEQ ID NO 185
<211> LENGTH: 17
<212> TYPE: DNA
<213> ORGANISM: Arabidopsis thaliana
<220> FEATURE:
<221> NAME/KEY: misc_feature
<222> LOCATION: (1)...(17)
<223> OTHER INFORMATION: n = A,T,C or G

<400> SEQUENCE: 185
wsnaarytnr arwsnyt                                                  17

<210> SEQ ID NO 186
<211> LENGTH: 21
<212> TYPE: DNA
<213> ORGANISM: Arabidopsis thaliana
<220> FEATURE:
<221> NAME/KEY: misc_feature
<222> LOCATION: (1)...(21)
<223> OTHER INFORMATION: n = A,T,C or G

<400> SEQUENCE: 186
dwwytcnarn swnyknarnc c                               21

<210> SEQ ID NO 187
<211> LENGTH: 17
<212> TYPE: DNA
<213> ORGANISM: Arabidopsis thaliana
<220> FEATURE:
<221> NAME/KEY: misc_feature
<222> LOCATION: (1)...(17)
<223> OTHER INFORMATION: n = A,T,C or G

<400> SEQUENCE: 187
ggnytnmrnw snytnga                                    17

<210> SEQ ID NO 188
<211> LENGTH: 13
<212> TYPE: PRT
<213> ORGANISM: Arabidopsis thaliana

<400> SEQUENCE: 188

Leu Lys Phe Ser Tyr Asp Asn Leu Glu Ser Asp Leu Leu
 1               5                  10

<210> SEQ ID NO 189
<211> LENGTH: 16
<212> TYPE: PRT
<213> ORGANISM: Arabidopsis thaliana

<400> SEQUENCE: 189

Gly Val Tyr Gly Pro Gly Gly Val Gly Lys Thr Thr Leu Met Gln Ser
 1               5                  10                  15

<210> SEQ ID NO 190
<211> LENGTH: 14
<212> TYPE: PRT
<213> ORGANISM: Arabidopsis thaliana

<400> SEQUENCE: 190

Gly Gly Leu Pro Leu Ala Leu Ile Thr Leu Gly Gly Ala Met
 1               5                  10

<210> SEQ ID NO 191
<211> LENGTH: 11
<212> TYPE: PRT
<213> ORGANISM: Arabidopsis thaliana
<220> FEATURE:
<221> NAME/KEY: VARIANT
<222> LOCATION: (2)...(2)
<223> OTHER INFORMATION: Xaa is Met or Pro
<220> FEATURE:
<221> NAME/KEY: VARIANT
<222> LOCATION: (3)...(3)
<223> OTHER INFORMATION: Xaa is Gly or Pro
<220> FEATURE:
<221> NAME/KEY: VARIANT
<222> LOCATION: (5)...(5)
<223> OTHER INFORMATION: Xaa is Ile, Leu or Val
<220> FEATURE:
<221> NAME/KEY: VARIANT
<222> LOCATION: (10)...(10)
<223> OTHER INFORMATION: Xaa is Ile, Leu or Thr
<220> FEATURE:
<221> NAME/KEY: VARIANT
<222> LOCATION: (11)...(11)
<223> OTHER INFORMATION: Xaa is Ala or Met

<400> SEQUENCE: 191

```
Gly Xaa Xaa Gly Xaa Gly Lys Thr Thr Xaa Xaa
 1               5                   10
```

<210> SEQ ID NO 192
<211> LENGTH: 11
<212> TYPE: PRT
<213> ORGANISM: Arabidopsis thaliana
<220> FEATURE:
<221> NAME/KEY: VARIANT
<222> LOCATION: (1)...(11)
<223> OTHER INFORMATION: Xaa at 1 is Phe or Lys; Xaa at 2 is Arg or Lys;
      Xaa at 3 is Ile, Val or Phe; Xaa at 5 is Ile, Leu
      or Val; Xaa at 6 is Ile or Leu; Xaa at 7 is Ile or
      Val; Xaa at 10 is Ile, Leu or Val; Xaa at 11 is
      Asp or Trp;

<400> SEQUENCE: 192

```
Xaa Xaa Xaa Leu Xaa Xaa Xaa Asp Asp Xaa Xaa
 1               5                   10
```

<210> SEQ ID NO 193
<211> LENGTH: 8
<212> TYPE: PRT
<213> ORGANISM: Arabidopsis thaliana
<220> FEATURE:
<221> NAME/KEY: VARIANT
<222> LOCATION: (1)...(8)
<223> OTHER INFORMATION: Xaa at 1 is Ser or Cys; Xaa at 2 is Arg or Lys;
      Xaa at 3 is Phe, Ile or Val; Xaa at 4 is Ile or
      Met; Xaa at 5 is Ile, Leu or Phe; Xaa at 7 is Ser,
      Cys or Thr;

<400> SEQUENCE: 193

```
Xaa Xaa Xaa Xaa Xaa Thr Xaa Arg
 1               5
```

<210> SEQ ID NO 194
<211> LENGTH: 8
<212> TYPE: PRT
<213> ORGANISM: Arabidopsis thaliana
<220> FEATURE:
<221> NAME/KEY: VARIANT
<222> LOCATION: (1)...(8)
<223> OTHER INFORMATION: Xaa at 5 is Thr, Ala or Thr; Xaa at 6 is Leu or
      Val; Xaa at 7 is Ile, Val or Lys; Xaa at 8 is Val
      or Thr;

<400> SEQUENCE: 194

```
Gly Leu Pro Leu Xaa Xaa Xaa Xaa
 1               5
```

<210> SEQ ID NO 195
<211> LENGTH: 7
<212> TYPE: PRT
<213> ORGANISM: Arabidopsis thaliana
<220> FEATURE:
<221> NAME/KEY: VARIANT
<222> LOCATION: (1)...(7)
<223> OTHER INFORMATION: Xaa at 1 is Lys or Gly; Xaa at 2 is Ile or Phe;
      Xaa at 5 is Asp or Lys; Xaa at 6 is Ala, Gly or
      Asn;

<400> SEQUENCE: 195

```
Xaa Xaa Ser Tyr Xaa Xaa Leu
 1               5
```

<210> SEQ ID NO 196
<211> LENGTH: 4
<212> TYPE: PRT

-continued

<213> ORGANISM: Arabidopsis thaliana

<400> SEQUENCE: 196

Asn Ser His Arg
1

<210> SEQ ID NO 197

<400> SEQUENCE: 197

000

<210> SEQ ID NO 198
<211> LENGTH: 4
<212> TYPE: PRT
<213> ORGANISM: Arabidopsis thaliana

<400> SEQUENCE: 198

Thr Gly Asp Leu
1

<210> SEQ ID NO 199
<211> LENGTH: 4
<212> TYPE: PRT
<213> ORGANISM: Arabidopsis thaliana

<400> SEQUENCE: 199

His Gly Thr Tyr
1

<210> SEQ ID NO 200
<211> LENGTH: 11
<212> TYPE: PRT
<213> ORGANISM: Arabidopsis thaliana

<400> SEQUENCE: 200

Arg Met Ser His Gly Phe Arg Asn Ser Gln Ser
1               5                   10

<210> SEQ ID NO 201
<211> LENGTH: 27
<212> TYPE: PRT
<213> ORGANISM: Arabidopsis thaliana

<400> SEQUENCE: 201

Gly Glu Met Val Glu Ser Thr Gly Lys Arg Ser Thr Lys Arg Ala
1               5                   10                  15

Leu Leu Phe Thr Ala Leu Cys Ser Lys Leu Ile
            20                  25

<210> SEQ ID NO 202
<211> LENGTH: 9
<212> TYPE: PRT
<213> ORGANISM: Arabidopsis thaliana
<220> FEATURE:
<221> NAME/KEY: VARIANT
<222> LOCATION: (1)...(9)
<223> OTHER INFORMATION: Xaa at position 5 is Met or Asp

<400> SEQUENCE: 202

Pro Ile Phe Tyr Xaa Val Asp Pro Ser
1               5

<210> SEQ ID NO 203
<211> LENGTH: 6

```
<212> TYPE: PRT
<213> ORGANISM: Arabidopsis thaliana
<220> FEATURE:
<221> NAME/KEY: VARIANT
<222> LOCATION: (1)...(6)
<223> OTHER INFORMATION: Xaa at position 5 is Asp or Thr

<400> SEQUENCE: 203

Val Gly Ile Asp Xaa His
 1               5

<210> SEQ ID NO 204
<211> LENGTH: 9
<212> TYPE: PRT
<213> ORGANISM: Arabidopsis thaliana
<220> FEATURE:
<221> NAME/KEY: VARIANT
<222> LOCATION: (1)...(9)
<223> OTHER INFORMATION: Xaa at position 1 is Gln or Leu; Xaa at
      position 2 is Leu or Ile; Xaa at position 3 is Arg or Gln.

<400> SEQUENCE: 204

Met His Asp Xaa Xaa Xaa Asp Met Gly
 1               5

<210> SEQ ID NO 205
<211> LENGTH: 6
<212> TYPE: PRT
<213> ORGANISM: Arabidopsis thaliana

<400> SEQUENCE: 205

Ser Lys Leu Lys Ser Leu
 1               5

<210> SEQ ID NO 206
<211> LENGTH: 8
<212> TYPE: PRT
<213> ORGANISM: Arabidopsis thaliana
<220> FEATURE:
<221> NAME/KEY: VARIANT
<222> LOCATION: (1)...(8)
<223> OTHER INFORMATION: Xaa at position 3 is Arg or His; Xaa at
      position 7 is Ile or Tyr.

<400> SEQUENCE: 206

Gly Leu Xaa Ser Leu Glu Xaa Leu
 1               5

<210> SEQ ID NO 207
<211> LENGTH: 6
<212> TYPE: PRT
<213> ORGANISM: Arabidopsis thaliana

<400> SEQUENCE: 207

Ser Lys Leu Lys Ser Leu
 1               5

<210> SEQ ID NO 208
<211> LENGTH: 7
<212> TYPE: PRT
<213> ORGANISM: Arabidopsis thaliana

<400> SEQUENCE: 208

Lys Phe Ser Tyr Asp Asn Leu
 1               5

<210> SEQ ID NO 209
```

```
<211> LENGTH: 23
<212> TYPE: PRT
<213> ORGANISM: Arabidopsis Thalia
<220> FEATURE:
<221> NAME/KEY: VARIANT
<222> LOCATION: 2,3,5,6,8,9,11,12,14,16-9,21,22
<223> OTHER INFORMATION: Xaa=any amino acid
<220> FEATURE:
<221> NAME/KEY: VARIANT
<222> LOCATION: 4,15,20,23
<223> OTHER INFORMATION: Xaa=L or I or V

<400> SEQUENCE: 209

Pro Xaa Xaa Xaa Xaa Xaa Leu Xaa Xaa Leu Xaa Xaa Leu Xaa Xaa Xaa
 1               5                  10                  15

Xaa Xaa Xaa Xaa Xaa Xaa Xaa
            20

<210> SEQ ID NO 210
<211> LENGTH: 23
<212> TYPE: PRT
<213> ORGANISM: Yeast
<220> FEATURE:
<221> NAME/KEY: VARIANT
<222> LOCATION: 2,3,5,6,8,9,11,12,14,16,17,19,21,22
<223> OTHER INFORMATION: Xaa= any amino acid
<220> FEATURE:
<221> NAME/KEY: VARIANT
<222> LOCATION: 4,20,23
<223> OTHER INFORMATION: Xaa=L or I or V

<400> SEQUENCE: 210

Pro Xaa Xaa Xaa Xaa Xaa Leu Xaa Xaa Leu Xaa Xaa Leu Xaa Leu Xaa
 1               5                  10                  15

Xaa Asn Xaa Xaa Xaa Xaa Xaa
            20

<210> SEQ ID NO 211
<211> LENGTH: 12
<212> TYPE: PRT
<213> ORGANISM: Arabidopsis thaliana
<220> FEATURE:
<221> NAME/KEY: VARIANT
<222> LOCATION: 2,3,5,6,8,9,11
<223> OTHER INFORMATION: Xaa=any amino acid
<220> FEATURE:
<221> NAME/KEY: VARIANT
<222> LOCATION: 1
<223> OTHER INFORMATION: Xaa=I or L or V
<220> FEATURE:
<221> NAME/KEY: VARIANT
<222> LOCATION: 10
<223> OTHER INFORMATION: Xaa=I or L

<400> SEQUENCE: 211

Xaa Xaa Xaa Leu Xaa Xaa Leu Xaa Xaa Xaa Xaa Leu
 1               5                  10

<210> SEQ ID NO 212
<211> LENGTH: 7
<212> TYPE: PRT
<213> ORGANISM: Arabidopsis thaliana
<220> FEATURE:
<221> NAME/KEY: VARIANT
<222> LOCATION: 1
<223> OTHER INFORMATION: Xaa=I or R
<220> FEATURE:
<221> NAME/KEY: VARIANT
<222> LOCATION: 2,5-7
<223> OTHER INFORMATION: Xaa=any amino acid
```

```
-continued

<400> SEQUENCE: 212

Xaa Xaa Asp Leu Xaa Xaa Xaa
 1               5

<210> SEQ ID NO 213
<211> LENGTH: 8
<212> TYPE: PRT
<213> ORGANISM: Arabidopsis thaliana

<400> SEQUENCE: 213

Gly Pro Gly Gly Val Gly Lys Thr
 1               5

<210> SEQ ID NO 214
<211> LENGTH: 16
<212> TYPE: PRT
<213> ORGANISM: Arabidopsis thaliana

<400> SEQUENCE: 214

Thr Tyr Gly Ala Tyr Gly Ala Tyr Arg Thr Asx Tyr Arg Asx Arg Ala
 1               5                  10                  15
```

METHODS OF IDENTIFYING PLANT DISEASE-RESISTANCE GENES

CROSS REFERENCE TO RELATED APPLICATIONS

This application is a continuation of, and claims priority from, U.S. patent application Ser. No. 09/867,852 filed May 29, 2001 now abandoned, which is a continuation of U.S. Ser. No. 09/301,085, filed on Apr. 28, 1999 now U.S. Pat. No. 6,262,248, which is a divisional of U.S. Ser. No. 08/310,912, filed Sep. 22, 1994, now U.S. Pat. No. 5,981,730 which, in turn, is a continuation-in-part of U.S. patent application Ser. No. 08/227,360, filed Apr. 13, 1994 now abandoned.

This application is a continuation-in-part of application Ser. No. 08/227,360, filed Apr. 13, 1994.

STATEMENT AS TO FEDERALLY SPONSORED RESEARCH

This invention was made in part with Government funding and the Government therefore has certain rights in the invention.

BACKGROUND OF THE INVENTION

The invention relates to recombinant plant nucleic acids and polypeptides and uses thereof to confer disease resistance to pathogens in transgenic plants.

Plants employ a variety of defensive strategies to combat pathogens. One defense response, the so-called hypersensitive response (HR), involves rapid localized necrosis of infected tissue. In several host-pathogen interactions, genetic analysis has revealed a gene-for-gene correspondence between a particular avirulence (avr) gene in an avirulent pathogen that elicits an HR in a host possessing a particular resistance gene.

SUMMARY OF THE INVENTION

In general, the invention features substantially pure DNA (for example, genomic DNA, cDNA, or synthetic DNA) encoding an Rps polypeptide as defined below. In related aspects, the invention also features a vector, a cell (e.g., a plant cell), and a transgenic plant or seed thereof which includes such a substantially pure DNA encoding an Rps polypeptide.

In preferred embodiments, an RPS gene is the RPS2 gene of a plant of the genus *Arabidopsis*. In various preferred embodiments, the cell is a transformed plant cell derived from a cell of a transgenic plant. In related aspects, the invention features a transgenic plant containing a transgene which encodes an Rps polypeptide that is expressed in plant tissue susceptible to infection by pathogens expressing the avrRpt2 avirulence gene or pathogens expressing an avirulence signal similarly recognized by an Rps polypeptide.

In a second aspect, the invention features a substantially pure DNA which includes a promoter capable of expressing the RPS2 gene in plant tissue susceptible to infection by bacterial pathogens expressing the avrRpt2 avirulence gene.

In preferred embodiments, the promoter is the promoter native to an RPS gene. Additionally, transcriptional and translational regulatory regions are preferably native to an RPS gene.

The transgenic plants of the invention are preferably plants which are susceptible to infection by a pathogen expressing an avirulence gene, preferably the avrRpt2 avirulence gene. In preferred embodiments the transgenic plant is from the group of plants consisting of but not limited to *Arabidopsis*, tomato, soybean, bean, maize, wheat and rice.

In another aspect, the invention features a method of providing resistance in a plant to a pathogen which involves: (a) producing a transgenic plant cell having a transgene encoding an Rps2 polypeptide wherein the transgene is integrated into the genome of the transgenic plant and is positioned for expression in the plant cell; and (b) growing a transgenic plant from the transgenic plant cell wherein the RPS2 transgene is expressed in the transgenic plant.

In another aspect, the invention features a method of detecting a resistance gene in a plant cell involving: (a) contacting the RPS2 gene or a portion thereof greater than 9 nucleic acids, preferably greater than 18 nucleic acids in length with a preparation of genomic DNA from the plant cell under hybridization conditions providing detection of DNA sequences having about 50% or greater sequence identity to the DNA sequence of FIG. 2 encoding the Rps2 polypeptide.

In another aspect, the invention features a method of producing an Rps2 polypeptide which involves: (a) providing a cell transformed with DNA encoding an Rps2 polypeptide positioned for expression in the cell; (b) culturing the transformed cell under conditions for expressing the DNA; and (c) isolating the Rps2 polypeptide.

In another aspect, the invention features substantially pure Rps2 polypeptide. Preferably, the polypeptide includes a greater than 50 amino acid sequence substantially identical to a greater than 50 amino acid sequence shown in FIG. 2 open reading frame "a". Most preferably, the polypeptide is the *Arabidopsis thaliana* Rps2 polypeptide.

In another aspect, the invention features a method of providing resistance in a transgenic plant to infection by pathogens which do not carry the avrRpt2 avirulence gene wherein the method includes: (a) producing a transgenic plant cell having transgenes encoding an Rps2 polypeptide as well as a transgene encoding the avrRpt2 gene product wherein the transgenes are integrated into the genome of the transgenic plant; are positioned for expression in the plant cell; and the avrRpt2 transgene and, if desired, the RPS2 gene, are under the control of regulatory sequences suitable for controlled expression of the gene(s); and (b) growing a transgenic plant from the transgenic plant cell wherein the RPS2 and avrRpt2 transgenes are expressed in the transgenic plant.

In another aspect, the invention features a method of providing resistance in a transgenic plant to infection by pathogens in the absence of avirulence gene expression in the pathogen wherein the method involves: (a) producing a transgenic plant cell having integrated in the genome a transgene containing the RPS2 gene under the control of a promoter providing constitutive expression of the RPS2 gene; and (b) growing a transgenic plant from the transgenic plant cell wherein the RPS2 transgene is expressed constitutively in the transgenic plant.

In another aspect, the invention features a method of providing controllable resistance in a transgenic plant to infection by pathogens in the absence of avirulence gene expression in the pathogen wherein the method involves: (a) producing a transgenic plant cell having integrated in the genome a transgene containing the RPS2 gene under the control of a promoter providing controllable expression of the RPS2 gene; and (b) growing a transgenic plant from the transgenic plant cell wherein the RPS2 transgene is controllably expressed in the transgenic plant. In preferred embodiments, the RPS2 gene is expressed using a tissue-specific or cell type-specific promoter, or by a promoter that is activated by the introduction of an external signal or agent, such as a chemical signal or agent.

In other aspects, the invention features a substantially pure oligonucleotide including one or a combination of the sequences:

5' GGNATGGGNGGNNTNGGNAARACNAC 3' (SEQ ID NO:158), wherein N is A, T, G, or C; and R is A or G;

5' NARNGGNARNCC 3' (SEQ ID NO:169), wherein N is A, I, G or C; and R is A or G;

5'NCGNGWNGTNAKDAWNCGNGA 3' (SEQ ID NO:159), wherein N is A, T, G or C; W is A or T; D is A, G, or T; and K is G or T;

5' GGWNTBGGWAARACHAC 3' (SEQ ID NO:160), wherein N is A, T, G or C; R is G or A; B is C, G, or T; H is A, C, or T; and W is A or T;

5' TYGAYGAYRTBKRBRA 3' (SEQ ID NO:163), wherein R is G or A; B is C, G, or T; D is A, G, or T; Y is T or C; and K is G or T;

5' TYCCAVAYRTCRTCNA 3' (SEQ ID NO:164), wherein N is A, T, G or C; R is G or A; V is G or C or A; and Y is T or C;

5' GGWYTBCCWYTBGCHYT 3' (SEQ ID NO:170), wherein B is C, G, or T; H is A, C, or T; W is A or T; and Y is T or C;

5' ARDGCVARWGGVARNCC 3' (SEQ ID NO:171), wherein N is A, T, G or C; R is G or A; W is A or T; D is A, G, or T; and V is G, C, or A; and 5' ARRTTRTCRTADSWRAWYTT 3' (SEQ ID NO:174), wherein R is G or A; W is A or T; D is A, G, or T; S is G or C; and Y is C or T.

In other aspects, the invention features a recombinant plant gene including one or a combination of the DNA sequences:

5' GGNATGGGNGGNNTNGGNAARACNAC 3' (SEQ ID NO:158), wherein N is A, T, G or C; and R is A or G;

5' NARNGGNARNCC 3' (SEQ ID NO:169), wherein N is A, T, G or C; and R is A or G;

5' NCGNGWNGTNAKDAWNCGNGA 3' (SEQ ID NO:167), wherein N is A, T, G or C; W is A or T; D is A, G or T; and K is G or T.

In another aspect, the invention features a substantially pure plant polypeptide including one or a combination of the amino acid sequences:

Gly Xaa$_1$ Xaa$_2$ Gly Xaa$_3$ Gly Lys Thr Thr Xaa$_4$ Xaa$_5$ (SEQ ID NO:191), wherein Xaa$_1$ is Met or Pro; Xaa$_2$ is Gly or Pro; Xaa$_3$ is Ile, Leu, or Val; Xaa$_4$ is Ile, Leu, or Thr; and Xaa$_5$ is Ala or Met;

Xaa$_1$ Xaa$_2$ Xaa$_3$ Leu Xaa$_4$ Xaa$_5$ Xaa$_6$ Asp Asp Xaa$_7$ Xaa$_8$ (SEQ ID NO:192), wherein Xaa$_1$ is Phe or Lys; Xaa$_2$ is Arg or Lys; Xaa$_3$ is Ile, Val, or Phe; Xaa$_4$ is Ile, Leu, or Val; Xaa$_5$ is Ile or Leu; Xaa$_6$ is Ile or Val; Xaa$_7$ is Ile, Leu, or Val; and Xaa$_8$ is Asp or Trp;

Xaa$_1$ Xaa$_2$ Xaa$_3$ Xaa$_4$ Xaa$_5$ Thr Xaa$_6$ Arg (SEQ ID NO:193), wherein Xaa$_1$ is Ser or Cys; Xaa$_2$ is Arg or Lys; Xaa$_3$ is Phe, Ile, or Val; Xaa$_4$ is Ile, or Met; Xaa$_5$ is Ile, Leu, or Phe; Xaa$_6$ is Ser, Cys, or Thr;

Gly Leu Pro Leu Xaa$_1$ Xaa$_2$ Xaa$_3$ Xaa$_4$ (SEQ ID NO:194), wherein Xaa$_1$ is Thr, Ala, or Ser; Xaa$_2$ is Leu or Val; Xaa$_3$ is Ile, Val, or Lys; and Xaa$_4$ is Val or Thr; and Xaa$_1$ Xaa$_2$ Ser Tyr Xaa$_3$ Xaa$_4$ Leu (SEQ ID NO:195), wherein Xaa$_1$ is Lys or Gly; Xaa$_2$ is Ile or Phe; Xaa$_3$ is Asp or Lys; and Xaa$_4$ is Ala, Gly, or Asn.

In another aspect, the invention features a method of isolating a disease-resistance gene or fragment thereof from a plant cell, involving: (a) providing a sample of plant cell DNA; (b) providing a pair of oligonucleotides having sequence homology to a conserved region of an RPS disease-resistance gene; (c) combining the pair of oligonucleotides with the plant cell DNA sample under conditions suitable for polymerase chain reaction-mediated DNA amplification; and (d) isolating the amplified disease-resistance gene or fragment thereof.

In preferred embodiments, the amplification is carried out using a reverse-transcription polymerase chain reaction, for example, the RACE method In another aspect, the invention features a method of identifying a plant disease-resistance gene in a plant cell, involving: (a) providing a preparation of plant cell DNA (for example, from the plant genome); (b) providing a detectably-labelled DNA sequence (for example, prepared by the methods of the invention) having homology to a conserved region of an RPS gene; (c) contacting the preparation of plant cell DNA with the detectably-labelled DNA sequence under hybridization conditions providing detection of genes having 50% or greater sequence identity; and (d) identifying a disease-resistance gene by its association with the detectable label.

In another aspect, the invention features a method of isolating a disease-resistance gene from a recombinant plant cell library, involving: (a) providing a recombinant plant cell library; (b) contacting the recombinant plant cell library with a detectably-labelled gene fragment produced according to the PCR method of the invention under hybridization conditions providing detection of genes having 50% or greater sequence identity; and (c) isolating a member of a disease-resistance gene by its association with the detectable label.

In another aspect, the invention features a method of isolating a disease-resistance gene from a recombinant plant cell library, involving: (a) providing a recombinant plant cell library; (b) contacting the recombinant plant cell library with a detectably-labelled RPS oligonucleotide of the invention under hybridization conditions providing detection of genes having 50% or greater sequence identity; and (c) isolating a disease-resistance gene by its association with the detectable label.

In another aspect, the invention features a recombinant plant polypeptide capable of conferring disease-resistance wherein the plant polypeptide includes a P-loop domain or nucleotide binding site domain. Preferably, the polypeptide further includes a leucine-rich repeating domain.

In another aspect, the invention features a recombinant plant polypeptide capable of conferring disease-resistance wherein the plant polypeptide contains a leucine-rich repeating domain.

In another aspect, the invention features a plant disease-resistance gene isolated according to the method involving: (a) providing a sample of plant cell DNA; (b) providing a pair of oligonucleotides having sequence homology to a conserved region of an RPS disease-resistance gene; (c) combining the pair of oligonucleotides with the plant cell DNA sample under conditions suitable for polymerase chain reaction-mediated DNA amplification; and (d) isolating the amplified disease-resistance gene or fragment thereof.

In another aspect, the invention features a plant disease-resistance gene isolated according to the method involving: (a) providing a preparation of plant cell DNA; (b) providing a detectably-labelled DNA sequence having homology to a conserved region of an RPS gene; (c) contacting the preparation of plant cell DNA with the detectably-labelled DNA sequence under hybridization conditions providing detection of genes having 50% or greater sequence identity; and (d) identifying a disease-resistance gene by its association with the detectable label.

In another aspect, the invention features a plant disease-resistance gene according to the method involving: (a) providing a recombinant plant cell library; (b) contacting the recombinant plant cell library with a detectably-labelled RPS gene fragment produced according to the method of the invention under hybridization conditions providing detection of genes having 50% or greater sequence identity; and (c) isolating a disease-resistance gene by its association with the detectable label.

In another aspect, the invention features a method of identifying a plant disease-resistance gene involving: (a) providing a plant tissue sample; (b) introducing by biolistic transformation into the plant tissue sample a candidate plant disease-resistance gene; (c) expressing the candidate plant disease-resistance gene within the plant tissue sample; and (d) determining whether the plant tissue sample exhibits a disease-resistance response, whereby a response identifies a plant disease-resistance gene.

Preferably, the plant tissue sample is either leaf, root, flower, fruit, or stem tissue; the candidate plant disease-resistance gene is obtained from a cDNA expression library; and the disease-resistance response is the hypersensitive response.

In another aspect, the invention features a plant disease-resistance gene isolated according to the method involving: (a) providing a plant tissue sample; (b) introducing by biolistic transformation into the plant tissue sample a candidate plant disease-resistance gene; (c) expressing the candidate plant disease-resistance gene within the plant tissue sample; and (d) determining whether the plant tissue sample exhibits a disease-resistance response, whereby a response identifies a plant disease-resistance gene.

In another aspect, the invention features a purified antibody which binds specifically to an rps family protein. Such an antibody may be used in any standard immunodetection method for the identification of an RPS polypeptide.

In another aspect, the invention features a DNA sequence substantially identical to the DNA sequence shown in FIG. 12.

In another aspect, the invention features a substantially pure polypeptide having a sequence substantially identical to a Prf amino acid sequence shown in FIG. 5 (A or B).

By "disease resistance gene" is meant a gene encoding a polypeptide capable of triggering the plant defense response in a plant cell or plant tissue. An RPS gene is a disease resistance gene having about 50% or greater sequence identity to the RPS2 sequence of FIG. 2 or a portion thereof. The gene, RPS2, is a disease resistance gene encoding the Rps2 disease resistance polypeptide from *Arabidopsis thaliana*.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant an Rps2 polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, Rps2 polypeptide. A substantially pure Rps2 polypeptide may be obtained, for example, by extraction from a natural source (e.g., a plant cell); by expression of a recombinant nucleic acid encoding an Rps2 polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an Rps2 polypeptide.

By "positioned for expression" is meant that the DNA molecule is positioned adjacent to a DNA sequence which directs transcription and translation of the sequence (i.e., facilitates the production of, e.g., an Rps2 polypeptide, a recombinant protein or a RNA molecule).

By "reporter gene" is meant a gene whose expression may be assayed; such genes include, without limitation, β-glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen, and microspores.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into the nuclear or plastidic genome.

By "pathogen" is meant an organism whose infection into the cells of viable plant tissue elicits a disease response in the plant tissue.

By an "RPS disease-resistance gene" is meant any member of the family of plant genes characterized by their ability to trigger a plant defense response and having at least 20%, preferably 30%, and most preferably 50% amino acid sequence identity to one of the conserved regions of one of the RPS members described herein (i.e., either the RPS2, L6, N, or Prf genes). Representative members of the RPS gene family include, without limitation, the rps2 gene of *Arabidopsis*, the L6 gene of flax, the Prf gene of tomato, and the N gene of tobacco.

By "conserved region" is meant any stretch of six or more contiguous amino acids exhibiting at least 30%, preferably 50%, and most preferably 70% amino acid sequence identity between two or more of the RPS family members, RPS2, L6, N, or Prf. Examples of preferred conserved regions are shown (as boxed or designated sequences) in FIGS. 5A and B, 6, 7, and 8 and include, without limitation, nucleotide binding site domains, leucine-rich repeats, leucine zipper domains, and P-loop domains.

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling).

By "biolistic transformation" is meant any method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., chloroplasts and mitochondria), bacteria, yeast, fungi, algae, pollen, animal tissue, plant tissue (e.g., leaf, seedling, embryo, epidermis, flower, meristem, and root), pollen, and cultured cells.

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., an rps2-specific antibody. A purified rps antibody may be obtained, for example, by affinity chromatography using recombinantly-produced rps protein or conserved motif peptides and standard techniques.

By "specifically binds" is meant an antibody which recognizes and binds an rps protein but which does not substantially recognize and bind other molecules in a sample, e.g., a biological sample, which naturally includes rps protein.

Other features and advantages of the invention will be apparent from the following description of the preferred embodiments thereof, and from the claims.

DETAILED DESCRIPTION

The drawings will first be described.

DRAWINGS

FIGS. 1A–1F are a schematic summary of the physical and RFLP analysis that led to the cloning of the RPS2 locus.

FIG. 1A is a diagram showing the alignment of the genetic and the RFLP maps of the relevant portion of *Arabidopsis thaliana* chromosome IV adapted from the map published by Lister and Dean (1993) Plant J. 4:745–750. The RFLP marker L11F11 represents the left arm of the YUP11F11 YAC clone.

FIG. 1B is a diagram showing the alignment of relevant YACs around the RPS2 locus. YAC constructs designated YUP16G5, YUP18G9 and YUP11F11 were provided by J. Ecker, University of Pennsylvania. YAC constructs designated EW3H7, EW11D4, EW11E4, and EW9C3 were provided by E. Ward, Ciba-Geigy, Inc.

FIG. 1C is a diagram showing the alignment of cosmid clones around the RPS2 locus. Cosmid clones with the designation H are derivatives of the EW3H7 YAC clone whereas those with the designation E are derivatives of the EW11E4 YAC clone. Vertical arrows indicate the relative positions of RFLP markers between the ecotypes La-er and the rps2-101N plant. The RFLP markers were identified by screening a Southern blot containing more than 50 different restriction enzyme digests using either the entire part or pieces of the corresponding cosmid clones as probes. The cosmid clones described in FIG. 1C were provided by J. Giraudat, C.N.R.S., Gif-sur-Yvette, France.

FIGS. 1D and 1E are maps of EcoRI restriction endonuclease sites in the cosmids E4-4 and E4-6, respectively. The recombination break points surrounding the RPS2 locus are located within the 4.5 and 7.5 kb EcoRI restriction endonuclease fragments.

FIG. 1F is a diagram showing the approximate location of genes which encode the RNA transcripts which have been identified by polyA$^+$ RNA blot analysis. The sizes of the transcripts are given in kilobase pairs below each transcript.

Figure 2F:
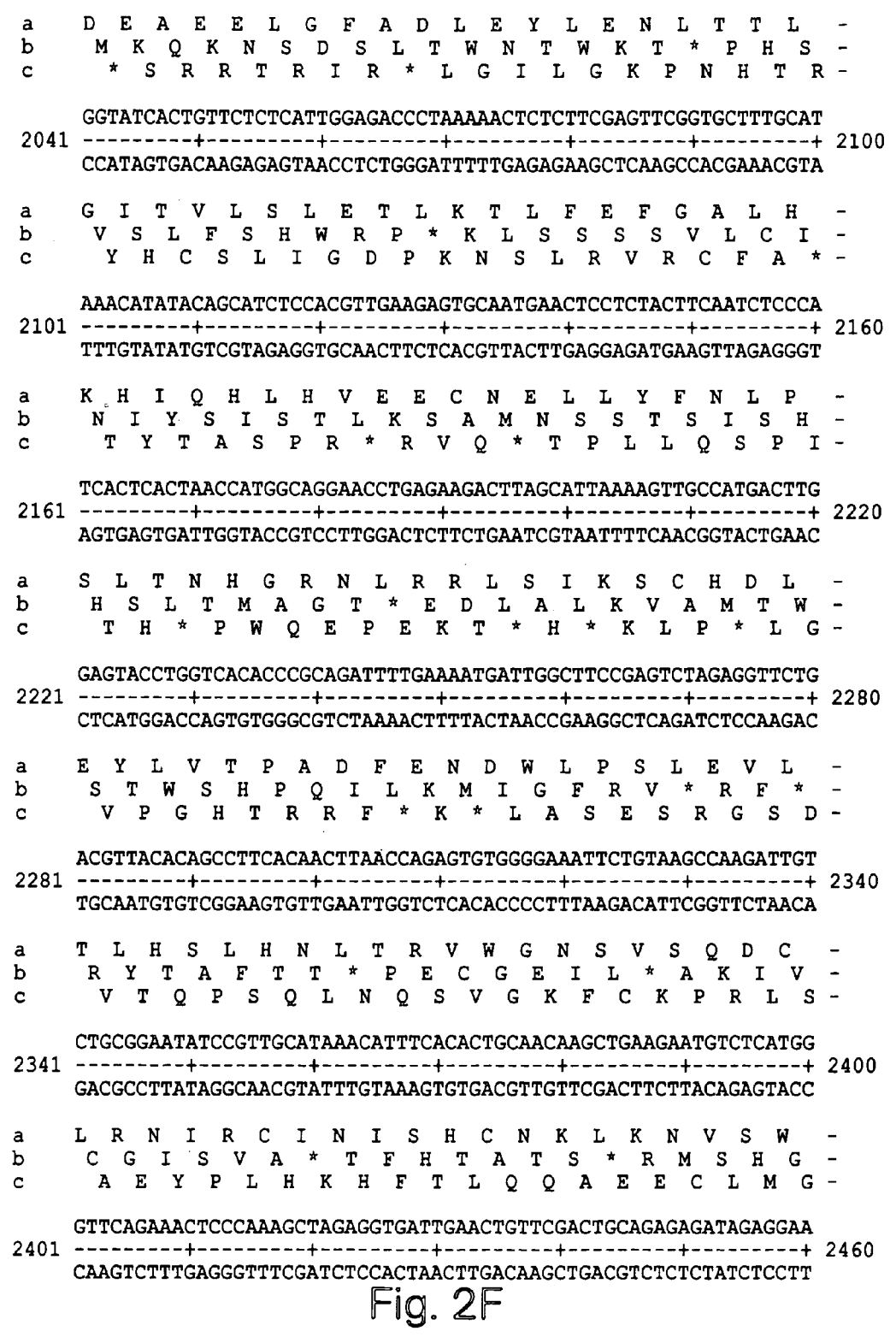

FIG. 2 is the complete nucleotide sequence of cDNA-4 comprising the RPS2 gene locus (SEQ ID NO:1). The three reading frames are shown below the nucleotide sequence (SEQ ID NOS:2–104, 196, and 198–200). The deduced amino acid sequence of reading frame "a" is provided and contains 909 amino acids. The methionine encoded by the ATG start codon is circled in open reading frame "a" of FIG. 2 (SEQ ID NOS:2–5). The A of the ATG start codon is nucleotide 31 of FIG. 2 (SEQ ID NO:1).

FIG. 3 is the nucleotide sequence of the avrRpt2 gene (SEQ ID NO:105) and its deduced amino acid sequence (SEQ ID NO:106). A potential ribosome binding site is underlined. An inverted repeat is indicated by horizontal arrows at the 3' end of the open reading frame. The deduced amino acid sequence is provided below the nucleotide sequence of the open reading frame (SEQ ID NOS:105 and 106).

Figure 4:
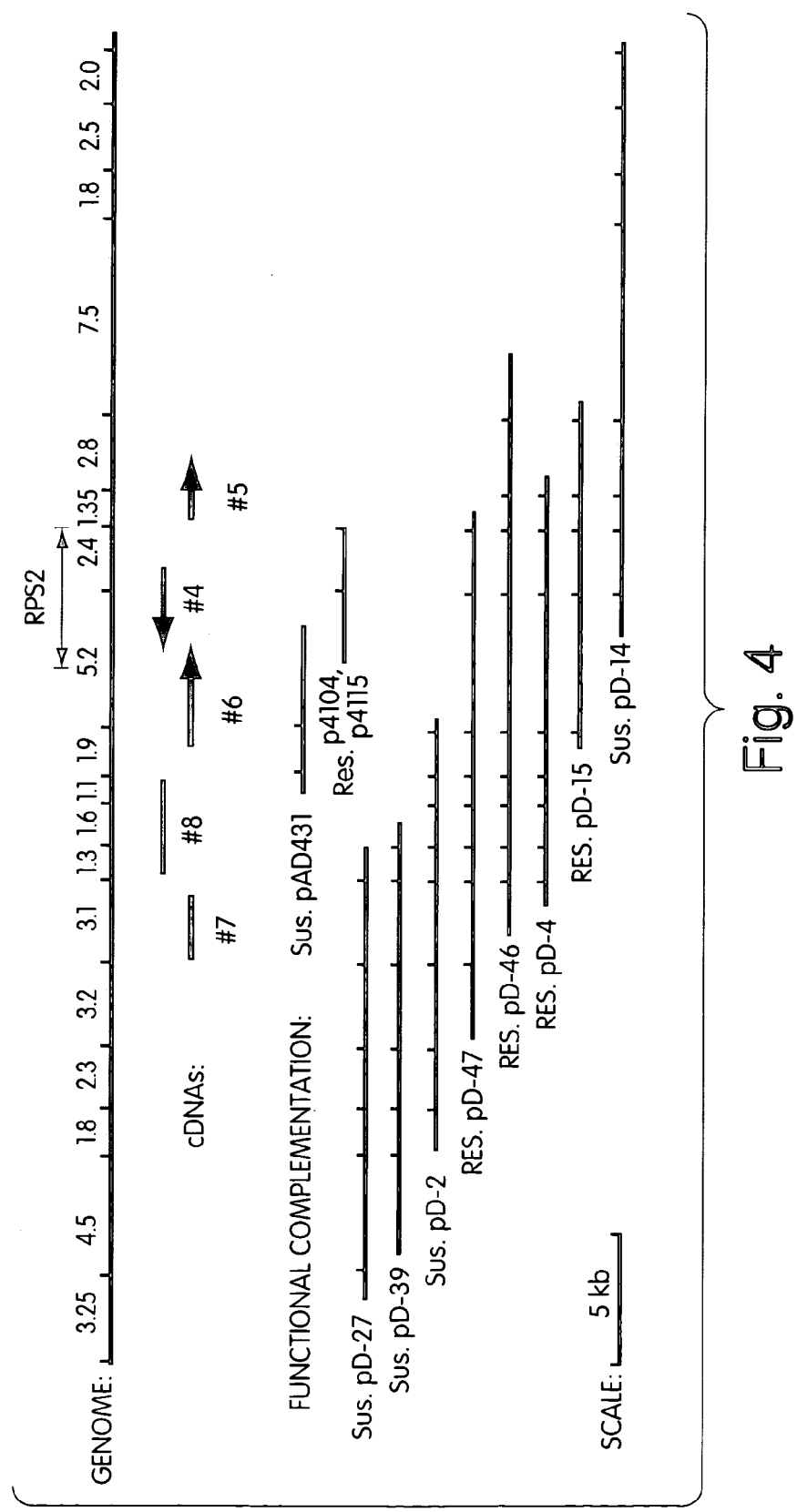

FIG. 4 is a schematic summary of the complementation analysis that allowed functional confirmation that the DNA carried on p4104 and p4115 (encoding cDNA-4) confers RPS2 disease resistance activity to *Arabidopsis thaliana* plants previously lacking RPS2 disease resistance activity. Small vertical marks along the "genome" line represent restriction enzyme EcoRI recognition sites, and the numbers above this line represent the size, in kilobase pairs (kb), of the resulting DNA fragments (see also FIG. 1E). Opposite "cDNAs" are the approximate locations of the coding sequences for RNA transcripts (See also FIG. 1F); arrowheads indicate the direction of transcription for cDNAs 4, 5, and 6. For functional complementation experiments, rps2-201C/zps2-201C plants were genetically transformed with the *Arabidopsis thaliana* genomic DNA sequences indicated; these sequences were carried on the named plasmids (derivatives of the binary cosmid vector pSLJ4541) and delivered to the plant via *Agrobacterium*-mediated transformation methods. The disease resistance phenotype of the resulting transformants following inoculation with *P. syringae* expressing avrRpt2 is given as "Sus." (susceptible, no resistance response) or "Res." (disease resistant).

FIG. 5A shows regions of sequence similarity between the L-6 protein of flax, N protein of tobacco, Prf protein of tomato, and rps2 protein of *Arabidopsis* (SEQ ID NOS:2, 107–136, 142, and 208).

FIG. 5B shows sequence similarity between the N and L-6 proteins (SEQ ID NOS:107, 108, 129–136, 138–140, and 207).

FIG. 6 shows a sequence analysis of RPS2 polypeptide showing polypeptide regions corresponding to an N-terminal hydrophobic region, a leucine zipper, NBSs (kinase-1a, kinase-2, and kinase-3 motifs), and a predicted membrane integrated region (SEQ ID NOS:141 and 142).

FIG. 7 shows the amino acid sequence of the RPS2 LRR (amino acids 505–867) (SEQ ID NOS:143–156). The top line indicates the consensus sequences for the RPS2 LRR (SEQ ID NO:209). An "X" stands for an arbitrary amino acid sequence and an "a" stands for an aliphatic amino acid residue. The consensus sequence for the RPS2 LRR is closely related to the consensus for the yeast adenylate cyclase CYR1 LRR (PX Xa XXL XXL XXLXL XXNX-aXXa) (SEQ ID NO:210). The amino acid residues that match the consensus sequence are shown in bold. Although this figure shows 14 LRRs, the C-terminal boundary of the LRR is not very clear because the LRR closer to the C-terminus does not fit the consensus sequence very well.

FIG. 8 shows a sequence analysis of RPS2 (SEQ ID NO:142), indicating regions with similarity to leucine zipper, P-loop, membrane-spanning, and leucine-rich repeat motifs. Regions with similarity to defined functional domains are indicated with a line over the relevant amino acids. Potential N-glycosylation sequences are marked with a dot, and the location of the rps2-201 Thr to Pro mutation at amino acid 668 is marked with an asterisk.

Figure 9:
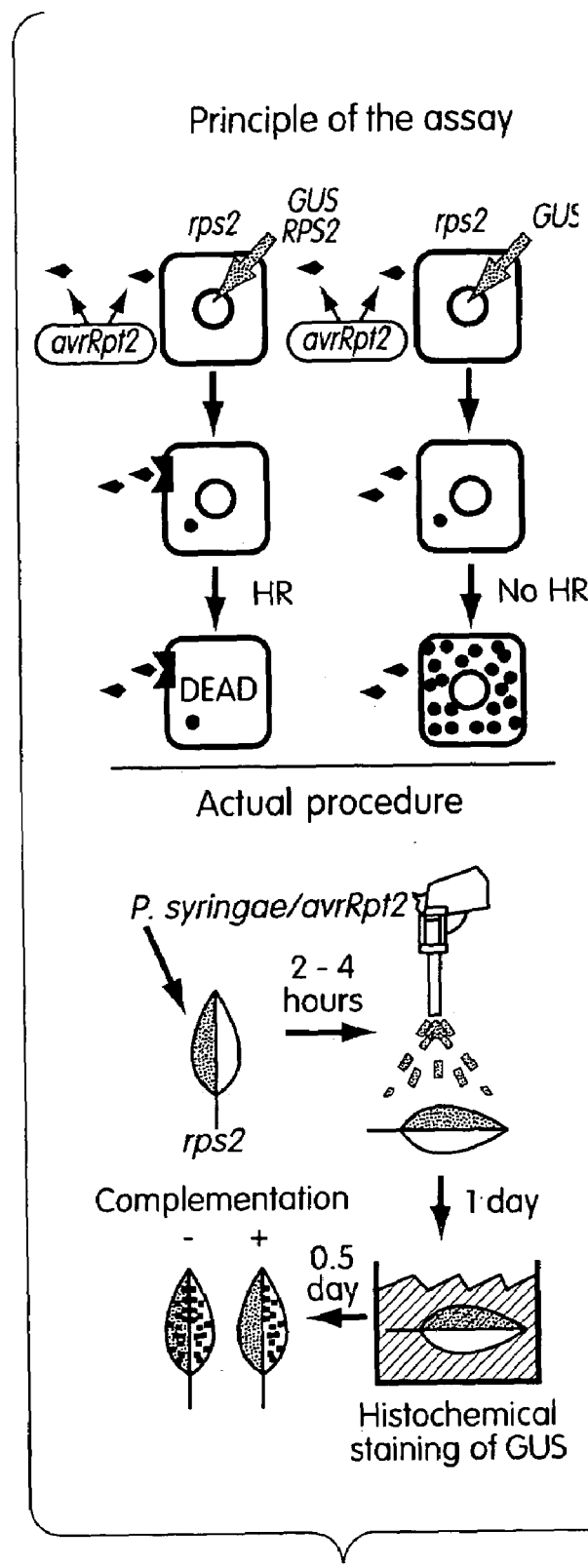

FIG. 9 is a schematic representation of the transient assay method. The top panel shows the essential principles of the assay. The bottom panel shows a schematic representation of the actual transient assay procedure. Psp NP53121 is used because it is a weak *Arabidopsis* pathogen, but potent in causing the HR when carrying an avirulence gene. In the absence of an HR, the damage to plant cells infected with NP53121 is minimal, enhancing the difference of GUS accumulation in cells that undergo the HR in comparison to those that do not. Prior to bombardment, one half of an *Arabidopsis* leaf is infiltrated with *P. syringae* (stippled side of leaf); the other half of the leaf serves as a noninfected control, an "internal" reference for the infected side, and as a measure of transformation efficiency.

Figure 10B:
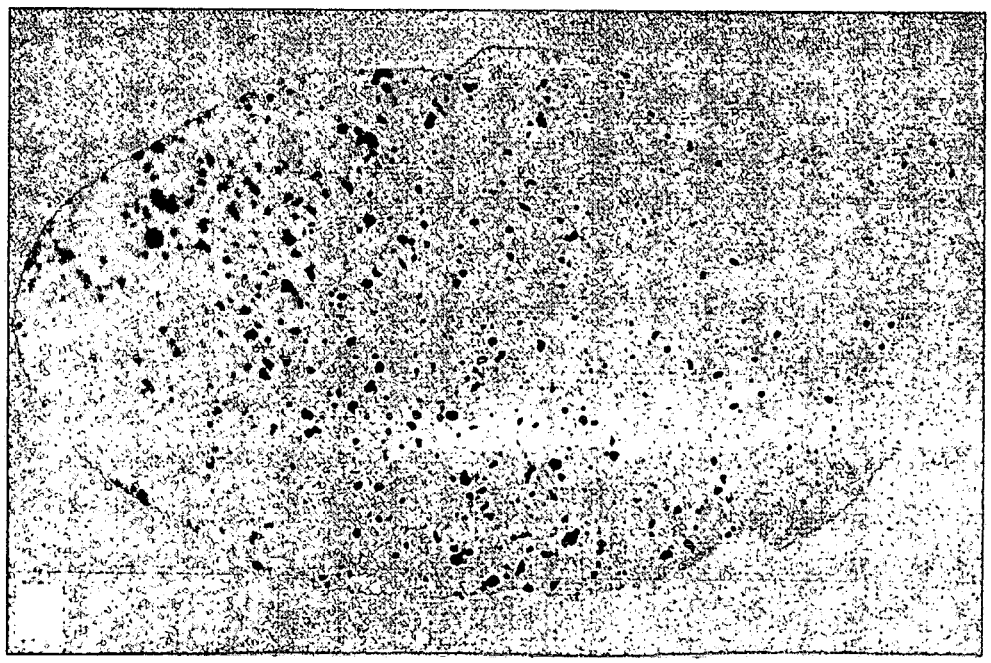
Figure 10A:
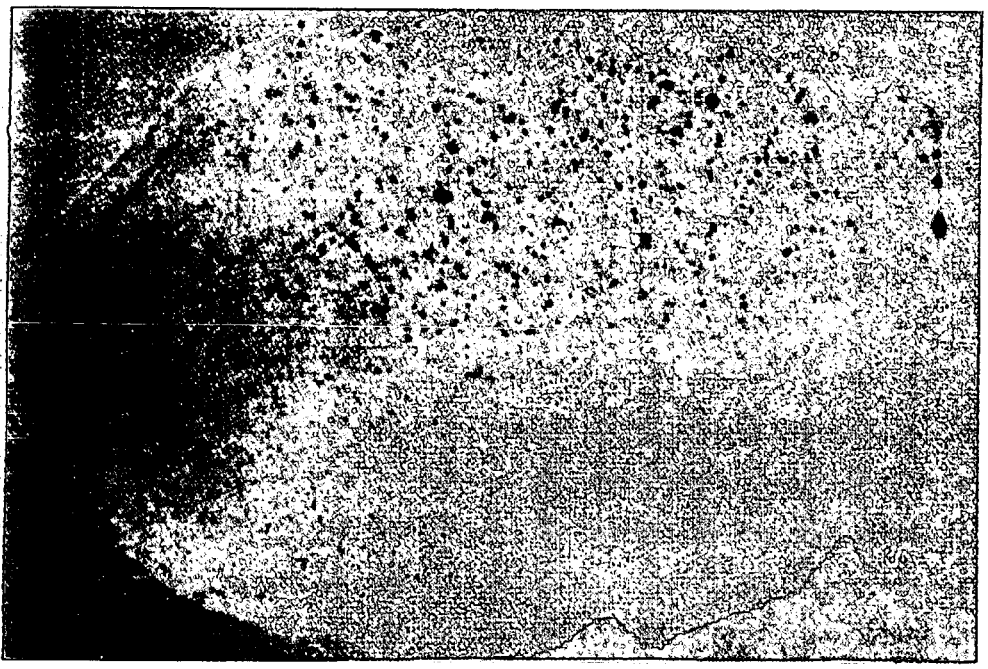

FIG. 10, panels A–B, are photographs showing the complementation of the rps2 mutant phenotype using the biolistic transient expression assay. The left sides of rps2-101C mutant leaves were infiltrated with Psp 3121/avrRpt2. Infiltrated leaves were cobombarded with either 35S-uidA plus ΔGUS (Panel A) or 35S-uidA plus 35S-RPS2 (cDNA-2 clone 4) (Panel B). Note that in Panel B the infected side of the leaf shows less GUS activity than the uninfected side, indicating that the transformed cells on the infected side underwent an HR and that 35S-RPS2 complemented the mutant phenotype (see FIG. 9).

Figure 11:
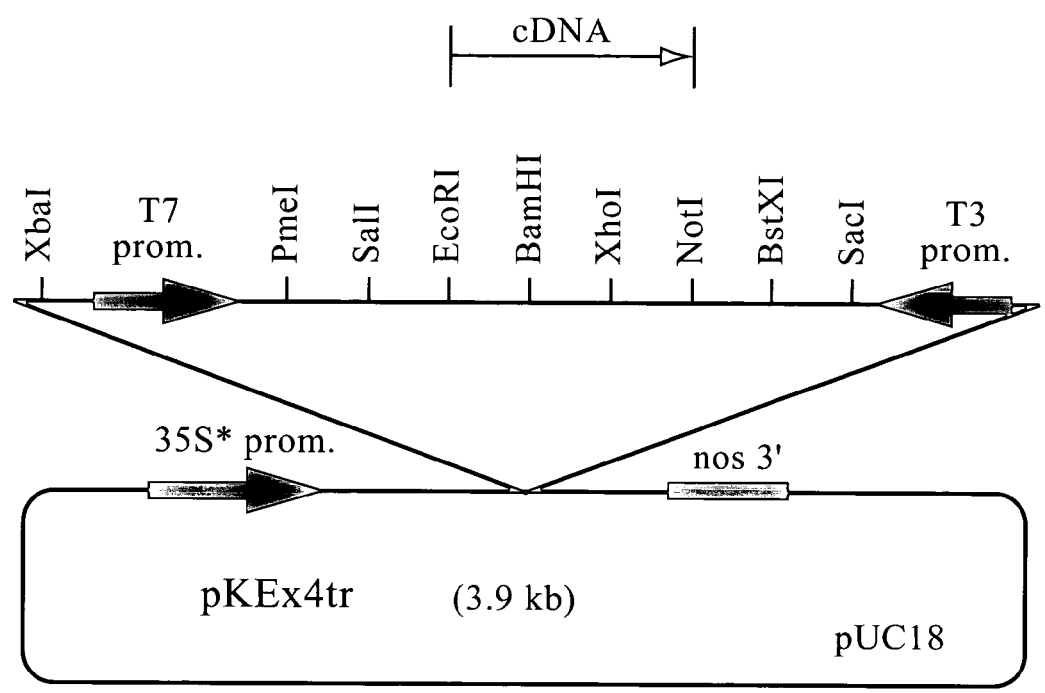

FIG. 11 is a schematic representation of pKEx4tr showing the structure of this cDNA expression vector. For convenience, the multiple cloning site contains the 8 bp recognition sequences for PmeI and NotI and is flanked by T7 and T3 promoters. The region spanning the modified 35S promoter to the nopaline synthase 3' sequences (nos 3') was cloned into the Hind III-EcoRI site of pUC18, resulting in the loss of the EcoRI site.

FIG. 12 shows a nucleic acid sequence of the tomato Prf gene (SEQ ID NO:157).

THE GENETIC BASIS FOR RESISTANCE TO PATHOGENS

An overview of the interaction between a plant host and a microbial pathogen is presented. The invasion of a plant by a potential pathogen can have a range of outcomes delineated by the following outcomes: either the pathogen successfully proliferates in the host, causing associated disease symptoms, or its growth is halted by the host defenses. In some plant-pathogen interactions, the visible hallmark of an active defense response is the so-called hypersensitive response or "HR". The HR involves rapid necrosis of cells near the site of the infection and may include the formation of a visible dry brown lesion. Pathogens which elicit an HR on a given host are said to be avirulent on that host, the host is said to be resistant, and the plant-pathogen interaction is said to be incompatible. Strains which proliferate and cause disease on a particular host are said to be virulent; in this case the host is said to be susceptible, and the plant-pathogen interaction is said to be compatible "Classical" genetic analysis has been used successfully to help elucidate the genetic basis of plant-pathogen recognition for those cases in which a series of strains (races) of a particular fungal or bacterial pathogen are either virulent or avirulent on a series of cultivars (or different wild accessions) of a particular host species. In many such cases, genetic analysis of both the host and the pathogen revealed that many avirulent fungal and bacterial strains differ from virulent ones by the possession of one or more avirulence (avr) genes that have corresponding "resistance" genes in the host. This avirulence gene-resistance gene correspondence is termed the "gene-for-gene" model (Crute, et al., (1985) pp 197–309 in: *Mechanisms of Resistance to Plant Disease*. R. S. S. Fraser, ed.; Ellingboe, (1981) Annu. Rev. Phytopathol. 19:125–143; Flor, (1971) Annu. Rev. Phytopathol. 9:275–296; Keen and Staskawicz, (1988) supra; and Keen et al. in: *Application of Biotechnology to Plant Pathogen Control*. I. Chet, ed., John Wiley & Sons, 1993, pp. 65–88). According to a simple formulation of this model, plant resistance genes encode specific receptors for molecular signals generated by avr genes. Signal transduction pathway(s) then carry the signal to a set of target genes that initiate the HR and other host defenses (Gabriel and Rolfe, (1990) Annu. Rev. Phytopathol. 28:365–391). Despite this simple predictive model, the molecular basis of the avr-resistance gene interaction is still unknown.

One basic prediction of the gene-for-gene hypothesis has been convincingly confirmed at the molecular level by the cloning of a variety of bacterial avr genes (Innes, et al., (1993) J. Bacteriol. 175:4859–4869; Dong, et al., (1991) Plant Cell 3:61–72; Whelan et al., (1991) Plant Cell 3:49–59; Staskawicz et al., (1987) J. Bacteriol. 169:5789–5794; Gabriel et al., (1986) P.N.A.S., USA 83:6415–6419; Keen and Staskawicz, (1988) Annu. Rev. Microbiol. 42:421–440; Kobayashi et al., (1990) Mol. Plant-Microbe Interact. 3:94–102 and (1990) Mol. Plant-Microbe Interact. 3:103–111). Many of these cloned avirulence genes have been shown to correspond to individual resistance genes in the cognate host plants and have been shown to confer an avirulent phenotype when transferred to an otherwise virulent strain. The avrRpt2 locus was isolated from *Pseudomonas syringae* pv. tomato and sequenced by Innes et al. (Innes, R. et al. (1993) J. Bacteriol. 175:4859–4869). FIG. 3 is the nucleotide sequence and deduced amino acid sequence of the avrRpt2 gene.

Examples of known signals to which plants respond when infected by pathogens include harpins from *Erwinia* (Wei et al. (1992) Science 257:85–88) and *Pseudomonas* (He et al. (1993) Cell 73:1255–1266); avr4 (Joosten et al. (1994) Nature 367:384–386) and avr9 peptides (van den Ackerveken et al (1992) Plant J. 2:359–366) from *Cladosporium*; PopA1 from *Pseudomonas* (Arlat et al. (1994) EMBO J. 13:543–553); avrD-generated lipopolysaccharide (Midland et al. (1993) J. Org. Chem. 58:2940–2945); and NIP1 from *Rhynchosporium* (Hahn et al. (1993) Mol. Plant-Microbe Interact. 6:745–754).

Compared to avr genes, considerably less is known about plant resistance genes that correspond to specific avr-generated signals. The plant resistance gene, RPS2 (rps for resistance to *Pseudomonas syringae*), the first gene of a new, previously unidentified class of plant disease resistance genes corresponds to a specific avr gene (avrRpt2). Some of the work leading up to the cloning of RPS2 is described in Yu, et al., (1993), Molecular Plant-Microbe Interactions 6:434–443 and in Kunkel, et al., (1993) Plant Cell 5:865–875.

An apparently unrelated avirulence gene which corresponds specifically to plant disease resistance gene, Pto, has been isolated from tomato (*Lycopersicon esculentum*) (Martin et al., (1993) Science 262:1432–1436). Tomato plants expressing the Pto gene are resistant to infection by strains of *Pseudomonas syringae* pv. tomato that express the avrPto avirulence gene. The amino acid sequence inferred from the Pto gene DNA sequence displays strong similarity to serine-threonine protein kinases, implicating Pto in signal transduction. No similarity to the tomato Pto locus or any known protein kinases was observed for RPS2, suggesting that RPS2 is representative of a new class of plant disease resistance genes.

The isolation of a race-specific resistance gene from *Zea mays* (corn) known as Hm1 has been reported (Johal and Briggs (1992) Science 258:985–987). Hm1 confers resistance against specific races of the fungal pathogen *Cochliobolus carbonum* by controlling degradation of a fungal toxin, a strategy that is mechanistically distinct from the avirulence-gene specific resistance of the RPS2-avrRpt2 resistance mechanism.

The cloned RPS2 gene of the invention can be used to facilitate the construction of plants that are resistant to specific pathogens and to overcome the inability to transfer disease resistance genes between species using classical breeding techniques (Keen et al., (1993), supra). There now follows a description of the cloning and characterization of an *Arabidopsis thaliana* RPS2 genetic locus, the RPS2 genomic DNA, and the RPS2 cDNA. The avrRpt2 gene and the RPS2 gene, as well as mutants rps2-101C, rps2-102C, and rps2-201C (also designated rps2-201), are described in Dong, et al., (1991) Plant Cell 3:61–72; Yu, et al., (1993) supra; Kunkel et al., (1993) supra; Whalen et al., (1991), supra; and Innes et al., (1993), supra). A mutant designated rps2-101N has also been isolated. The identification and cloning of the RPS2 gene is described below.

RPS2 Overcomes Sensitivity to Pathogens Carrying the avrRpt2 Gene

To demonstrate the genetic relationship between an avirulence gene in the pathogen and a resistance gene in the host, it was necessary first to isolate an avirulence gene. By screening *Pseudomonas* strains that are known pathogens of crop plants related to *Arabidopsis*, highly virulent strains, *P. syringae* pv. maculicola (Psm) ES4326, *P. syringae* pv. tomato (Pst) DC3000, and an avirulent strain, Pst MM1065 were identified and analyzed as to their respective abilities to grow in wild type *Arabidopsis thaliana* plants (Dong et al., (1991) Plant Cell, 3:61–72; Whalen et al., (1991) Plant Cell 3:49–59; MM1065 is designated JL1065 in Whalen et al.). Psm ES4326 or Pst DC3000 can multiply $10^4$ fold in *Arabidopsis thaliana* leaves and cause water-soaked lesions that appear over the course of two days. Pst MM1065 multiplies a maximum of 10 fold in *Arabidopsis thaliana* leaves and causes the appearance of a mildly chlorotic dry lesion after 48 hours. Thus, disease resistance is associated with severely inhibited growth of the pathogen.

An avirulence gene (avr) of the Pst MM1065 strain was cloned using standard techniques as described in Dong et al. (1991), Plant Cell 3:61–72; Whalen et al., (1991) supra; and Innes et al., (1993), supra. The isolated avirulence gene from this strain was designated avrRpt2. Normally, the virulent strain Psm ES4326 or Pst DC3000 causes the appearance of disease symptoms after 48 hours as described above. In contrast, Psm ES4326/avrRpt2 or Pst DC3000/avrRpt2 elicits the appearance of a visible necrotic hypersensitivity response (HR) within 16 hours and multiplies 50 fold less than Psm ES4326 or Pst DC3000 in wild type *Arabidopsis thaliana* leaves (Dong et al., (1991), supra; and Whalen et al., (1991), supra). Thus, disease resistance in a wild type *Arabidopsis* plant requires, in part, an avirulence gene in the pathogen or a signal generated by the avirulence gene.

The isolation of four *Arabidopsis thaliana* disease resistance mutants has been described using the cloned avrRpt2 gene to search for the host gene required for disease resistance to pathogens carrying the avrRpt2 gene (Yu et al., (1993), supra; Kunkel et al., (1993), supra). The four *Ara-* bidopsis thaliana mutants failed to develop an HR when infiltrated with Psm ES4326/avrRpt2 or Pst DC3000/avrRpt2 as expected for plants having lost their disease resistance capacity. In the case of one of these mutants, approximately 3000 five to six week old $M_2$ ecotype Columbia (Col-0 plants) plants generated by ethyl methanesulfonic acid (EMS) mutagenesis were hand-inoculated with Psm ES4326/avrRpt2 and a single mutant, rps2-101C, was identified (resistance to *Pseudomonas syringae*) (Yu et al., (1993), supra).

The second mutant was isolated using a procedure that specifically enriches for mutants unable to mount an HR (Yu et al., (1993), supra). When 10-day old *Arabidopsis thaliana* seedlings growing on petri plates are infiltrated with *Pseudomonas syringae* pv. *phaseolicola* (Psp) NPS3121 versus Psp NPS3121/avrRpt2, about 90% of the plants infiltrated with Psp NPS3121 survive, whereas about 90%–95% of the plants infiltrated with Psp NPS3121/avrRpt2 die. Apparently, vacuum infiltration of an entire small *Arabidopsis thaliana* seedling with Psp NPS3121/avrRpt2elicits a systemic HR which usually kills the seedling. In contrast, seedlings infiltrated with Psp NPS3121 survive because Psp NPS3121 is a weak pathogen on *Arabidopsis thaliana*. The second disease resistance mutant was isolated by infiltrating 4000 EMS-mutagenized Columbia $M_2$ seedlings with Psp NPS3121/avrRpt2. Two hundred survivors were obtained. These were transplanted to soil and re-screened by hand inoculation when the plants reached maturity. Of these 200 survivors, one plant failed to give an HR when hand-infiltrated with Psm ES4326/avrRpt2. This mutant was designated rps2-102C (Yu et al., (1993), supra).

A third mutant, rps2-201C, was isolated in a screen of approximately 7500 $M_2$ plants derived from seed of *Arabidopsis thaliana* ecotype Col-O that had been mutagenized with diepoxybutane (Kunkel et al., (1993), supra). Plants were inoculated by dipping entire leaf rosettes into a solution containing Pst DC3000/avrRpt2 bacteria and the surfactant Silwet L-77 (Whalen et al., (1991), supra), incubating plants in a controlled environment growth chamber for three to four days, and then visually observing disease symptom development. This screen revealed four mutant lines (carrying the rps2-201C, rps2-202C, rps2-203C, and rps2-204C alleles), and plants homozygous for rps2-201C were a primary subject for further study (Kunkel et al., (1993), supra and the instant application).

Isolation of the fourth rps2 mutant, rps2-101N, has not yet been published. This fourth isolate is either a mutant or a susceptible *Arabidopsis* ecotype. Seeds of the *Arabidopsis* Nossen ecotype were gamma-irradiated and then sown densely in flats and allowed to germinate and grow through a nylon mesh. When the plants were five to six weeks old, the flats were inverted, the plants were partially submerged in a tray containing a culture of Psm ES4326/avrRpt2, and the plants were vacuum infiltrated in a vacuum desiccator. Plants inoculated this way develop an HR within 24 hours. Using this procedure, approximately 40,000 plants were screened and one susceptible plant was identified. Subsequent RFLP analysis of this plant suggested that it may not be a Nossen mutant but rather a different *Arabidopsis* ecotype that is susceptible to Psm ES4326/avrRpt2. This plant is referred to as rps2-101N. The isolated mutants rps2-101C, rps2-102C, rps2-201C, and rps2-101N are referred to collectively as the "rps2 mutants".

The rps2 Mutants Fail to Specifically Respond to the Cloned Avirulence Gene, avrRpt2

The RPS2 gene product is specifically required for resistance to pathogens carrying the avirulence gene, avrRpt2. A mutation in Rps2 polypeptide that eliminates or reduces its function would be observable as the absence of a hypersensitive response upon infiltration of the pathogen. The rps2 mutants displayed disease symptoms or a null response when infiltrated with Psm ES4326/avrRpt2, Pst DC3000/avrRpt2 or Psp NPS3121/avrRpt2, respectively. Specifically, no HR response was elicited, indicating that the plants were susceptible and had lost resistance to the pathogen despite the presence of the avrRpt2 gene in the pathogen.

Pathogen growth in rps2 mutant plant leaves was similar in the presence and absence of the avrRpt2 gene. Psm ES4326 and Psm ES4326/avrRpt2 growth in rps2 mutants was compared and found to multiply equally well in the rps2 mutants, at the same rate that Psm Es4326 multiplied in wild-type *Arabidopsis* leaves. Similar results were observed for Pst DC3000 and Pst DC3000/avrRpt2 growth in rps2 mutants.

The rps2 mutants displayed a HR when infiltrated with *Pseudomonas* pathogens carrying other avr genes, Psm ES4326/avrB, Pst DC3000/avrB, Psm ES4326/avrRpm1, Pst DC3000/avrRpm1. The ability to mount an HR to an avr gene other than avrRpt2 indicates that the rps2 mutants isolated by selection with avrRpt2 are specific to avrRpt2.

Mapping and Cloning of the RPS2 Gene

Genetic analysis of rps2 mutants rps2-101C, rps2-102C, rps-201C and rps-101N showed that they all corresponded to genes that segregated as expected for a single Mendelian locus and that all four were most likely allelic. The four rps2 mutants were mapped to the bottom of chromosome IV using standard RFLP mapping procedures including polymerase chain reaction (PCR)-based markers (Yu et al., (1993), supra; Kunkel et al., (1993), supra; and Mindrinos, M., unpublished). Segregation analysis showed that rps2-101C and rps2-102C are tightly linked to the PCR marker, PG11, while the RFLP marker M600 was used to define the chromosome location of the rps2-201C mutation (FIG. 1A) (Yu et al., (1993), supra; Kunkel et al., (1993), supra). RPS2 has subsequently been mapped to the centromeric side of PG11.

Heterozygous RPS2/rps2 plants display a defense response that is intermediate between those displayed by the wild-type and homozygous rps2/rps2 mutant plants (Yu, et al., (1993), supra; and Kunkel et al., (1993), supra). The heterozygous plants mounted an HR in response to Psm ES4326/avrRpt2 or Pst DC3000/avrRpt2 infiltration; however, the HR appeared later than in wild type plants and required a higher minimum inoculum (Yu, et al., (1993), supra; and Kunkel et al., (1993), supra).

High Resolution Mapping of the RPS2 Gene and RPS2 cDNA Isolation

To carry out map-based cloning of the RPS2 gene, rps2-101N/rps2-101N was crossed with Landsberg erecta RPS2/RPS2. Plants of the $F_1$ generation were allowed to self pollinate (to "self") and 165 $F_2$ plants were selfed to generate $F_3$ families. Standard RFLP mapping procedures showed that rps2-101N maps close to and on the centromeric side of the RFLP marker, PG11. To obtain a more detailed map position, rps2-101N/rps-101N was crossed with a doubly marked Landsberg erecta strain containing the recessive mutations, cer2 and ap2. The genetic distance between cer2 and ap2 is approximately 15 cM, and the rps2 locus is located within this interval. $F_2$ plants that displayed either a CER2 ap2 or a cer2 AP2 genotype were collected, selfed, and scored for RPS2 by inoculating at least 20 $F_3$ plants for each $F_2$ with Psm ES4326/avrRpt2. DNA was also prepared from a pool of approximately 20 $F_3$ plants for each $F_2$ line. The CER2 ap2 and cer2 AP2 recombinants were used to carry out a chromosome walk that is illustrated in FIG. 1.

As shown in FIG. 1, RPS2 was mapped to a 28–35 kb region spanned by cosmid clones E4-4 and E4-6. This region contains at least six genes that produce detectable transcripts. There were no significant differences in the sizes of the transcripts or their level of expression in the rps2 mutants as determined by RNA blot analysis. cDNA clones of each of these transcripts were isolated and five of these were sequenced. As is described below, one of these transcripts, cDNA-4, was shown to correspond to the RPS2 locus. From this study, three independent cDNA clones (cDNA-4-4, cDNA-4-5, and cDNA-4-11) were obtained corresponding to RPS2 from Columbia ecotype wild type plants. The apparent sizes of RPS2 transcripts were 3.8 and 3.1 kb as determined by RNA blot analysis.

A fourth independent cDNA-4 clone (cDNA-4-2453) was obtained using map-based isolation of RPS2 in a separate study. Yeast artificial chromosome (YAC) clones were identified that carry contiguous, overlapping inserts of *Arabidopsis thaliana* ecotype Col-O genomic DNA from the M600 region spanning approximately 900 kb in the RPS2 region. *Arabidopsis* YAC libraries were obtained from J. Ecker and E. Ward, supra and from E. Grill (Grill and Somerville (1991) Mol. Gen. Genet. 226:484–490). Cosmids designated "H" and "E" were derived from the YAC inserts and were used in the isolation of RPS2 (FIG. 1).

The genetic and physical location of RPS2 was more precisely defined using physically mapped RFLP, RAPD (random amplified polymorphic DNA) and CAPS (cleaved amplified polymorphic sequence) markers. Segregating populations from crosses between plants of genotype RPS2/RPS2 (No-O wild type) and rps2-201/rps2-201 (Col-O background) were used for genetic mapping. The RPS2 locus was mapped using markers 17B7LE, PG11, M600 and other markers. For high-resolution genetic mapping, a set of tightly linked RFLP markers was generated using insert end fragments from YAC and cosmid clones (FIG. 1) (Kunkel et al. (1993), supra; Konieczny and Ausubel (1993) Plant J. 4:403–410; and Chang et al. (1988) PNAS USA 85:6856–6860). Cosmid clones E4-4 and E4-6 were then used to identify expressed transcripts (designated cDNA-4, -5, -6, -7, -8 of FIG. 1F) from this region, including the cDNA-4-2453 clone.

RPS2 DNA Sequence Analysis

DNA sequence analysis of cDNA-4 from wild-type Col-O plants and from mutants rps2-101C, rps2-102C, rps2-201C and rps2-101N showed that cDNA-4 corresponds to RPS2. DNA sequence analysis of rps2-102C, rps2-102C and rps2-201C revealed changes from the wild-type sequence as shown in Table 1. The numbering system in Table 1 starts at the ATG start codon encoding the first methionine where A is nucleotide 1. DNA sequence analysis of cDNA-4 corresponding to mutant rps2-102C showed that it differed from the wild type sequence at amino acid residue 476. Moreover, DNA sequence analysis of the cDNA corresponding to cDNA-4 from rps2-101N showed that it contained a 10 bp insertion at amino acid residue 581, a site within the leucine-rich repeat region which causes a shift in the RPS2 reading frame. Mutant rps2-101C contains a mutation that leads to the formation of a chain termination codon. The DNA sequence of mutant allele rps2-201C revealed a mutation altering a single amino acid within a segment of the LRR region that also has similarity to the helix-loop-helix motif, further supporting the designation of this locus as the RPS2 gene. The DNA and amino acid sequences are shown in FIG. 2.

TABLE 1

| Mutant | Wild type | position of Mutation* | Change |
|---|---|---|---|
| rps2-101C | 703 TGA 705 | 704 | TAA Stop Codon |
| rps2-101N | 1741 GTG 1743 | 1741 | GTGGAGTTGTATG Insertion (SEQ ID NO: 216) |
| rps2-102C | 1426 AGA 1428 arg | 1427 | AAA Amino acid 476 lys |
| rps2-201C | 2002 ACC 2004 thr | 2002 | CCC Amino acid pro |

*Nucleotide positions refer to SEQ ID NO:215

DNA sequence analysis of cDNA-4 corresponding to RPS2 from wild-type Col-O plants revealed an open reading frame (between two stop codons) spanning 2,751 bp. There are 2,727 bp between the first methionine codon of this reading frame and the 3'-stop codon, which corresponds to a deduced 909 amino acid polypeptide (See open reading frame "a" of FIG. 2). The amino acid sequence has a relative molecular weight of 104,460 and a pI of 6.51.

As discussed below, RPS2 belongs to a new class of disease resistance genes; the structure of the Rps2 polypeptide does not resemble the protein structure of the product of the previously cloned and publicized avirulence gene-specific plant disease resistance gene, Pto, which has a putative protein kinase domain. From the above analysis of the deduced amino acid sequence, RPS2 contains several distinct protein domains conserved in other proteins from both eukaryotes and prokaryotes. These domains include, but are not limited, to Leucine Rich Repeats (LRR) (Kobe and Deisenhofer, (1994) Nature 366:751–756); nucleotide binding site, e.g. the kinase 1a motif (P-loop) (Saraste et al. (1990) Trends in Biological Sciences TIBS 15:430–434; Helix-Loop-Helix (Murre et al. (1989) Cell 56:777–783; and Leucine Zipper (Rodrigues and Park (1993) Mol. Cell Biol. 13:6711–6722). The amino acid sequence of Rps2 contains a LRR motif (LRR motif from amino acid residue 505 to amino acid residue 867), which is present in many known proteins and which is thought to be involved in protein-protein interactions and may thus allow interaction with other proteins that are involved in plant disease resistance. The N-terminal portion of the Rps2 polypeptide LRR is, for example, related to the LRR of yeast (*Saccharomyces cerevisiae*) adenylate cyclase, CYR1. A region predicted to be a transmembrane spanning domain (Klein et al. (1985) Biochim., Biophys. Acta 815:468–476) is located from amino acid residue 350 to amino acid residue 365, N-terminal to the LRR. An ATP/GTP binding site motif (P-loop) is predicted to be located between amino acid residue 177 and amino acid residue 194, inclusive. The motifs are discussed in more detail below.

From the above analysis of the deduced amino acid sequence, the Rps2 polypeptide may have a membrane-receptor structure which consists of an N-terminal extracellular region and a C-terminal cytoplasmic region. Alternatively, the topology of the Rps2 may be the opposite: an N-terminal cytoplasmic region and a C-terminal extracellular region. LRR motifs are extracellular in many cases and the Rps2 LRR contains five potential N-glycosylation sites.

Identification of RPS2 by Functional Complementation

Complementation of rps2-201 homozygotes with genomic DNA corresponding to *Arabidopsis thaliana* functionally confirmed that the genomic region encoding cDNA-4 carries RPS2 activity. Cosmids were constructed that contained overlapping contiguous sequences of wild type *Arabidopsis thaliana* DNA from the RPS2 region contained in YACs EW11D4, EW9C3, and YUP11F1 of FIG. 1 and FIG. 4. The cosmid vectors were constructed from pSLJ4541 (obtained from J. Jones, Sainsbury Institute, Norwich, England) which contains sequences that allow the inserted sequence to be integrated into the plant genome via *Agrobacterium*-mediated transformation (designated "binary cosmid"). "H" and "E" cosmids (FIG. 1) were used to identify clones carrying DNA from the *Arabidopsis thaliana* genomic RPS2 region.

More than forty binary cosmids containing inserted RPS2 region DNA were used to transform rps2-201 homozygous mutants utilizing *Agrobacterium*-mediated transformation (Chang et al. ((1990) p. 28, Abstracts of the Fourth International Conference on *Arabidopsis* Research, Vienna, Austria). Transformants which remained susceptible (determined by methods including the observed absence of an HR following infection to *P. syringae* pv. *phaseolicola* strain 3121 carrying avrRpt2 and Psp 3121 without ayrRpt2) indicated that the inserted DNA did not contain functional RPS2. These cosmids conferred the "Sus." or susceptible phenotype indicated in FIG. 4. Transformants which had acquired avrRpt2-specific disease resistance (determined by methods including the display of a strong hypersensitive response (HR) when inoculated with Psp 3121 with avrRpt2, but not following inoculation with Psp 3121 without avrRpt2) suggested that the inserted DNA contained a functional RPS2 gene capable of conferring the "Res." or resistant phenotype indicated in FIG. 4. Transformants obtained using the pD4 binary cosmid displayed a strong resistance phenotype as described above. The presence of the insert DNA in the transformants was confirmed by classical genetic analysis (the tight genetic linkage of the disease resistance phenotype and the kanamycin resistance phenotype conferred by the cotransformed selectable marker) and Southern analysis. These results indicated that RPS2 is encoded by a segment of the 18 kb *Arabidopsis thaliana* genomic region carried on cosmid pD4 (FIG. 4).

To further localize the RPS2 locus and confirm its ability to confer a resistance phenotype on the rps2-201 homozygous mutants, a set of six binary cosmids containing partially overlapping genomic DNA inserts were tested. The overlapping inserts pD2, pD4, pD14, pD15, pD27, and pD47 were chosen based on the location of the transcription corresponding to the five cDNA clones in the RPS2 region (FIG. 4). These transformation experiments utilized a vacuum infiltration procedure (Bechtold et al. (1993) C. R. Acad. Sci. Paris 316:1194–1199) for *Agrobacterium*-mediated transformation. *Agrobacterium*-mediated transformations with cosmids pD2, pD14, pD15, pD39, and pD46 were performed using a root transformation/regeneration protocol (Valveekens et al. (1988), PNAS 85:5536–5540). The results of pathogen inoculation experiments assaying for RPS2 activity in these transformants is indicated in FIG. 4.

These experiments were further confirmed using a modification of the vacuum filtration procedure. In particular, the procedure of Bechtold et al. (supra) was modified such that plants were grown in peat-based potting soil covered with a screen, primary inflorescences were removed, and plants with secondary inflorescences (approximately 3 to 15 cm in length) were inverted directly into infiltration medium, infiltrated, and then grown to seed harvest without removal from soil (detailed protocol available on the AAtDB computer database (43). The presence of introduced sequences in the initial pD4 transformant was verified by DNA blot analysis with a pD4 vector and insert sequences (separately) as probes. The presence of the expected sequences in transformants obtained with the vacuum infiltration protocol was also confirmed by DNA blot analysis. Root transformation experiments (19) were performed with an easily regenerable rps2-201/rps2-201×No-0 mapping population. Transformants were obtained for pD4 with in plant transformation, for pD2, 14, 16, 39, and 49 with root transformation, and for pD2, 4, 14, 15, 27, and 47 with vacuum infiltration as modified.

Additional transformation experiments utilized binary cosmids carrying the complete coding region and more than 1 kb of upstream genomic sequence for only cDNA-4 or cDNA-6. Using the vacuum infiltration transformation method, three independent transformants were obtained that carried the wild-type cDNA-6 genomic region in a rps2-201c homozygous background (pAD431 of FIG. 4). None of these plants displayed avrRpt2-dependent disease resistance. Homozygous rps2-201c mutants were transformed with wild-type genomic cDNA-4 (p4104 and p4115, each carrying Col-O genomic sequences corresponding to all of the cDNA-4 open reading frame, plus approximately 1.7 kb of 5' upstream sequence and approximately 0.3 kb of 3' sequence downstream of the stop codon). These p4104 and p4115 transformants displayed a disease resistance phenotype similar to the wild-type RPS2 homozygotes from which the rps2 were derived. Additional mutants (rps2-101N and rps2-101C homozygotes) also displayed avrRpt2-dependent resistance when transformed with the cDNA-4 genomic region.

RPS2 Sequences Allow Detection of other Resistance Genes

DNA blot analysis of *Arabidopsis thaliana* genomic DNA using RPS2 cDNA as the probe showed that *Arabidopsis* contains several DNA sequences that hybridize to RPS2 or a portion thereof, suggesting that there are several related genes in the *Arabidopsis* genome.

From the aforementioned description and the nucleic acid sequence shown in FIG. 2, it is possible to isolate other plant disease resistance genes having about 50% or greater sequence identity to the RPS2 gene. Detection and isolation can be carried out with an oligonucleotide probe containing the RPS2 gene or a portion thereof greater than 9 nucleic acids in length, and preferably greater than about 18 nucleic acids in length. Probes to sequences encoding specific structural features of the Rps2 polypeptide are preferred as they provide a means of isolating disease resistance genes having similar structural domains. Hybridization can be done using standard techniques such as are described in Ausubel et al., *Current Protocols in Molecular Biology*, John Wiley & Sons, (1989).

For example, high stringency conditions for detecting the RPS2 gene include hybridization at about 42° C., and about 50% formamide; a first wash at about 65° C., about 2×SSC, and 1% SDS; followed by a second wash at about 65° C. and about 0.1%×SSC. Lower stringency conditions for detecting RPS genes having about 50% sequence identity to the RPS2 gene are detected by, for example, hybridization at about 42° C. in the absence of formamide; a first wash at about 42° C., about 6×SSC, and about 1% SDS; and a second wash at about 50° C., about 6×SSC, and about 1% SDS. An approximately 350 nucleotide DNA probe encoding the middle portion of the LRR region of Rps2 was used as a probe in the above example. Under lower stringency conditions, a minimum of 5 DNA bands were detected in BamHI digested *Arabidopsis thaliana* genomic DNA as sequences having sufficient sequence identity to hybridize to DNA encoding the middle portion of the LRR motif of Rps2. Similar results were obtained using a probe containing a 300 nucleotide portion of the RPS2 gene encoding the extreme N-terminus of Rps2 outside of the LRR motif.

Isolation of other disease resistance genes is performed by PCR amplification techniques well known to those skilled in the art of molecular biology using oligonucleotide primers designed to amplify only sequences flanked by the oligonucleotides in genes having sequence identity to RPS2. The primers are optionally designed to allow cloning of the amplified product into a suitable vector.

The RPS Disease-Resistance Gene Family

As discussed above, we have discovered that the *Arabidopsis* RPS2 gene described herein is representative of a new class of plant resistance genes. Analysis of the derived amino acid sequence for RPS2 revealed several regions of similarity with known polypeptide motifs (see, e.g., Schneider et al., Genes Dev. 6:797 (1991)). Most prominent among these is a region of multiple, leucine-rich repeats (LRRs). The LRR motif has been implicated in protein-protein interactions and ligand binding in a diverse array of proteins (see, e.g., Kornfield et al., Annu. Rev. Biochem. 64:631 (1985); Alber, Curr. Opin. Gen. Dev. 2:205 (1992); Lupas et al., Science 252:1162 (1991); Saraste et al., Trend Biochem. Sci. 15:430 (1990)). In one example, LRRs form the hormone binding sites of mammalian gonadotropin hormone receptors (see, e.g, Lupas et al., Science 252:1162 (1991)) and, in another example, a domain of yeast adenylate cyclase that interacts with the RAS2 protein (Kornfield et al., Annu. Rev. Biochem. 64:631 (1985)). In RPS2, the LRR domain spans amino acids 503–867 and contains fourteen repeat units of length 22–26 amino acids. A portion of each repeat resembles the LRR consensus sequence (I/L/V)XXLXXLXX(I/L)XL (SEQ ID NO:211). In FIG. 7, the LRRs from RPS2 are shown, as well as an RPS2 consensus sequence. Within the RPS2 LRR region, five (of six) sequences matching the N-glycosylation consensus sequence [NX(S/T)] were observed (FIG. 8, marked with a dot). In particular, N-glycosylation is predicted to occur at amino acids 158, 543, 666, 757, 778, 787. Interestingly, the single nucleotide difference between functional RPS2 and mutant allele rps2-201 is within the LRR coding region, and this mutation disrupts one of the potential glycosylation sites.

Also observed in the deduced amino acid sequence for RPS2 is a second potential protein-protein interaction domain, a leucine zipper (see, e.g., von Heijne, J. Mol. Biol. 225:487 (1992)), at amino acids 30–57. This region contains four contiguous heptad repeats that match the leucine zipper consensus sequence (I/R)XDLXXX (SEQ ID NO:212). Leucine zippers facilitate the dimenzation of transcription factors by formation of coiled-coil structures, but no sequences suggestive of an adjacent DNA binding domain (such as a strongly basic region or a potential zinc-finger) were detected in RPS2. Coiled-coil regions also promote specific interactions between proteins that are not transcription factors (see, e.g., Ward et al., Plant Mol. Biol. 14:561 (1990); Ecker, Methods 1:186 (1990); Grill et al., Mol. Gen. Genet. 226:484 (1991)), and computer database similarity searches with the region spanning amino acids 30–57 of RPS2 revealed highest similarity to the coiled-coil regions of numerous myosin and paramyosin proteins.

A third RPS2 motif was found at the sequence GPG-GVGKT (SEQ ID NO:213) at deduced amino acids 182–189. This portion of RPS2 precisely matches the generalized consensus for the phosphate-binding loop (P-loop) of numerous ATP- and GTP-binding proteins (see, e.g., Saraste et al., supra)). The postulated RPS2 P-loop is similar to those found in RAS proteins and ATP synthase -subunits (Saraste et al., supra), but surprisingly is most similar to the published P-loop sequences for the nifH and chvD genes, respectively. The presence of this P-loop sequence strongly suggests nucleotide triphosphate binding as one aspect of RPS2 function. This domain is also referred to as a kinase-1a motif (or a nucleotide binding site, or NBS). Other conserved NBSs are present in the RPS2 sequence; these NBSs include a kinase-2 motif at amino acids 258–262 and a kinase-3a motif at amino acids 330–335.

Finally, inspection of the RPS2 sequence reveals a fourth RPS2 motif, a potential membrane-spanning domain located at amino acids 340–360. Within this region, a conserved GLPLAL (SEQ ID NO:217) motif is found at amino acids 347–352. The presence of the membrane-spanning domain raises the possibility that the RPS2 protein is membrane localized, with the N-terminal leucine zipper and P-loop domains residing together on the opposite side of the membrane from the LRR region. An orientation in which the C-terminal LRR domain is extracellular is suggested by the fact that five of the six potential N-linked glycosylation sites occur C-terminal to the proposed membrane-spanning domain, as well as by the overall more positive charge of the N-terminal amino acid residues (see, e.g., Kornfield et al., supra; von Heijne, supra). A number of proteins that contain LRRs are postulated or known to be membrane-spanning receptors in which the LRRs are displayed extracellularly as a ligand-binding domain (see, e.g., Lopez et al., Proc. Natl. Acad. Sci. 84:5615 (1987); Braun et al., EMBO J. 10:1885 (1991); Schneider et al., supra).

The plant kingdom contains hundreds of resistance genes that are necessarily divergent since they control different resistance specificities. However, plant defense responses such as production of activated oxygen species, PR-protein gene expression, and the hypersensitive response are common to diverse plant-pathogen interactions. This implies that there are points of convergence in the defense signal transduction pathways downstream of initial pathogen recognition, and also suggests that similar functional motifs may exist among diverse resistance gene products. Indeed, RPS2 is dissimilar from previously described disease resistance genes such as Hm1 or Pto (see, e.g., Johal et al., supra; Martin et al., supra), and thus represents a new class of genes having disease resistance capabilities.

Isolation of other Members of the RPS Disease-Resistance Gene Family Using Conserved Motif Probes and Primers We have discovered that the RPS2 motifs described above are conserved in other disease-resistance genes, including, without limitation, the N protein, the L6 protein, and the Prf protein. As shown in FIGS. 5(A and B), we have determined that the L6 polypeptide of flax, the N polypeptide of tobacco, and the Prf polypeptide of tomato each share unique regions of similarity (including, but not limited to, the leucine-rich repeats, the membrane-spanning domain, the leucine zipper, and the P-loop and other NBS domains).

On the basis of this discovery, the isolation of virtually any member of the RPS gene family is made possible using standard techniques. In particular, using all or a portion of the amino acid sequence of a conserved RPS motif (for example, the amino acid sequences defining any RPS P-loop, NBS, leucine-rich repeat, leucine zipper, or membrane-spanning region), one may readily design RPS oligonucleotide probes, including RPS degenerate oligonucleotide probes (i.e., a mixture of all possible coding sequences for a given amino acid sequence). These oligonucleotides may be based upon the sequence of either strand of the DNA comprising the motif. General methods for designing and preparing such probes are provided, for example, in Ausubel et al., supra and *Guide to Molecular Cloning Techniques*, 1987, S. L. Berger and A. R. Kimmel, eds., Academic Press, New York. These oligonucleotides are useful for RPS gene isolation, either through their use as probes capable of hybridizing to RPS complementary sequences or as primers for various polymerase chain reaction (PCR) cloning strategies.

Hybridization techniques and procedures are well known to those skilled in the art and are described, for example, in Ausubel et al., supra and *Guide to Molecular Cloning Techniques*, 1987, S. L. Berger and A. R. Kimmel, eds., Academic Press, New York. If desired, a combination of different oligonucleotide probes may be used for the screening of the recombinant DNA library. The oligonucleotides are labelled with $^{32}$P using methods known in the art, and the detectably-labelled oligonucleotides are used to probe filter replicas from a recombinant plant DNA library. Recombinant DNA libraries may be prepared according to methods well known in the art, for example, as described in Ausubel et al., supra. Positive clones may, if desired, be rescreened with additional oligonucleotide probes based upon other RPS conserved regions. For example, an RPS clone identified based on hybridization with a P-loop-derived probe may be confirmed by re-screening with a leucine-rich repeat-derived oligonucleotide.

As discussed above, RPS oligonucleotides may also be used as primers in PCR cloning strategies. Such PCR methods are well known in the art and described, for example, in PCR Technology, H. A. Erlich, ed., Stockton Press, London, 1989; PCR Protocols: A Guide to Methods and Applications, M. A. Innis, D. H. Gelfand, J. J. Sninsky, and T. J. White, eds., Academic Press, Inc., New York, 1990; and Ausubel et al., supra. If desired, members of the RPS disease-resistance gene family may be isolated using the PCR "RACE" technique, or Rapid Amplification of cDNA Ends (see, e.g., Innis et al., supra). By this method, oligonucleotide primers based on an RPS conserved domain are oriented in the 3' and 5' directions and are used to generate overlapping PCR fragments. These overlapping 3'- and 5'-end RACE products are combined to produce an intact full-length cDNA. This method is described in Innis et al., supra; and Frohman et al., Proc. Natl. Acad. Sci. 85:8998, 1988.

Any number of probes and primers according to the invention may be designed based on the conserved RPS motifs described herein. Preferred motifs are boxed in the sequences shown in FIG. 5(A or B). In particular, oligonucleotides according to the invention may be based on the conserved P-loop domain, the amino acids of which are shown below:

```
MOTIF 1

L6       G MGGIGKTTTA      (SEQ ID NO:110)

N        G MGGVGKTTIA      (SEQ ID NO:111)

PrfP     G MPGLGKTTLA      (SEQ ID NO:112)

RPS2     G PGGVGKTTLM      (SEQ ID NO:113)
```

From these sequences, appropriate oligonucleotides are designed and prepared using standard methods. Particular examples of RPS oligonucleotides based on the P-loop domain are as follows (N is A, C, T, or G).

Based on Motif 1:

```
5'GGNATGGGNGGNNTNGGNAA(A or G)ACNAC 3'                                      (SEQ ID NO:158)

5'NCGNG(A/T)NGTNA(T/G)(G/A/T)A(T/A)NCGNA 3'                                 (SEQ ID NO:159)

5'GG(T or A)NT(T or G or C)GG(T or A)AA(G or A)AC(T or C or A)AC 3'         (SEQ ID NO:160)

5'GGNATGGGNGGNNTNGGNAA(A or G)ACNAC 3'                                      (SEQ ID NO:158)

5'N(G or A)(C or T)N(A or G)(A or G or T)NGTNGT(C or T)                     (SEQ ID NO:161)
  TTNCCNANNCCN(G or C)(G or C)N(G or A)(T or G)NCC 3'

5'GGN(C or A)(T or C)N(G or C)NGGNNTNGGNAA(A or G)ACNAC 3'                  (SEQ ID NO:162)
```

Other conserved RPS motifs useful for oligonucleotide design are shown below. These motifs are also depicted in the sequence of FIG. 5(A or B).

```
MOTIF 2

L6        FKILVV LDDVD(SEQ ID NO:114)

N         KKVLIV LDDID(SEQ ID NO:115)

PrfP      KRFLIL IDDVW(SEQ ID NO:116)

RPS2      KRFLLL LDDVW(SEQ ID NO:117)

MOTIF 3

L6        SRFIIT SR(SEQ ID NO:118)

N         SRIIIT TR(SEQ ID NO:119)

PrfP      SRIILT TR(SEQ ID NO:120)

RPS2      CKVMFT TR(SEQ ID NO:121)

MOTIF 4

L6        GLPLTLK V(SEQ ID NO:122)

N         GLPLALK V(SEQ ID NO:123)

PrfP      GLPLSVV L(SEQ ID NO:124)

RPS2      GLPLALI T(SEQ ID NO:125)
```

-continued

```
MOTIF 5

L6      KISYDAL(SEQ ID NO:126)

N       KISYDGL(SEQ ID NO:127)

PrfP    GFSYKNL(SEQ ID NO:128)

RPS2    KFSYDNL(SEQ ID NO:208)
```

From the above motifs and the sequence motifs designated in FIGS. 5A and B, appropriate oligonucleotides are designed and prepared. Particular examples of such RPS oligonucleotides are as follows (N is A, T, C, or G).

Based on Motif 2:

(SEQ ID NO: 214)
5'T(T or C)GA(T or C)GA(T or C)(A or G)T(T or G or C)(T or G)(A or G)(T or G or C)(G or A)A 3'

(SEQ ID NO: 164)
5'T(T or C)CCA(G or C or A)A(T or C)(G or A)TC(A or G)TCNA 3'

(SEQ ID NO: 165)
5'(C or G or A)(T or C)(C or A)NA(T or C)(G or A)TC(G or A)TCNA(G or A or T)NA(G or A or C)NANNA(G or A)NA 3'

(SEQ ID NO: 166)
5'(T or A)(T or A)N(A or C)(A or G)(A or G)(T or G or A)TN(T or C)TNNTN(G or T or C)TN(A or T or C)TNGA(T or C)GA 3'

Based on Motif 3:

(SEQ ID NO: 167)
5'NCGNG(A or T)NGTNA(T or G)(G or A or T)A(T or A)NCGNGA 3'

(SEQ ID NO: 167)
5'NCGNG(A or T)NGTNA(T or G)(G or A or T)A(T or A)NCGNGA 3'

(SEQ ID NO: 168)
5'NC(G or T)N(G or C)(A or T)NGTNA(A or G or T)(A or G or T)AT(A or G or T)AATNG 3'

Based on Motif 4:

(SEQ ID NO: 169)
5'NA(G or A)NGGNA(G or A)NCC 3'

(SEQ ID NO: 170)
5'GG(T or A)(T or C)T(T or G or C)CC(T or A)(T or C)T(T or G or C)GC(T or C or A)(T or C)T 3'

(SEQ ID NO: 171)
5'A(A or G)(T or G or A)GC(G or C or A)A(G or A)(T or A)GG(G or C or A)A(G or A)(A or G or T or C)CC 3'

(SEQ ID NO: 169)
5'NA(G or A)NGGNA(G or A)NCC 3'

(SEQ ID NO: 172)
5'N(A or G)NN(T or A)(T or C)NA(G or C or A)N(C or G)(A or T or C)NA(G or A)NGGNA(G or A)NCC 3'

(SEQ ID NO: 173)
5'GGN(T or C)TNCCN(T or C)TN(G or A or T)(C or G)N(T or G or C)T 3'

Based on Motif 5:

(SEQ ID NO: 174)
5'A(A or G)(A or G)TT(A or G)TC(A or G)TA(G or A or T)(G or C)(T or A)(G or A)A(T or A)(C or T)TT 3'

(SEQ ID NO: 175)
5'A(G or A)N(T or C)(T or C)NT(C or T)(A or G)TAN(G or C)(A or G)NANN(C or T)(C or T) 3'

(SEQ ID NO: 176)
5'(G or A)(G or A)N(A or T)T(A or C or T)(T or A)(G or C)NTA(T or C)(G or A)AN(A or G)(A or C or G)N(T or C)T 3'

Based on Motif 6:

(SEQ ID NO: 177)
5'GTNTT(T or C)(T or C)TN(T or A)(G or C)NTT(T or C)(A or C)G(A or G)GG 3'

Based on Motif 7:

(SEQ ID NO: 178)
5'CCNAT(A or C or T)TT(T or C)TA(T or C)(G or A)(T or A)(G or T or C)GTNGA(T or C)CC 3'

Based on Motif 8:

(SEQ ID NO: 179)
5'GTNGGNAT(A or C or T)GA(T or C)(G or A)(A or C)NCA 3'

Based on Motif 9:

(SEQ ID NO: 180)
5'(G or A)AA(G or A)CANGC(A or G or T)AT(G or A)TCNA(G or A)(G or A)AA 3'

(SEQ ID NO: 181)
5'TT(T or C)(T or C)TNGA(T or C)AT(A or C or T)GCNTG(T or C)TT 3'

Based on Motif 10:

(SEQ ID NO: 182)
5'CCCAT(G or A)TC(T or C)(T or C)(T or G)NA(T or G or A)N(T or A)(G or A)(G or A)TC(A or G)TGCAT 3'

(SEQ ID NO: 183)
5'ATGCA(T or C)GA(T or C)(T or C)(T or A)N(A or C or T)TN(A or C)(A or G)(A or G)GA(T or C)ATGGG 3'

Based on Motif 11:

(SEQ ID NO: 184)
5'NA(G or A)N(G or C)(A or T)(T or C)T(T or C)NA(A or G)(C or T)TT 3'

(SEQ ID NO: 185)
5'(A or T)(G or C)NAA(A or G)(T or C)TN(A or G)A(A or G)(A or T)(G or C)N(T or C)T 3'

Based on Motif 12:

(SEQ ID NO: 186)
5'(A or G or T)(A or T)(A or T)(C or T)TCNA(G or A)N(G or C)(A or T)N(T or C)(G or T)NA(G or A)NCC 3'

-continued (SEQ ID NO: 187)
5'GGN(T or C)TN(A or C)(G or A)N(A or T)(G or L)N
(T or C)TNGA 3'

Once a clone encoding a candidate RPS family gene is identified, it is then determined whether such gene is capable of conferring disease-resistance to a plant host using the methods described herein or other methods well known in the art of molecular plant pathology.

A Biolistic Transient Expression Assay for Identification of Plant Resistance Genes We have developed a functional transient expression system capable of providing a rapid and broadly applicable method for identifying and characterizing virtually any gene for its ability to confer disease-resistance to a plant cell. In brief, the assay system involves delivering by biolistic transformation a candidate plant disease-resistance gene to a plant tissue sample (e.g., a piece of tissue from a leaf) and then evaluating the expression of the gene within the tissue by appraising the presence or absence of a disease-resistance response (e.g., the hypersensitive response). This assay provides a method for identifying disease-resistance genes from a wide variety of plant species, including ones that are not amenable to genetic or transgenic studies.

The principle of the assay is depicted in the top portion of FIG. 9. In general, plant cells carrying a mutation in the resistance gene of interest are utilized. Prior to biolistic transformation, the plant tissue is infiltrated with a phytopathogenic bacterium carrying the corresponding avirulence gene. In addition, a gene to be assayed for its resistance gene activity is co-introduced by biolistics with a reporter gene. The expression of the cobombarded reporter gene serves as an indicator for viability of the transformed cells. Both genes are expressed under the control of a strong and constitutive promoter. If the gene to be assayed does not complement the resistance gene function, the plant cells do not undergo a hypersensitive response (HR) and, therefore, survive (FIG. 9, top panel, right). In this case, cells accumulate a large amount of the reporter gene product. If, on the other hand, a resistance gene is introduced, the plant cells recognize the signal from the avirulence-gene-carrying bacterium and undergo the HR because the expressed resistance gene product complements the function (FIG. 9, top panel, left). In this case, the plant cells do not have enough time to accumulate a large amount of reporter gene product before their death. Given the transformation efficiency estimated by a proper control (such as the uninfected half of the leaf), measuring the accumulation of reporter gene product can thus indicate whether the gene to be assayed complements the resistance gene function.

In one working example, we now demonstrate the effectiveness of the transient expression assay, using the bacterial avirulence gene avrRpt2 and the corresponding *Arabidopsis thaliana* resistance gene RPS2 (FIG. 9, bottom panel). In brief, rps2 mutant leaves, preinfected with *P. syringae* carrying avrRpt2, were co-bombarded with two plasmids, one of which contained the RPS2 gene and the other the *Escherichia coli* uidA gene encoding β-glucuronidase (GUS; Jefferson et al., 1986, supra). Both the RPS2 and uidA genes are located downstream of the strong constitutive 35S promoter from cauliflower mosaic virus (Odell et al., infra). If the 35S-RPS2 construct complements the rps2 mutation, the transformed cells rapidly undergo programmed cell death in response to the *P. syringae* carrying avrRpt2, and relatively little GUS activity accumulates. If the rps2 mutation is not complemented, cell death does not occur and high levels of GUS activity accumulate. These differences in GUS activity are detected histochemically. Because the cDNA library used to identify RPS2 was constructed in the expression vector pKEx4tr, the 35S-RPS2 cDNA construct in pKEx4tr could be used directly in the transient assay. As shown in FIG. 11, pKEx4tr is a cDNA expression vector designed for the unidirectional insertion of cDNA inserts. Inserted cDNA is expressed under the control of the 35S cauliflower mosaic virus promoter.

Our results are shown in FIG. 9, lower panel. In this experiment, we infected one side of a leaf of an rps2 mutant plant with *P. syringae* pv. *phaseoicola* 3121 carrying avrRpt2 (Psp 3121/avrRpt2). Psp 3121 is a weak pathogen of *A. thaliana* and Psp 3121/avrRpt2 can elicit an HR in a plant carrying the resistance gene RPS2 (e.g., a wild type plant). Leaves of 5-week-old *Arabidopsis* plants were infiltrated with an appropriate bacterial suspension at a dose of $2 \times 10^8$/ml by hand infiltration as described (Dong et al., supra). After an incubation period (typically 2–4 hours), the leaves were bombarded using a Bio-Rad PDS-1000/He apparatus (1100 psi) after 2–4 hr of infection. Gold particles were prepared according to the instructions of the manufacturer. For each bombardment, 1.4 μg of pKEx4tr-G, 0.1 μg of a plasmid to be tested, and 0.5 mg of 1 μm gold particles were used. After the bombardment, the leaves were leaf, transformation efficiency (i.e., density of transformed cells) is similar on both sides of the leaf. If transformed cells on the infected side are rapidly killed, staining of the cells on the infected side is weaker than staining on the uninfected side. When the resistance gene RPS2 was co-introduced, the transformed cells on the infected side of the leaf showed much weaker staining than ones on the uninfected side (FIG. 10). In contrast, when an unrelated gene was co-introduced, the transformed cells on the infected side showed similar staining intensity to ones on the uninfected side (FIG. 10).

Thus, as summarized in the Table 2, 35S-RPS4 (cDNA 4), but not cDNA-5 or cDNA-6, complemented the HR phenotype of rps2-101C. (See FIG. 1)

TABLE 2

| Gene Tested | Response (Decreased GUS Activity)[a] |
|---|---|
| ΔGUS (35S-uidA containing internal uidA deletion) | – |
| cDNA-5 (35S-AB11) | |
| cDNA-4 (35S-RPS2) | + |
| cDNA-6 (35S-CK1) | |

[a]When decreased GUS activity was observed on the infiltrated side of the leaf, the response was scored as plus (FIG. 10).

Both RPS2 cDNA-4 clones 4 and 11, corresponding to the two RPS2 different transcript sizes, complemented the rps2 mutant phenotype, indicating that both transcripts encode a functional product. Moreover, 35S-RPS2 also complemented mutants rps2-102C, rps2-101N, and rps2-201C, further confirming that the rps2-101C, rps2-102C, rps2-201C and rps2-101N mutations are all allelic. In short, the cloned RPS2 gene complemented the rps2 mutation in this transient expression assay, and complementation by RPS2 was observed in all four available rps2 mutant stains.

Next we used the transient assay system to test the specificity of the cloned RPS2 gene for an avrRpt2-generated signal (i.e., the "gene-for-gene" specificity of a *P. syringae* avirulence gene and a corresponding *A. thaliana* resistance gene (avrRpm1 and RPM1, respectively)). This experiment involved the use of an rps2-101 rpm1 double mutant that cannot mount an HR when challenged with *P. syringae* carrying avrRpt2 or the unrelated avirulence gene avrRpm1 (Debener et al., Plant Journal 1:289–302, 1991). As summarized in Table 3, complementation of the rps2 mutant phenotype by 35S-RPS2 was only observed in the presence of a signal generated by avrRpt2, indicating that RPS2 does not simply sensitize the plant resistance response in a nonspecific manner.

TABLE 3

| avr Gene | Construct Cobombarded with 35S-uidA | Response[a] |
|---|---|---|
| None (vector only) | ΔGUS[b] | − |
| avrRPt2 | ΔGUS | − |
| avrRpm1 | ΔGUS | − |
| None (vector only) | 35S-RPS2 | − |
| avrRpt2 | 35S-RPS2 | + |
| avrRpm1 | 35S-RPS2 | − |

[a]When decreased GUS activity was observed on the infiltrated side of the leaf, the response was scored as plus. (FIG. 10, panel B)
[b]ΔGUS is 35S-uidA containing an internal deletion in the uidA gene.

Also as shown in Table 3, the RPS2 gene complemented the mutant phenotype when leaves were infected with Psp 3121/avrRpt2 but not with Psp 3121/avrRpm1. Therefore, the RPS2 gene complemented only the rps2 mutation; it did not the rpm1 mutation.

We have also discovered that overexpression of an rps gene family member, e.g., rps2 but not other genes, in the transient assay leads to apparent cell death, obviating the need to know the corresponding avirulence gene for a putative resistance gene that has been cloned.

Using this assay, any plant disease-resistance gene may be identified from a cDNA expression library. In one particular example, a cDNA library is constructed in an expression vector and then introduced as described herein into a plant cultivar or its corresponding mutant plant lacking the resistance gene of interest. Preferably, the cDNA library is divided into small pools, and each pool co-introduced with a reporter gene. If a pool contains a resistance gene clone (i.e., the pool "complements" the resistance gene function), the positive pool is divided into smaller pools and the same procedure is repeated until identification of a single positive clone is ultimately achieved. This approach facilitates the cloning of any resistance gene of interest without genetic crosses or the creation of transgenics.

We now describe the cloning of another member of the RPS gene family, the Prf gene of tomato.

The initial step for the cloning of the Prf gene came from classical genetic analysis which showed that Prf was tightly linked to the tomato Pto gene (Salmeron et al., The Plant Cell 6:511–520, 1994). This prompted construction of a cosmid contig of 200 kb in length which encompassed the Pto locus. DNA probes from this contig were used to screen a tomato cDNA library constructed using tomato leaf tissue that had been infected with Pst expressing the avrPto avirulence gene as source material. Two classes of cDNAs were identified based on cross-hybridization of clones to each other. While one class corresponded to members of the Pto gene family, the other class displayed no hybridization to Pto family members. Taking the assumption (based on the aforementioned genetic analysis) that Prf might reside extremely close to the Pto gene, cDNAs from the second class were analyzed further as candidate Prf clones. These clones were hybridized to filters containing DNAs from six independent prf mutant lines that had been isolated by diepoxybutane or fast neutron treatment. In one of the fast neutron mutants, the cDNA probe revealed a 1.1 kb deletion in the genomic DNA, suggesting that the cDNA clone might in fact represent Prf. Wild-type DNA corresponding to the deletion was cloned from Prf/Prf tomato. A 5 kb region was sequenced and found to potentially encode a protein containing P-loop and leucine-rich repeat motifs, supporting the hypothesis that this DNA encoded Prf. The corresponding DNA was cloned and sequenced from the fast neutron mutant plant. Sequencing this DNA confirmed the mutation to be a simple 1.1 kb deletion excising DNA between the potential P-loop and leucine-rich repeat coding regions. The gene is expressed based on RT-PCR analysis which has shown that an mRNA is transcribed from this region. The identity of the cloned DNA as the Prf gene is based on both the existence of the deletion mutation and the predicted protein sequence, which reveals patches of strong similarity to other cloned disease resistance gene products throughout the amino-terminal half (as described herein). A partial sequence of the Prf gene is shown in FIG. 12.

RPS Expression in Transgenic Plant Cells and Plants

The expression of the RPS2 genes in plants susceptible to pathogens carrying avrRpt2 is achieved by introducing into a plant a DNA sequence containing the RPS2 gene for expression of the Rps2 polypeptide. A number of vectors suitable for stable transfection of plant cells or for the establishment of transgenic plants are available to the public; such vectors are described in, e.g., Pouwels et al., *Cloning Vectors: A Laboratory Manual*, 1985, Supp. 1987); Weissbach and Weissbach, *Methods for Plant Molecular Biology*, Academic Press, 1989; and Gelvin et al., *Plant Molecular Biology Manual*, Kluwer Academic Publishers, 1990. Typically, plant expression vectors include (1) one or more cloned plant genes under the transcriptional control of 5' and 3' regulatory sequences and (2) a dominant selectable marker. Such plant expression vectors may also contain, if desired, a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

An example of a useful plant promoter which could be used to express a plant resistance gene according to the invention is a caulimovirus promoter, e.g., the cauliflower mosaic virus (CaMV) 35S promoter. These promoters confer high levels of expression in most plant tissues, and the activity of these promoters is not dependent on virtually encoded proteins. CaMV is a source for both the 35S and 19S promoters. In most tissues of transgenic plants, the CaMV 35S promoter is a strong promoter (see, e.g., Odel et al., Nature 313:810, (1985)). The CaMV promoter is also highly active in monocots (see, e.g., Dekeyser et al., Plant Cell 2:591, (1990); Terada and Shimamoto, Mol. Gen. Genet. 220:389, (1990)).

Other useful plant promoters include, without limitation, the nonpaline synthase promoter (An et al., Plant Physiol. 88:547, (1988)) and the octopine synthase promoter (Fromm et al., Plant Cell 1:977, (1989)).

For certain applications, it may be desirable to produce the RPS2 gene product or the avrRpt2 gene product in an appropriate tissue, at an appropriate level, or at an appropriate developmental time. Thus, there are a variety of gene promoters, each with its own distinct characteristics embodied in its regulatory sequences, shown to be regulated in response to the environment, hormones, and/or developmental cues. These include gene promoters that are responsible for (1) heat-regulated gene expression (see, e.g., Callis et al., Plant Physiol. 88: 965, (1988)), (2) light-regulated gene expression (e.g., the pea rbcS-3A described by Kuhlemeier et al., Plant Cell 1: 471, (1989); the maize rbcS promoter described by Schaffner and Sheen, Plant Cell 3: 997, (1991); or the chlorophyll a/b-binding protein gene found in pea described by Simpson et al., EMBO J. 4: 2723, (1985)), (3) hormone-regulated gene expression (e.g., the abscisic acid responsive sequences from the Em gene of wheat described Marcotte et. al., Plant Cell 1:969, (1989)), (4) wound-induced gene expression (e.g., of wunI described by Siebertz et al., Plant Cell 1: 961, (1989)), or (5) organ-specific gene expression (e.g., of the tuber-specific storage protein gene described by Roshal et al., EMBO J. 6:1155, (1987); the 23-kDa zein gene from maize described by Schernthaner et al., EMBO J. 7: 1249, (1988); or the French bean β-phaseolin gene described by Bustos et al., Plant Cell 1:839, (1989)).

Plant expression vectors may also optionally include RNA processing signals, e.g, introns, which have been shown to be important for efficient RNA synthesis and accumulation (Callis et al., Genes and Dev. 1: 1183, (1987)). The location of the RNA splice sequences can influence-the level of transgene expression in plants. In view of this fact, an intron may be positioned upstream or downstream of an Rps2 polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., Proc. Natl Acad. Sci USA 84: 744, (1987); An et al., Plant Cell 1: 115, (1989)). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify the cells that have become transformed. Useful selectable marker genes for plant systems include genes encoding antibiotic resistance genes, for example, those encoding resistance to hygromycin, kanamycin, bleomycin, G418, streptomycin or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase, which confers resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 μg/ml (kanamycin), 20–50 μg/ml (hygromycin), or 5–10 μg/ml (bleomycin). A useful strategy for selection of transformants for herbicide resistance is described, e.g., in Vasil I. K., *Cell Culture and Somatic Cell Genetics of Plants*, Vol I, II, III Laboratory Procedures and Their Applications Academic Press, New York, 1984.

It should be readily apparent to one skilled in the field of plant molecular biology that the level of gene expression is dependent not only on the combination of promoters, RNA processing signals and terminator elements, but also on how these elements are used to increase the levels of gene expression.

The above exemplary techniques may be used for the expression of any gene in the RPS family.

Plant Transformation

Upon construction of the plant expression vector, several standard methods are known for introduction of the recombinant genetic material into the host plant for the generation of a transgenic plant. These methods include (1) *Agrobacterium*-mediated transformation (*A. tumefaciens* or *A. rhizogenes*) (see, e.g., Lichtenstein and Fuller In: *Genetic Engineering*, vol 6, P W J Rigby, ed, London, Academic Press, 1987; and Lichtenstein, C. P., and Draper, J,. In: *DNA Cloning*, Vol II, D. M. Glover, ed, Oxford, IRI Press, 1985), (2) the particle delivery system (see, e.g., Gordon-Kamm et al., Plant Cell 2:603, (1990); or BioRad Technical Bulletin 1687, supra), (3) microinjection protocols (see, e.g., Green et al., *Plant Tissue and Cell Culture*, Academic Press, New York, 1987), (4) polyethylene glycol (PEG) procedures (see, e.g., Draper et al., Plant Cell Physiol 23:451, (1982); or e.g., Zhang and Wu, Theor. Appl. Genet. 76:835, (1988)), (5) liposome-mediated DNA uptake (see, e.g., Freeman et al., Plant Cell Physiol 25: 1353, (1984)), (6) electroporation protocols (see, e.g., Gelvin et al supra; Dekeyser et al. supra; or Fromm et al Nature 319: 791, (1986)), and (7) the vortexing method (see, e.g., Kindle, K., Proc. Natl. Acad. Sci., USA 87:1228, (1990)).

The following is an example outlining an *Agrobacterium*-mediated plant transformation. The general process for manipulating genes to be transferred into the genome of plant cells is carried out in two phases. First, all the cloning and DNA modification steps are done in *E. coli*, and the plasmid containing the gene construct of interest is transferred by conjugation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E.coli* prior to transfer to *Agrobacterium* for subsequent introduction into plants. Resistance genes can be carried on the vector, one for selection in bacteria, e.g., streptomycin, and the other that will express in plants, e.g., a gene encoding for kanamycin resistance or an herbicide resistance gene. Also present are restriction endonuclease sites for the addition of one or more transgenes operably linked to appropriate regulatory sequences and directional T-DNA border sequences which, when recognized by the transfer functions of *Agrobacterium*, delimit the region that will be transferred to the plant.

In another example, plant cells may be transformed by shooting into the cell tungsten microprojectiles on which cloned DNA is precipitated. In the Biolistic Apparatus (Bio-Rad, Hercules, Calif.) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

Transfer and expression of transgenes in plant cells is now routine practice to those skilled in the art. It has become a major tool to carry out gene expression studies and to attempt to obtain improved plant varieties of agricultural or commercial interest.

Transgenic Plant Regeneration

Plant cells transformed with a plant expression vector can be regenerated, e.g., from single cells, callus tissue or leaf discs according to standard plant tissue culture techniques. It is well known in the art that various cells, tissues and organs from almost any plant can be successfully cultured to regenerate an entire plant; such techniques are described, e.g., in Vasil supra; Green et al., supra; Weissbach and Weissbach, supra; and Gelvin et al., supra.

In one possible example, a vector carrying a selectable marker gene (e.g., kanamycin resistance), a cloned RPS2 gene under the control of its own promoter and terminator or, if desired, under the control of exogenous regulatory sequences such as the 35S CaMV promoter and the nopaline synthase terminator is transformed into *Agrobacterium*. Transformation of leaf tissue with vector-containing *Agrobacterium* is carried out as described by Horsch et al. (Science 227: 1229, (1985)). Putative transformants are selected after a few weeks (e.g., 3 to 5 weeks) on plant tissue culture media containing kanamycin (e.g. 100 µg/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less media and grown in a greenhouse. Kanamycin-resistant progeny are selected by sowing surfaced sterilized seeds on hormone-free kanamycin-containing media. Analysis for the integration of the transgene is accomplished by standard techniques (see, e.g., Ausubel et al. supra; Gelvin et al. supra).

Transgenic plants expressing the selectable marker are then screened for transmission of the transgene DNA by standard immunoblot and DNA and RNA detection techniques. Each positive transgenic plant and its transgenic progeny are unique in comparison to other transgenic plants established with the same transgene. Integration of the transgene DNA into the plant genomic DNA is in most cases random and the site of integration can profoundly effect the levels, and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using Rps2 polypeptide-specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Once the Rps2 polypeptide has been expressed in any cell or in a transgenic plant (e.g., as described above), it can be isolated using any standard technique, e.g., affinity chromatography. In one example, an anti-Rps2 antibody (e.g., produced as described in Ausubel et al., supra, or by any standard technique) may be attached to a column and used to isolate the polypeptide. Lysis and fractionation of Rps2-producing cells prior to affinity chromatography may be performed by standard methods (see, e.g., Ausubel et al., supra). Once isolated, the recombinant polypeptide can, if desired, be further purified, e.g., by high performance liquid chromatography (see, e.g., Fisher, *Laboratory Techniques In Biochemistry And Molecular Biology*, Work and Burdon, eds., Elsevier, 1980).

These general techniques of polypeptide expression and purification can also be used to produce and isolate useful Rps2 fragments or analogs.

Antibody Production

Using a polypeptide described above (e.g., the recombinant protein or a chemically synthesized RPS peptide based on its deduced amino acid sequence), polyclonal antibodies which bind specifically to an RPS polypeptide may be produced by standard techniques (see, e.g., Ausubel et al., supra) and isolated, e.g., following peptide antigen affinity chromatography. Monoclonal antibodies can also be prepared using standard hybridoma technology (see, e.g., Kohler et al., Nature 256: 495, 1975; Kohler et al., Eur. J. Immunol. 6: 292, 1976; Hammerling et al., in *Monoclonal Antibodies and T Cell Hybridomas*, Elsevier, N.Y., 1981; and Ausubel et al., supra).

Once produced, polyclonal or monoclonal antibodies are tested for specific RSP polypeptide recognition by Western blot or immunoprecipitation analysis (by methods described in Ausubel et al., supra). Antibodies which specifically recognize a RPS polypeptide are considered to be useful in the invention; such antibodies may be used, e.g., for screening recombinant expression libraries as described in Ausubel et al., supra. Exemplary peptides (derived from Rps2) for antibody production include:

```
LKFSYDNLESDLL (SEQ ID NO: 188)

GVYGPGGVGKTTLMQS (SEQ ID NO: 189)

GGLPLALITLGGAM (SEQ ID NO: 190)
```

Use

Introduction of RPS2 into a transformed plant cell provides for resistance to bacterial pathogens carrying the avrRpt2 avirulence gene. For example, transgenic plants of the instant invention expressing RPS2 might be used to alter, simply and inexpensively, the disease resistance of plants normally susceptible to plant pathogens carrying the avirulence gene, avrRpt2.

The invention also provides for broad-spectrum pathogen resistance by mimicking the natural mechanism of host resistance. First, the RPS2 transgene is expressed in plant cells at a sufficiently high level to initiate the plant defense response constitutively in the absence of signals from the pathogen. The level of expression associated with plant defense response initiation is determined by measuring the levels of defense response gene expression as described in Dong et al., supra. Second, the RPS2 transgene is expressed by a controllable promoter such as a tissue-specific promoter, cell-type specific promoter or by a promoter that is induced by an external signal or agent thus limiting the temporal and tissue expression of a defense response. Finally, the RPS2 gene product is co-expressed with the avrRpt2 gene product. The RPS2 gene is expressed by its natural promoter, by a constitutively expressed promoter such as the CaMV 35S promoter, by a tissue-specific or cell-type specific promoter, or by a promoter that is activated by an external signal or agent. Co-expression of RPS2 and avrRpt2 will mimic the production of gene products associated with the initiation of the plant defense response and provide resistance to pathogens in the absence of specific resistance gene-avirulence gene corresponding pairs in the host plant and pathogen.

The invention also provides for expression in plant cells of a nucleic acid having the sequence of FIG. 2 or the expression, of a degenerate variant thereof encoding the amino acid sequence of open reading frame "a" of FIG. 2.

The invention further provides for the isolation of nucleic acid sequences having about 50% or greater sequence identity to RPS2 by using the RPS2 sequence of FIG. 2 or a portion thereof greater than 9 nucleic acids in length, and preferably greater than about 18 nucleic acids in length as a probe. Appropriate reduced hybridization stringency conditions are utilized to isolate DNA sequences having about 50% or greater sequence identity to the RPS2 sequence of FIG. 2.

Also provided by the invention are short conserved regions characteristic of RPS disease resistance genes. These conserved regions provide oligonucleotide sequences useful for the production of hybridization probes and PCR primers for the isolation of other plant disease-resistance genes.

Both the RPS2 gene and related RPS family genes provide disease resistance to plants, especially crop plants, most especially important crop plants such as tomato, pepper, maize, wheat, rice and legumes such as soybean and bean, or any plant which is susceptible to pathogens carrying an avirulence gene, e.g., the avrRpt2 avirulence gene. Such pathogens include, but are not limited to, *Pseudomonas syringae* strains.

The invention also includes any biologically active fragment or analog of an Rps2 polypeptide. By "biologically active" is meant possessing any in vivo activity which is characteristic of the Rps2 polypeptide shown in FIG. 2. A useful Rps2 fragment or Rps2 analog is one which exhibits a biological activity in any biological assay for disease resistance gene product activity, for example, those assays described by Dong et al. (1991), supra; Yu et al. (1993) supra; Kunkel et al. (1993) supra; and Whalen et al. (1991). In particular, a biologically active Rps2 polypeptide fragment or analog is capable of providing substantial resistance to plant pathogens carrying the avrRpt2 avirulence gene. By substantial resistance is meant at least partial reduction in susceptibility to plant pathogens carrying the avrRpt2 gene.

Preferred analogs include Rps2 polypeptides (or biologically active fragments thereof) whose sequences differ from the wild-type sequence only by conservative amino acid substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity.

Analogs can differ from naturally occurring Rps2 polypeptide in amino acid sequence or can be modified in ways that do not involve sequence, or both. Analogs of the invention will generally exhibit at least 70%, preferably 80%, more preferably 90%, and most preferably 95% or even 99%, homology with a segment of 20 amino acid residues, preferably 40 amino acid residues, or more preferably the entire sequence of a naturally occurring Rps2 polypeptide sequence.

Alterations in primary sequence include genetic variants, both natural and induced. Also included are analogs that include residues other than naturally occurring L-amino acids, e.g., D-amino acids or non-naturally occurring or synthetic amino acids, e.g., $\beta$ or $\gamma$ amino acids. Also included in the invention are Rps2 polypeptides modified by in vivo chemical derivatization of polypeptides, including acetylation, methylation, phosphorylation, carboxylation, or glycosylation.

In addition to substantially full-length polypeptides, the invention also includes biologically active fragments of the polypeptides. As used herein, the term "fragment", as applied to a polypeptide, will ordinarily be at least 20 residues, more typically at least 40 residues, and preferably at least 60 residues in length. Fragments of Rps2 polypeptide can be generated by methods known to those skilled in the art. The ability of a candidate fragment to exhibit a biological activity of Rps2 can be assessed by those methods described herein. Also included in the invention are Rps2 polypeptides containing residues that are not required for biological activity of the peptide, e.g., those added by alternative mRNA splicing or alternative protein processing events.

Other embodiments are within the following claims.

What is claimed is:

1. A method of identifying a plant disease-resistance gene comprising:
   (a) providing a plant tissue sample comprising a mutant disease-resistance gene;
   (b) co-introducing by biolistic transformation into said plant tissue sample a candidate plant disease-resistance gene and a reporter gene, wherein said transformation results in expression of said candidate plant disease-resistance gene and said reporter gene within said plant tissue sample, and wherein said reporter gene is the *Eseherichia coli* uidA gene encoding β-glucuronidase (GUS); and
   (c) detecting the presence or absence of a disease-resistance response in said plant tissue sample, whereby a response identifies a plant disease-resistance gene.

2. The method of claim 1, wherein, in step (c), the presence or absence of a disease-resistance response is detected by histochemically measuring GUS activity.

* * * * *